US009603920B2

(12) United States Patent
Diaz-Mitoma et al.

(10) Patent No.: US 9,603,920 B2
(45) Date of Patent: Mar. 28, 2017

(54) COMPOSITIONS AND METHODS FOR TREATING INFLUENZA

(71) Applicant: Variation Biotechnologies, Inc., Gatineau (CA)

(72) Inventors: Francisco Diaz-Mitoma, Ottawa (CA); Andrei Ogrel, Russell (CA); Jose V. Torres, Davis, CA (US); David E. Anderson, Boston, MA (US)

(73) Assignee: Variation Biotechnologies, Inc., Ottawa (CA)

( * ) Notice: Subject to any disclaimer, the term of this patent is extended or adjusted under 35 U.S.C. 154(b) by 0 days.

(21) Appl. No.: 14/161,842

(22) Filed: Jan. 23, 2014

(65) Prior Publication Data

US 2014/0370041 A1 Dec. 18, 2014

Related U.S. Application Data

(63) Continuation of application No. 12/999,725, filed as application No. PCT/US2009/047911 on Jun. 19, 2009, now abandoned, which is a continuation-in-part of application No. PCT/US2008/067471, filed on Jun. 19, 2008.

(60) Provisional application No. 61/182,614, filed on May 29, 2009.

(51) Int. Cl.

| | |
|---|---|
| ***A61K 39/145*** | (2006.01) |
| ***A61K 39/12*** | (2006.01) |
| ***C07K 7/08*** | (2006.01) |
| ***C07K 14/00*** | (2006.01) |
| ***C12N 7/00*** | (2006.01) |
| ***A61K 39/39*** | (2006.01) |
| ***C07K 14/005*** | (2006.01) |
| ***A61K 38/16*** | (2006.01) |
| *A61K 39/00* | (2006.01) |

(52) U.S. Cl.

CPC .......... *A61K 39/145* (2013.01); *A61K 38/162* (2013.01); *A61K 39/12* (2013.01); *A61K 39/39* (2013.01); *C07K 7/08* (2013.01); *C07K 14/00* (2013.01); *C07K 14/005* (2013.01); *C12N 7/00* (2013.01); *A61K 39/00* (2013.01); *A61K 2039/542* (2013.01); *A61K 2039/55505* (2013.01); *A61K 2039/55511* (2013.01); *A61K 2039/55555* (2013.01); *A61K 2039/55561* (2013.01); *A61K 2039/55572* (2013.01); *A61K 2039/6018* (2013.01); *C12N 2760/16122* (2013.01); *C12N 2760/16134* (2013.01); *C12N 2760/16171* (2013.01); *C12N 2760/16222* (2013.01); *C12N 2760/16234* (2013.01); *C12N 2760/16271* (2013.01)

(58) Field of Classification Search

None

See application file for complete search history.

(56) References Cited

U.S. PATENT DOCUMENTS

| | | | |
|---|---|---|---|
| 3,952,097 | A | 4/1976 | Levy |
| 4,024,241 | A | 5/1977 | Levy |
| 4,349,538 | A | 9/1982 | Levy |
| 4,436,727 | A | 3/1984 | Ribi |
| 4,912,094 | A | 3/1990 | Myers et al. |
| 4,983,387 | A | 1/1991 | Goldstein et al. |
| 5,010,175 | A | 4/1991 | Rutter et al. |
| 5,057,540 | A | 10/1991 | Kensil et al. |
| 5,817,318 | A | 10/1998 | Sia et al. |
| 5,824,506 | A | 10/1998 | Chan et al. |
| 5,861,243 | A | 1/1999 | Dietrich et al. |
| 5,876,721 | A | 3/1999 | Alexander et al. |
| 5,939,074 | A | 8/1999 | Berzofsky |
| 5,977,081 | A | 11/1999 | Marciani |
| 6,005,099 | A | 12/1999 | Davies et al. |
| 6,080,725 | A | 6/2000 | Marciani |
| 6,090,392 | A | 7/2000 | Berman |
| 6,235,888 | B1 | 5/2001 | Pachuk et al. |
| 6,383,806 | B1 | 5/2002 | Rios |
| 6,500,623 | B1 | 12/2002 | Tung |
| 6,503,753 | B1 | 1/2003 | Rios |
| 6,538,123 | B2 | 3/2003 | Barban |
| 6,541,003 | B1 | 4/2003 | Smith |
| 6,592,871 | B1 | 7/2003 | Seidel et al. |
| 6,649,410 | B2 | 11/2003 | Rios |
| 6,653,130 | B2 | 11/2003 | Rios |
| 6,692,955 | B1 | 2/2004 | Meredith et al. |

(Continued)

FOREIGN PATENT DOCUMENTS

| | | |
|---|---|---|
| CN | 1625409 | 6/2005 |
| EP | 541335 A1 | 5/1993 |

(Continued)

OTHER PUBLICATIONS

Office Action issued against corresponding Israeli Patent Application No. 210097, dated Sep. 20, 2015, with its English translation.
GenBank Accession#ACC59536, hemagglutinin, partial [Influenza A virus (A/Iquitos/FLU4977/2006 (H1))], 2008.
GenBank Accession#ABC40619, hemagglutinin [Influenza A virus (A/HongKong/49/1974 (H3N2))], 2005.
GenBank Accession#CAD30198, nucleoprotein, partial [Influenza A virus (A/Egypt/96/2002 (H1N2))], 2002.
GenBank Accession#CAD33844, hemagglutinin, partial [Influenza B virus (B/Oslo/1846/2002)], 2003.
Final Rejection for corresponding Japanese Patent Application No. 2011-514829 dated Nov. 25, 2014, with English translation.

(Continued)

*Primary Examiner* — Benjamin P Blumel
(74) *Attorney, Agent, or Firm* — Borden Ladner Gervais LLP; David Nauman

(57) ABSTRACT

The present application provides compositions and methods useful for treating influenza. As described herein, the compositions and methods are based on the development of peptides and peptide combinations which exhibit immunogenic properties against influenza. In some embodiments, the peptide combinations induce a protective response against multiple strains of influenza, e.g., seasonal strains of influenza or even the new pandemic influenza A (H1N1) virus of swine origin.

22 Claims, 16 Drawing Sheets

(56) References Cited

U.S. PATENT DOCUMENTS

| | | | |
|---|---|---|---|
| 6,706,859 | B1 | 3/2004 | Sorensen |
| 6,787,351 | B2 | 9/2004 | Chen et al. |
| 6,831,169 | B2 | 12/2004 | Pachuk et al. |
| 7,063,849 | B1 | 6/2006 | Thibodeau et al. |
| 7,067,134 | B1 | 6/2006 | Kang et al. |
| 7,202,034 | B2 | 4/2007 | Van Der Burg et al. |
| 7,348,011 | B2 | 3/2008 | Guntaka et al. |
| 7,928,190 | B2 | 4/2011 | Darnell |
| 2002/0183484 | A1 | 12/2002 | Torres |
| 2004/0071661 | A1 | 4/2004 | Klatzmann et al. |
| 2005/0042229 | A1 | 2/2005 | Yang et al. |
| 2006/0217338 | A1 | 9/2006 | Lu et al. |
| 2007/0184526 | A1 | 8/2007 | Smith et al. |
| 2007/0286869 | A1 | 12/2007 | Luke et al. |
| 2009/0041809 | A1 | 2/2009 | Emtage |
| 2009/0081254 | A1 | 3/2009 | Vajday et al. |
| 2009/0117141 | A1 | 5/2009 | Torres et al. |
| 2009/0136543 | A1 | 5/2009 | Ballou et al. |
| 2009/0169505 | A1 | 7/2009 | Draghia-Akli et al. |

FOREIGN PATENT DOCUMENTS

| | | | |
|---|---|---|---|
| EP | 729473 | B1 | 9/1996 |
| GB | 2122204 | A | 1/1984 |
| WO | 8806882 | | 9/1988 |
| WO | 9319781 | | 10/1993 |
| WO | 9517210 | A1 | 6/1995 |
| WO | 9801139 | A1 | 1/1998 |
| WO | 03066090 | A1 | 8/2003 |
| WO | 2004058188 | A2 | 7/2004 |
| WO | 2006/092046 | A1 | 9/2006 |
| WO | 20060128294 | A1 | 12/2006 |
| WO | 2008/064488 | A1 | 6/2008 |
| WO | 2009/155489 | A2 | 12/2009 |

OTHER PUBLICATIONS

Office Action issued against corresponding Korean Patent Application No. 10-2011-7001217 dated Jan. 19, 2016, with its English translation.

International Preliminary Report on Patentability for corresponding International Application No. PCT/US2009/047911 dated Jan. 6, 2011.

International Search Report for corresponding International Application No. PCT/US2009/047911 dated Feb. 2, 2010.

Field, A.K., et al. "Inducers of Interferon and Host Resistance, II. Multistranded Synthetic Polynucleotide Complexes," Biochemistry, vol. 58, pp. 1004-1010, 1967.

Geysen, Mario H., et al. "Use of peptide synthesis to probe viral antigens for epitopes to a resolution of a single amino acid," Proc. Natl. Acad. Sci., vol. 81, pp. 3998-4002, Jul. 1984.

Houghten, Richard A. "General method for the rapid solid-phase synthesis of large numbers of peptides: Specificity of antigen-antibody interaction at the level of individual amino acids," Proc. Natl. Acad. Sci, vol. 82, pp. 5131-5135, Aug. 1985.

Kirby, Christopher et al. "Dehydration-Rehydration Vesicles: A Simple Method for High Yield Drug Entrapment in Liposomes," Biotechnology, pp. 979-984, Nov. 1984.

Lavanchy, Daniel. "The importance of global surveillance of influenza," Vaccine, vol. 17, pp. S24-S25, 1999.

Levy, Hilton B., et al. "Inhibition of Tumor Growth by Polyinosinic-Polycytidylic Acid," Proc. N.A.S., vol. 62, pp. 357-361, 1969.

Pick, Uri. "Liposomes with a Large Trapping Capacity Prepared by Freezing and Thawing of Sonicated Phospholipid Mixtures," Archives of Biochemistry and Biophysics, vol. 212, No. 1, pp. 186-194, 1981.

Russell, David G., et al. "Effective Immunization Against Cutaneous Leishmaniasis With Defined Membrane Antigens Reconstituted Into Liposomes," The Journal of Immunology, vol. 140, issue No. 4, pp. 1274-1279, Feb. 15, 1988.

Collins, M. et al. "Non-Ionic Surfactant Vesicle Formulation of Stibogluconate for Canine Leishmaniasis," Journal of Pharmacy & Pharmacology, vol. 42 Supplement, Dec. 1990.

Mann, Jamie F.S. et al. "Optimisation of a lipid based oral delivery system containing A/Panama influenza haemagglutinin," Vaccine, vol. 22, pp. 2425-2429, 2004.

Examination Report No. 1 for corresponding Australian Patent Application No. 2009259964, dated Jan. 15, 2014.

Rejection Decision for corresponding Chinese Application No. 200980132130.8, dated Mar. 19, 2014, with English translation.

Office Action for corresponding Japanese Application No. 2011-514829, dated Nov. 19, 2013, with English translation.

Office Action dated Jul. 24, 2013 from parent U.S. Appl. No. 12/999,725.

Restriction Requirement dated Nov. 28, 2012 from parent U.S. Appl. No. 12/999,725.

First Office Action for corresponding Chinese Application No. 200980132130.8, dated Aug. 31, 2012, with English translation.

Second Office Action for corresponding Chinese Application No. 200980132130.8, dated Jul. 12, 2013, with English translation.

Office Action for corresponding Israeli Patent Application No. 210097 dated Feb. 17, 2014, with English translation.

Hata et al., "Sequence characteristics of HA gene in influenza type A (H1 N1) virus isolated during the 2005-2006 season in Aichi Prefecture, Japan," Jpn. J. Infect. Dis., 59(3):209-211 (2006).

Kawakami et al., "Isolation of Influenza A H1 N2 Viruses from an Outbreak in Yokohama City during the 2001-2002 Influenza Season in Japan," Japanese journal of infectious diseases, Jul. 2003, vol. 56 (3), pp. 110-113.

Luo et al., "Evolutionary pattern of influenza B viruses based on the HA and NS genes during 1940 to 1999: origin of the NS genes after 1997," Arch. Viral., 144(10):1881-1891 (1999).

McCullers et al., "Multiple genotypes of influenza B virus circulated between 1979 and 2003," J. Viral., 78(23):12817-12828 (2004).

Office Action No. 4 dated Oct. 10, 2016 issued on the corresponding Chinese application No. 200980132130.8 without English translation.

Rota et al., "Antigenic and Genetic Characterization of the Haemagglutinins of Recent Cocirculating Strains of Influenza B virus," Journal of General Virology, Jun. 1992, vol. 73, pp. 2737-2742.

Written Opinion for Application No. PCT/US2009/047911, mailed on Feb. 2, 2010, 5 pages.

Office Action No. 3 dated Oct. 10, 2016 issued on the corresponding Chinese application No. 200980132130.8 with English translation.

SEQ ID NO. 16

CELLISRESWSYIVEKPNPENGTCYPGHFSWPNHTTTGVSASCSHNGESSFYKNLLWLTG
KNGLYPNLSKSYANNKEKEVLVLWGVHHPPNIGDQRALYHKENAYVSVVSHYSRKFTPEI
AKRPKVRDQEGRINYYWTLLEPGIIFEANGPVTIGECPKYVRSAKLRMVTGLRNIPSIQS

SEQ ID NO. 17

| Description | Sequence |
|---|---|
| Consensus | YAXKXGGKSSGSSYPVLXXXX |
| Substitution # 1 | --S-R-------------NVSY |
| Substitution # 2 | --C-H-------------SSTM |
| Substitution # 3 | ----Y-------------K--- |

SEQ ID NO. 18

NAEKAPGGPYKIGTSGSSPNVTNGNGFFATMAWAVPKNDNNKTATNSLTIEVPYISTEGE
DQITIWGFHSDNETQMAKLYGDSKPQKFTSSANGVTTHYVSQIGGFPNQTEDGGLPQSGR
IGTITYQ

FIGURE 9

COMPOSITIONS AND METHODS FOR TREATING INFLUENZA

RELATED APPLICATIONS

This application claims priority to and benefit of PCT Patent Application No. PCT/US08/67471 filed Jun. 19, 2008 and U.S. Provisional Application No. 61/182,614 filed May 29, 2009. The contents of these priority applications are incorporated herein by reference in their entirety.

INCORPORATION OF SEQUENCE LISTING

A computer readable form of the Sequence Listing "Sequence Listing.txt", submitted via EFS-WEB and created on Aug. 25, 2014, is herein incorporated by reference.

BACKGROUND

Influenza is a common infectious disease of the respiratory system associated with the Orthomyxoviridae family of viruses. Because of the high degree of variability of the virus, vaccination is typically required on a yearly basis with a reformulated vaccine that takes into account strain variations. The vaccine composition developed each year in the United States is determined by the Department of Food and Drug Administration Vaccines and the Related Biologicals Advisory Committee. The World Health Organization (WHO) similarly operates a global surveillance network of laboratories, for detection of new influenza variants, e.g., see Lavanchy, *Vaccine* 17: S24 (1999). Selection is based on antigenic analysis of recently isolated influenza viruses, the patterns of spread of antigenic variants, and the antibody responses of recently vaccinated individuals.

Influenza A and B are the two types of influenza viruses that cause epidemic human disease. Influenza A viruses are further categorized into subtypes on the basis of two surface antigens: hemagglutinin (HA) and neuraminidase (N). Influenza B viruses are not categorized into subtypes. Since 1977, influenza A (H1N1) viruses, influenza A (H3N2) viruses and influenza B viruses have been in global circulation. Vaccination is recognized as the single most effective way of preventing or attenuating influenza for those at high risk of serious illness from influenza infection and related complications. The inoculation of antigen prepared from inactivated influenza virus stimulates the production of specific antibodies. Protection is afforded only against those strains of virus from which the vaccine is prepared or closely related strains.

Each year's vaccine contains three virus strains (usually two type A and one type B) representing the influenza viruses that are believed likely to circulate in the coming winter. The antigenic characteristics of current and emerging influenza virus strains provide the basis for selecting strains included in each year's vaccine. The WHO reviews the world epidemiological situation annually and if necessary recommends new strains based on the current epidemiological evidence.

Despite the recomposition, it is not possible for a vaccine to include all the different strains actively infecting people in the world during a particular season. In addition, a relatively long length of time is also required to formulate and prepare sufficient quantities of vaccine doses for responding to seasonal increases in flu infections. Typically, it can take over six months to prepare a vaccine. As a result, new or overlooked influenza strains can become prominent during that six month period, leading to an epidemic. In April 2009 a novel influenza A (H1N1) virus of swine origin was first detected. It is a quadruple reassortant compared to the previously described H1N1 subtype. The initial outbreak of the virus was in Mexico but the epidemic has spread rapidly over the borders through the United States and Canada and now almost all international countries are reporting new cases. There remains a need in the art for improved compositions and methods for treating influenza. In particular, there is a need for compositions that have broad immunogenicity against both seasonal influenza strains recommended by WHO and against new emerging pandemic influenza strains such as the new influenza A (H1N1) virus of swine origin.

SUMMARY

The present application provides compositions and methods useful for treating influenza. As described herein, the compositions and methods are based on the development of peptides and peptide combinations which exhibit immunogenic properties against influenza.

In some embodiments, the peptide combinations induce a protective response against multiple strains of influenza, e.g., seasonal strains of influenza or even the new pandemic influenza A (H1N1) virus of swine origin.

In some embodiments, the compositions are administered parenterally (e.g., via intramuscular injection). In some embodiments, the parenteral compositions include a vesicle that comprises a non-ionic surfactant. In some embodiments, the parenteral compositions include TLR-4 agonist adjuvants. In some embodiments at least a portion of the TLR-4 agonist adjuvant present in the parenteral composition is physically associated with the vesicle.

While influenza vaccines are currently limited to the aforementioned parenteral administration routes (e.g., intramuscular injection), we have identified compositions that induce a protective response when administered orally. Therefore, in some embodiments, the compositions are administered orally. In some embodiments, the oral compositions include a bilosome. In some embodiments, the oral compositions include TLR-3 agonist adjuvants. In some embodiments at least a portion of the TLR-3 agonist adjuvant present in the oral composition is physically associated with the bilosome.

BRIEF DESCRIPTION OF THE DRAWINGS

As shown in FIG. 8, animals that received the adjuvant showed a much greater response than did animals that received vaccine alone.

FIG. 9 shows the sequences of SEQ ID NOs. 16, 17 and 18.

DEFINITIONS

Figure 1A:
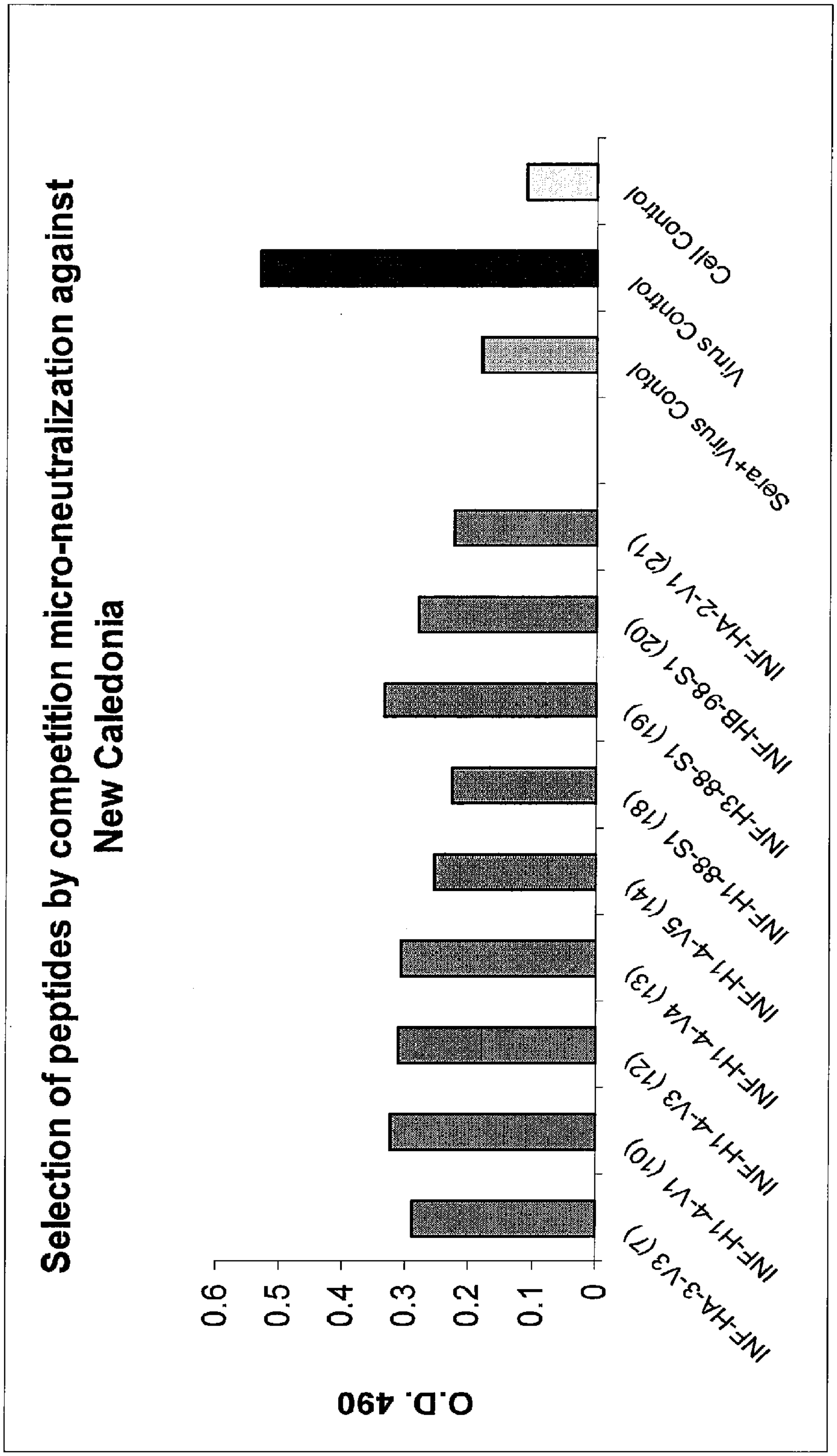
FIGS. 1A-B show the specificity of exemplary peptide compositions as detected by competition micro-neutralization assay. Human sera were diluted and incubated with selected peptide compositions and subsequently with influenza viruses. After incubation, MDCK (Madin-Darby Canine Kidney) cells were added and the plates were developed 18-22 hours later. (A) Competition micro-neutralization was detected against influenza New Caledonia (A/NC/20/99) using human sera. (B) Competition micro-neutralization was detected against influenza Wisconsin (A/Wis/67/05) using human sera.

Throughout the present application, several terms are employed that are defined in the following paragraphs.

As used herein, the term "immune response" refers to a response elicited in an animal. An immune response may refer to cellular immunity, humoral immunity or may involve both. An immune response may also be limited to a part of the immune system. For example, in some embodiments, an immunogenic composition may induce an increased IFNγ response. In some embodiments, an immunogenic composition may induce a mucosal IgA response (e.g., as measured in nasal and/or rectal washes). In some embodiments, an immunogenic composition may induce a systemic IgG response (e.g., as measured in serum).

As used herein, the term "immunogenic" means capable of producing an immune response in a host animal against a non-host entity (e.g., an influenza virus). In some embodiments, this immune response forms the basis of the protective immunity elicited by a vaccine against a specific infectious organism (e.g., an influenza virus).

As used herein, the term "peptide" refers to a string of at least three amino acids linked together by peptide bonds. In general, there is no upper limit on the number of amino acids in a peptide. A peptide will generally contain only natural amino acids; however, non-natural amino acids (i.e., amino acids that do not occur in nature but that can be incorporated into a polypeptide chain) may be included. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In various embodiments, the modification(s) lead to a more stable peptide (e.g., greater half-life in vivo). Suitable modifications may include cyclization of the peptide, the incorporation of D-amino acids, etc. In various embodiments, the modification(s) lead to a more immunogenic peptide. Suitable modifications may include covalent attachment of one or more lipids (e.g., without limitation, palmitoyl, myristoyl, stearoyl, lauroyl, octanoyl, decanoyl, etc.), fusion to a carrier protein (e.g., without limitation, purified protein derivative of tuberculin (PPD), tetanus toxoid, cholera toxin and its B subunit, ovalbumin, bovine serum albumin, soybean trypsin inhibitor, muramyldipeptide and analogues thereof, a cytokine or fragment thereof, etc.), etc.

As used herein, the terms "percentage homology" refer to the percentage of sequence identity between two sequences after optimal alignment as defined in the present application. Two amino acid sequences are said to be "identical" if the sequence of amino acids in the two sequences is the same when aligned for maximum correspondence as described below. Sequence comparisons between two amino acid sequences are typically performed by comparing sequences of two optimally aligned sequences over a region or "comparison window" to identify and compare regions of sequence similarity. Optimal alignment of sequences for comparison may be conducted by the local homology algorithm of Smith and Waterman, *Ad. App. Math.* 2:482 (1981), by the homology alignment algorithm of Neddleman and Wunsch, *J. Mol. Biol.* 48:443 (1970), by the search for similarity method of Pearson and Lipman, *Proc. Natl. Acad. Sci. USA* 85:2444 (1988), by computerized implementation of these algorithms, or by visual inspection.

"Percentage of sequence identity" is determined by comparing two optimally aligned sequences over a comparison window, where the portion of the amino acid sequence in the comparison window may comprise additions or deletions (i.e., gaps) as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. This definition of sequence identity given above is the definition that would be used by one of ordinary skill in the art. The definition by itself does not need the help of any algorithm. The algorithms are only helpful to facilitate the optimal alignments of sequences, rather than calculate sequence identity. From this definition, it follows that there is a well defined and only one value for the sequence identity between two compared sequences which value corresponds to the value obtained for the optimal alignment.

As used herein, the terms "therapeutically effective amount" refer to the amount sufficient to show a meaningful benefit in a subject being treated. The therapeutically effective amount of an immunogenic composition may vary depending on such factors as the desired biological endpoint, the nature of the composition, the route of administration, the health, size and/or age of the subject being treated, etc.

As used herein, the term "treat" (or "treating", "treated", "treatment", etc.) refers to the administration of an immunogenic composition to a subject who has influenza, a symptom of influenza or a predisposition toward influenza, with the purpose to alleviate, relieve, alter, ameliorate, improve or affect the influenza, a symptom or symptoms of influenza, or the predisposition toward influenza. In some embodiments, the term "treating" refers to the vaccination of a subject.

DETAILED DESCRIPTION OF SOME EMBODIMENTS

The present application provides compositions and methods useful for treating influenza. As described herein, the compositions and methods are based on the development of peptides and peptide combinations which exhibit immunogenic properties against influenza.

In some embodiments, the peptide combinations induce a protective response against multiple strains of influenza, e.g., seasonal strains of influenza or even the new pandemic influenza A (H1N1) virus of swine origin.

In some embodiments, the compositions are administered parenterally (e.g., via intramuscular injection). In some embodiments, the compositions include TLR-4 agonist adjuvants. In some embodiments, the compositions include a vesicle that comprises a non-ionic surfactant. In some embodiments at least a portion of the TLR-4 agonist adjuvant present in the composition is physically associated with the vesicle.

While influenza vaccines are currently limited to the aforementioned parenteral administration routes (e.g., intramuscular injection), we have identified compositions that induce a protective response when administered orally. Therefore, in some embodiments, the compositions are administered orally. In some embodiments, the compositions include TLR-3 agonist adjuvants. In some embodiments, the compositions include a bilosome. In some embodiments at least a portion of the TLR-3 agonist adjuvant present in the composition is physically associated with the bilosome.

I. Peptides

In one aspect, the present application provides peptides that can be used alone or in combination to produce an immunogenic composition for treating influenza. It is to be understood that any of these peptides may be included in an immunogenic composition and that the present application encompasses compositions that include any permutation or combination of these peptides. Section II below describes some exemplary peptide combinations.

Type A Influenza Hemagglutinin (HA) Subtype 1 (H1) Peptides

Tables 2-6 in the Examples describe the amino acid sequences of several peptides that have been derived from type A influenza hemagglutinin (HA) subtype 1 (H1) proteins. As shown in Tables 2-5 and the Sequence Listing, some of the peptides are variants of a common consensus sequence.

In some embodiments, the present application provides peptides that comprise at least 20 contiguous amino acids of SEQ ID NO. 2 (see Table 2). It will be appreciated that any 20 contiguous amino acids of any one of the variant sequences described by the consensus sequence of SEQ ID NO. 2 is encompassed. In some embodiments, a peptide may comprise at least 21, 22, 23, 24, 25 or 26 contiguous amino acids of SEQ ID NO. 2. The present application also provides immunogenic compositions which comprise two or more of these peptides. Thus, in some embodiments, an immunogenic composition may comprise 2, 3, 4, 5, 6, 7 or 8 different peptides which comprise at least 20 contiguous amino acids of SEQ ID NO. 2. In some embodiments, an immunogenic composition may comprise $2^n$ different peptides each comprising a different amino acid sequence of SEQ ID NO. 2, where n=1-3. In some embodiments, n=1. In some embodiments, n=2. In some embodiments, n=3.

In some embodiments, the present application provides peptides that comprise at least 20 contiguous amino acids of SEQ ID NO. 3 (see Table 3). It will be appreciated that any 20 contiguous amino acids of any one of the variant sequences described by the consensus sequence of SEQ ID NO. 3 is encompassed. In some embodiments, a peptide may comprise at least 21, 22, 23, 24, 25, 26, 27, 28, 29, 30, 31, 32 or 33 contiguous amino acids of SEQ ID NO. 3. The present application also provides immunogenic compositions which comprise two or more of these peptides. Thus, in some embodiments, an immunogenic composition may comprise 2, 3, 4, 5, 6, 7 or 8 different peptides which comprise at least 20 contiguous amino acids of SEQ ID NO. 3. In some embodiments, an immunogenic composition may comprise $2^n$ different peptides each comprising a different amino acid sequence of SEQ ID NO. 3, where n=1-3. In some embodiments, n=1. In some embodiments, n=2. In some embodiments, n=3.

In some embodiments, the present application provides peptides that comprise at least 20 contiguous amino acids of SEQ ID NO. 4 (see Table 4). It will be appreciated that any 20 contiguous amino acids of any one of the variant sequences described by the consensus sequence of SEQ ID NO. 4 is encompassed. In some embodiments, a peptide may comprise at least 21, 22, 23, 24, 25, 26, 27, 28, 29 or 30 contiguous amino acids of SEQ ID NO. 4. The present application also provides immunogenic compositions which comprise two or more of these peptides. Thus, in some embodiments, an immunogenic composition may comprise 2, 3 or 4 different peptides which comprise at least 20 contiguous amino acids of SEQ ID NO. 4. In some embodiments, an immunogenic composition may comprise $2^n$ different peptides each comprising a different amino acid sequence of SEQ ID NO. 4, where n=1-2. In some embodiments, n=1. In some embodiments, n=2.

In some embodiments, the present application provides peptides that comprise at least 20 contiguous amino acids of SEQ ID NO. 5 (see Table 5). It will be appreciated that any 20 contiguous amino acids of any one of the variant sequences described by the consensus sequence of SEQ ID NO. 5 is encompassed. In some embodiments, a peptide may comprise at least 21, 22, 23, 24, 25, 26, 27, 28 or 29 contiguous amino acids of SEQ ID NO. 5. The present application also provides immunogenic compositions which comprise two or more of these peptides. Thus, in some embodiments, an immunogenic composition may comprise 2, 3, 4, 5, 6, 7 or 8 different peptides which comprise at least 20 contiguous amino acids of SEQ ID NO. 5. In some embodiments, an immunogenic composition may comprise $2^n$ different peptides each comprising a different amino acid sequence of SEQ ID NO. 5, where n=1-3. In some embodiments, n=1. In some embodiments, n=2. In some embodiments, n=3.

In some embodiments, the present application provides peptides which comprise a region having at least 80% homology with at least 40 contiguous amino acids of SEQ ID NO. 6 (see Table 6). In some embodiments, the homology may be at least 85%, 90%, 95% or 99%.

In some embodiments, the present application provides peptides that comprise at least 40 contiguous amino acids of SEQ ID NO. 6. In some embodiments, the present application provides peptides that comprise at least 50, 60, 70 or 80 contiguous amino acids of SEQ ID NO. 6. Thus, a peptide may comprise amino acids 1-81 of SEQ ID NO. 6. A peptide may also comprise amino acids 82-88 of SEQ ID NO. 6. In some embodiments, a peptide may comprise the entire sequence of SEQ ID NO. 6. In other embodiments, a peptide may consist essentially of SEQ ID NO. 6. In yet other embodiments, a peptide may consist of SEQ ID NO. 6.

In addition to the foregoing, the present application also provides a genus of peptides that comprise a region having at least 80% homology with 20-100 contiguous amino acids of SEQ ID NO. 16 (see FIG. 9), wherein the peptide includes fewer than 100 contiguous amino acids from a type A influenza hemagglutinin (HA) protein. This genus encompasses the other H1 peptides described above. In some embodiments, the peptide may comprise a region having at least 85%, 90%, 95% or 99% homology with 20-100 contiguous amino acids of SEQ ID NO. 16. In some embodiments, the peptide may comprise a region having at least 80% homology with 20-50 contiguous amino acids of SEQ ID NO. 16. In some embodiments, the peptide may comprise a region having at least 80% homology with 50-100 contiguous amino acids of SEQ ID NO. 16.

In some embodiments, any of the aforementioned H1 peptides may comprise fewer than 30 amino acids. However, as discussed herein, in some embodiments, a peptide comprising any one of the defined regions may also be comprised within a larger peptide.

Type A Influenza Hemagglutinin (HA) Subtype 3 (H3) Peptides

Tables 9-11 in the Examples describe the amino acid sequences of several peptides that have been derived from type A influenza hemagglutinin (HA) subtype 3 (H3) proteins. As shown in Tables 9-11 and the Sequence Listing, these peptides are all variants of the consensus sequence of SEQ ID NO. 17 (see FIG. 9).

In some embodiments, the present application provides peptides that comprise a sequence of SEQ ID NO. 17. It will be appreciated that any one of the variant sequences described by the consensus sequence of SEQ ID NO. 17 is encompassed.

In some embodiments, the present application provides peptides that comprise a sequence of SEQ ID NO. 9 (see Table 9). It will be appreciated that any one of the variant sequences described by the consensus sequence of SEQ ID NO. 9 is encompassed. The present application also provides immunogenic compositions which comprise two or more of these peptides. Thus, in some embodiments, an immunogenic composition may comprise 2, 3, 4, 5, 6, 7, 8, 9, 10, 11, 12, 13, 14, 15 or 16 different peptides that comprise a sequence of SEQ ID NO. 9. In some embodiments, an immunogenic composition may comprise $2^n$ different peptides each comprising a different amino acid sequence of SEQ ID NO. 9, where n=1-4. In some embodiments, n=1. In some embodiments, n=2. In some embodiments, n=3. In some embodiments, n=4. It is to be understood that the present application also provides peptides which consist essentially of or consist of an amino acid sequence of SEQ ID NO. 9.

In some embodiments, the present application provides peptides that comprise a sequence of SEQ ID NO. 10 (see Table 10). It will be appreciated that any one of the variant sequences described by the consensus sequence of SEQ ID NO. 10 is encompassed. The present application also provides immunogenic compositions which comprise two or more of these peptides. Thus, in some embodiments, an immunogenic composition may comprise 2, 3, 4, 5, 6, 7, 8, 9, 10, 11, 12, 13, 14, 15 or 16 different peptides that comprise a sequence of SEQ ID NO. 10. In some embodiments, an immunogenic composition may comprise $2^n$ different peptides each comprising a different amino acid sequence of SEQ ID NO. 10, where n=1-4. In some embodiments, n=1. In some embodiments, n=2. In some embodiments, n=3. In some embodiments, n=4. It is to be understood that the present application also provides peptides which consist essentially of or consist of an amino acid sequence of SEQ ID NO. 10.

In some embodiments, the present application provides peptides that comprise a sequence of SEQ ID NO. 11 (see Table 11). It will be appreciated that any one of the variant sequences described by the consensus sequence of SEQ ID NO. 11 is encompassed. The present application also provides immunogenic compositions which comprise two or more of these peptides. Thus, in some embodiments, an immunogenic composition may comprise 2, 3, 4, 5, 6, 7, 8, 9, 10, 11, 12, 13, 14, 15 or 16 different peptides that comprise a sequence of SEQ ID NO. 11. In some embodiments, an immunogenic composition may comprise $2^n$ different peptides each comprising a different amino acid sequence of SEQ ID NO. 11, where n=1-4. In some embodiments, n=1. In some embodiments, n=2. In some embodiments, n=3. In some embodiments, n=4. It is to be understood that the present application also provides peptides which consist essentially of or consist of an amino acid sequence of SEQ ID NO. 11.

In some embodiments, any of the aforementioned H3 peptides may comprise fewer than 30 amino acids. However, as discussed herein, in some embodiments, a peptide comprising any one of the defined regions may also be comprised within a larger peptide.

Table 7 in the Examples describes the amino acid sequences of another peptide that has been derived from type A influenza hemagglutinin (HA) subtype 3 (H3) proteins. The present application provides a peptide comprising a region having at least 80% homology with at least 20 contiguous amino acids of SEQ ID NO. 7, wherein the peptide includes fewer than 100 contiguous amino acids from a type A influenza hemagglutinin protein. In some embodiments, a peptide may comprise a region having at least 85%, 90%, 95% or 99% homology with at least 20 contiguous amino acids of SEQ ID NO. 7. In some embodiments, a peptide may comprise a region having at least 80% homology with at least 50, 60, 70 or 80 contiguous amino acids of SEQ ID NO. 7. In some embodiments, a peptide may comprise the entire sequence of SEQ ID NO. 7. In other embodiments, a peptide may consist essentially of SEQ ID NO. 7. In yet other embodiments, a peptide may consist of SEQ ID NO. 7. In some embodiments, the peptide may comprise fewer than 100 amino acids, e.g., fewer than 90, 80, 70, 60, 50 or 40 amino acids. However, as discussed herein, in some embodiments, a peptide comprising any one of the defined regions may also be comprised within a larger peptide.

Type B Influenza Hemagglutinin (HA) Peptides

Tables 8 and 12 in the Examples describe the amino acid sequences of several peptides that have been derived from type B influenza hemagglutinin (HA) proteins.

In some embodiments, the present application provides peptides that comprise a region having at least 80% homology with at least 20 contiguous amino acids from positions 2-49 or 68-121 of SEQ ID NO. 18 (see FIG. 9), wherein the peptide includes fewer than 100 contiguous amino acids from a type B influenza hemagglutinin protein. In some embodiments, a peptide may comprise a region having at least 85%, 90%, 95% or 99% homology with at least 20 contiguous amino acids from positions 2-49 or 68-121 of SEQ ID NO. 18. In some embodiments, a peptide may comprise a region having at least 80% homology with at least 25, 30, 35, 40 or 45 contiguous amino acids from positions 2-49 or 68-121 of SEQ ID NO. 18.

In some embodiments, a peptide may comprise a region having at least 80% homology with the entire sequence of SEQ ID NO. 12 (see Table 12). In some embodiments, the level of homology may be at least 85%, 90%, 95% or 99%. In some embodiments, a peptide may comprise the entire sequence of SEQ ID NO. 12. In some embodiments, a peptide may consist essentially of SEQ ID NO. 12. In some embodiments, a peptide may consist of SEQ ID NO. 12.

In some embodiments, a peptide may comprise a region having at least 80% homology with the entire sequence of SEQ ID NO. 13 (see Table 12). In some embodiments, the level of homology may be at least 85%, 90%, 95% or 99%. In some embodiments, a peptide may comprise the entire sequence of SEQ ID NO. 13. In some embodiments, a peptide may consist essentially of SEQ ID NO. 13. In some embodiments, a peptide may consist of SEQ ID NO. 13.

In some embodiments, a peptide may comprise a first region having at least 80% homology with at least 20 contiguous amino acids from positions 2-49 and a second region having at least 80% homology with at least 20 contiguous amino acids from positions 68-121 of SEQ ID NO. 18. In some embodiments, the homology may be higher, e.g., at least 85%, 90%, 95% or 99%. In some embodiments, the homology in the first and/or second region may span at least 25, 20, 35, 40 or 45 contiguous amino acids from positions 2-49 or 68-121 of SEQ ID NO. 18.

In some embodiments, a peptide may comprise a region having at least 80% homology with the entire sequence of SEQ ID NO. 8 (see Table 8). In some embodiments, the level of homology may be at least 85%, 90%, 95% or 99%. In some embodiments, a peptide may comprise the entire sequence of SEQ ID NO. 8. In other embodiments, a peptide may consist essentially of or consist of the sequence of SEQ ID NO. 8.

In some embodiments, any of the aforementioned Type B HA peptides may comprise fewer than 100 amino acids, e.g., fewer than 90, 80, 70, 60, 50 or 40 amino acids. However, as discussed herein, in some embodiments, a peptide comprising any one of the defined regions may also be comprised within a larger peptide.

Type A Influenza Nucleoprotein (NP) Peptides

Tables 13 and 14 in the Examples describe the amino acid sequences of several peptides that have been derived from type A influenza nucleoproteins (NP). The peptides in Table 13 are variants of the consensus sequence of SEQ ID NO. 14. The peptides in Table 14 are variants of the consensus sequence of SEQ ID NO. 15.

In some embodiments, the present application provides peptides that comprise a sequence of SEQ ID NO. 14 (see Table 13), wherein the peptide includes fewer than 20 contiguous amino acids from a type A influenza nucleoprotein. It will be appreciated that any one of the variant sequences described by the consensus sequence of SEQ ID NO. 14 is encompassed. The present application also provides immunogenic compositions which comprise two or more of these peptides. Thus, in some embodiments, an immunogenic composition may comprise 2, 3, 4, 5, 6, 7, 8, 9, 10, 11, 12, 13, 14, 15 or 16 different peptides that comprise a sequence of SEQ ID NO. 14. In some embodiments, an immunogenic composition may comprise $2^n$ different peptides each comprising a different amino acid sequence of SEQ ID NO. 14, where n=1-4. In some embodiments, n=1. In some embodiments, n=2. In some embodiments, n=3. In some embodiments, n=4. It is to be understood that the present application also provides peptides which consist essentially of or consist of an amino acid sequence of SEQ ID NO. 14.

In some embodiments, the present application provides peptides that comprise a sequence of SEQ ID NO. 15 (see Table 14), wherein the peptide includes fewer than 20 contiguous amino acids from a type A influenza nucleoprotein. It will be appreciated that any one of the variant sequences described by the consensus sequence of SEQ ID NO. 15 is encompassed. The present application also provides immunogenic compositions which comprise two or more of these peptides. Thus, in some embodiments, an immunogenic composition may comprise 2, 3, 4, 5, 6, 7, 8, 9, 10, 11, 12, 13, 14, 15 or 16 different peptides that comprise a sequence of SEQ ID NO. 15. In some embodiments, an immunogenic composition may comprise $2^n$ different peptides each comprising a different amino acid sequence of SEQ ID NO. 15, where n=1-4. In some embodiments, n=1. In some embodiments, n=2. In some embodiments, n=3. In some embodiments, n=4. It is to be understood that the present application also provides peptides which consist essentially of or consist of an amino acid sequence of SEQ ID NO. 15.

In some embodiments, any of the aforementioned NP peptides may comprise fewer than 30 amino acids. However, as discussed herein, in some embodiments, a peptide comprising any one of the defined regions may also be comprised within a larger peptide.

Other Influenza Peptides

The present application provides other peptides which include sequences from more than one influenza protein. Thus, in some embodiments, the present application provides peptides which comprise an amino acid sequence of SEQ ID NO. 1 (see Table 1). As shown in Table 1 and the Sequence Listing, SEQ ID NO. 1 is a consensus sequence. The consensus sequence was derived from sequences in Type B influenza HA proteins and Type A influenza HA H3 proteins. It will be appreciated that any one of the variant sequences described by the consensus sequence of SEQ ID NO. 1 is encompassed. The present application also provides immunogenic compositions which comprise two or more of these peptides. Thus, in some embodiments, an immunogenic composition may comprise 2, 3, 4, 5, 6, 7, 8, 9, 10, 11, 12, 13, 14, 15 or 16 different peptides that comprise a sequence of SEQ ID NO. 1. In some embodiments, an immunogenic composition may comprise $2^n$ different peptides each comprising a different amino acid sequence of SEQ ID NO. 1, where n=1-4. In some embodiments, n=1. In some embodiments, n=2. In some embodiments, n=3. In some embodiments, n=4. It is to be understood that the present application also provides peptides which consist essentially of or consist of an amino acid sequence of SEQ ID NO. 1. It is also to be understood that in some embodiments a peptide may comprise fewer than 30 amino acids. However, as discussed herein, in some embodiments, a peptide comprising any one of the defined regions may also be comprised within a larger peptide.

II. Peptide Combinations

In one aspect, the present application provides immunogenic compositions that include combinations of peptides described in Section I. It is to be understood that the following exemplary combinations are non-limiting and that the present application encompasses all permutations and combinations of the peptides described in Section I. It is also to be understood that other peptides (including traditional influenza protein antigens found in existing influenza vaccines) may be added to any of the immunogenic compositions described herein. In some embodiments, each peptide in an immunogenic composition is independently immunogenic.

In some embodiments, at least one peptide comprises a region with 20 or more contiguous amino acids from a non-influenza protein. In some embodiments each peptide comprises a region with 20 or more contiguous amino acids from a non-influenza protein. In some embodiments, at least two peptides of the composition are present within a single protein.

In some embodiments, the present application provides immunogenic compositions that include one or more Type A influenza HA H1 peptides and one or more Type A influenza HA H3 peptides from Section I.

In some embodiments, the present application provides immunogenic compositions that include one or more Type A influenza HA H1 peptides and one or more Type B influenza HA peptides from Section I.

In some embodiments, the present application provides immunogenic compositions that include one or more Type A influenza HA H3 peptides and one or more Type B influenza HA peptides from Section I.

In some embodiments, the present application provides immunogenic compositions that include one or more Type A influenza HA H1 peptides, one or more Type A influenza HA H3 peptides and one or more Type B influenza HA peptides from Section I.

In some embodiments, one or more Type A influenza NP peptides from Section I can be included in any one of the aforementioned combinations.

In some embodiments, the present application provides immunogenic compositions which comprise a first peptide comprising a region having at least 80% homology with 20-100 contiguous amino acids of SEQ ID NO. 16, wherein the first peptide includes fewer than 100 contiguous amino acids from a type A influenza hemagglutinin protein; a second peptide comprising an amino acid sequence of SEQ ID NO. 17; and a third peptide comprising a region having at least 80% homology with at least 20 contiguous amino acids from positions 2-49 or 68-121 of SEQ ID NO. 18, wherein the third peptide includes fewer than 100 contiguous amino acids from a type B influenza hemagglutinin protein. In some embodiments, the first and third peptides comprise fewer than 100 amino acids and the second peptide comprises fewer than 30 amino acids.

In some embodiments, a fourth peptide comprising an amino acid sequence of SEQ ID NO. 14 or 15 is also included, wherein the fourth peptide includes fewer than 20 contiguous amino acids from a type A influenza nucleoprotein.

Exemplary First Peptides (Type A Influenza HA H1)

In some embodiments, the first peptide may comprise a region having at least 85%, 90%, 95% or 99% homology with 20-100 contiguous amino acids of SEQ ID NO. 16. In some embodiments, the first peptide may comprise a region having at least 80% homology with 20-50 contiguous amino acids of SEQ ID NO. 16. In some embodiments, the first peptide may comprise a region having at least 80% homology with 50-100 contiguous amino acids of SEQ ID NO. 16.

In some embodiments, the first peptide may comprise at least 20 contiguous amino acids of SEQ ID NO. 2 (see Table 2). It will be appreciated that any 20 contiguous amino acids of any one of the variant sequences described by the consensus sequence of SEQ ID NO. 2 is encompassed. In some embodiments, a first peptide may comprise at least 21, 22, 23, 24, 25 or 26 contiguous amino acids of SEQ ID NO. 2. The present application also provides immunogenic compositions which comprise two or more of these first peptides. Thus, in some embodiments, an immunogenic composition may comprise 2, 3, 4, 5, 6, 7 or 8 different first peptides which comprise at least 20 contiguous amino acids of SEQ ID NO. 2. In some embodiments, an immunogenic composition may comprise $2^n$ different first peptides each comprising a different amino acid sequence of SEQ ID NO. 2, where n=1-3. In some embodiments, n=1. In some embodiments, n=2. In some embodiments, n=3.

In some embodiments, the first peptide may comprise at least 20 contiguous amino acids of SEQ ID NO. 3 (see Table 3). It will be appreciated that any 20 contiguous amino acids of any one of the variant sequences described by the consensus sequence of SEQ ID NO. 3 is encompassed. In some embodiments, a first peptide may comprise at least 21, 22, 23, 24, 25, 26, 27, 28, 29, 30, 31, 32 or 33 contiguous amino acids of SEQ ID NO. 3. The present application also provides immunogenic compositions which comprise two or more of these first peptides. Thus, in some embodiments, an immunogenic composition may comprise 2, 3, 4, 5, 6, 7 or 8 different first peptides which comprise at least 20 contiguous amino acids of SEQ ID NO. 3. In some embodiments, an immunogenic composition may comprise $2^n$ different first peptides each comprising a different amino acid sequence of SEQ ID NO. 3, where n=1-3. In some embodiments, n=1. In some embodiments, n=2. In some embodiments, n=3.

In some embodiments, the first peptide may comprise at least 20 contiguous amino acids of SEQ ID NO. 4 (see Table 4). It will be appreciated that any 20 contiguous amino acids of any one of the variant sequences described by the consensus sequence of SEQ ID NO. 4 is encompassed. In some embodiments, a first peptide may comprise at least 21, 22, 23, 24, 25, 26, 27, 28, 29 or 30 contiguous amino acids of SEQ ID NO. 4. The present application also provides immunogenic compositions which comprise two or more of these first peptides. Thus, in some embodiments, an immunogenic composition may comprise 2, 3 or 4 different first peptides which comprise at least 20 contiguous amino acids of SEQ ID NO. 4. In some embodiments, an immunogenic composition may comprise $2^n$ different first peptides each comprising a different amino acid sequence of SEQ ID NO. 4, where n=1-2. In some embodiments, n=1. In some embodiments, n=2.

In some embodiments, the first peptide may comprise at least 20 contiguous amino acids of SEQ ID NO. 5 (see Table 5). It will be appreciated that any 20 contiguous amino acids of any one of the variant sequences described by the consensus sequence of SEQ ID NO. 5 is encompassed. In some embodiments, a first peptide may comprise at least 21, 22, 23, 24, 25, 26, 27, 28 or 29 contiguous amino acids of SEQ ID NO. 5. The present application also provides immunogenic compositions which comprise two or more of these first peptides. Thus, in some embodiments, an immunogenic composition may comprise 2, 3, 4, 5, 6, 7 or 8 different first peptides which comprise at least 20 contiguous amino acids of SEQ ID NO. 5. In some embodiments, an immunogenic composition may comprise $2^n$ different first peptides each comprising a different amino acid sequence of SEQ ID NO. 5, where n=1-3. In some embodiments, n=1. In some embodiments, n=2. In some embodiments, n=3.

In some embodiments, the first peptide may comprise a region having at least 80% homology with at least 40 contiguous amino acids of SEQ ID NO. 6 (see Table 6). In some embodiments, the homology may be at least 85%, 90%, 95% or 99%. In some embodiments, the first peptide may comprise at least 40 contiguous amino acids of SEQ ID NO. 6. In some embodiments, the first peptide may comprise at least 50, 60, 70 or 80 contiguous amino acids of SEQ ID NO. 6. Thus, a first peptide may comprise amino acids 1-81 of SEQ ID NO. 6. A first peptide may also comprise amino acids 82-88 of SEQ ID NO. 6. In some embodiments, a first peptide may comprise the entire sequence of SEQ ID NO. 6. In other embodiments, a first peptide may consist essentially of SEQ ID NO. 6. In yet other embodiments, a first peptide may consist of SEQ ID NO. 6.

In some embodiments, any of the aforementioned first peptides may comprise fewer than 30 amino acids. However, as discussed herein, in some embodiments, a first peptide comprising any one of the defined regions may also be comprised within a larger peptide.

Exemplary Second Peptides (Type A Influenza HA H3)

In some embodiments, the second peptide may comprise a sequence of SEQ ID NO. 17. It will be appreciated that any one of the variant sequences described by the consensus sequence of SEQ ID NO. 17 is encompassed.

In some embodiments, the second peptide may comprise a sequence of SEQ ID NO. 9 (see Table 9). It will be appreciated that any one of the variant sequences described by the consensus sequence of SEQ ID NO. 9 is encompassed. The present application also provides immunogenic compositions which comprise two or more of these second peptides. Thus, in some embodiments, an immunogenic composition may comprise 2, 3, 4, 5, 6, 7, 8, 9, 10, 11, 12, 13, 14, 15 or 16 different second peptides that comprise a sequence of SEQ ID NO. 9. In some embodiments, an immunogenic composition may comprise $2^n$ different second peptides each comprising a different amino acid sequence of SEQ ID NO. 9, where n=1-4. In some embodiments, n=1. In some embodiments, n=2. In some embodiments, n=3. In some embodiments, n=4. It is to be understood that the present application also provides second peptides which consist essentially of or consist of an amino acid sequence of SEQ ID NO. 9.

In some embodiments, the second peptide may comprise a sequence of SEQ ID NO. 10 (see Table 10). It will be appreciated that any one of the variant sequences described by the consensus sequence of SEQ ID NO. 10 is encompassed. The present application also provides immunogenic compositions which comprise two or more of these second peptides. Thus, in some embodiments, an immunogenic composition may comprise 2, 3, 4, 5, 6, 7, 8, 9, 10, 11, 12, 13, 14, 15 or 16 different second peptides that comprise a sequence of SEQ ID NO. 10. In some embodiments, an immunogenic composition may comprise $2^n$ different second peptides each comprising a different amino acid sequence of SEQ ID NO. 10, where n=1-4. In some embodiments, n=1. In some embodiments, n=2. In some embodiments, n=3. In some embodiments, n=4. It is to be understood that the present application also provides second peptides which consist essentially of or consist of an amino acid sequence of SEQ ID NO. 10.

In some embodiments, the second peptide may comprise a sequence of SEQ ID NO. 11 (see Table 11). It will be appreciated that any one of the variant sequences described by the consensus sequence of SEQ ID NO. 11 is encompassed. The present application also provides immunogenic compositions which comprise two or more of these second peptides. Thus, in some embodiments, an immunogenic composition may comprise 2, 3, 4, 5, 6, 7, 8, 9, 10, 11, 12, 13, 14, 15 or 16 different second peptides that comprise a sequence of SEQ ID NO. 11. In some embodiments, an immunogenic composition may comprise $2^n$ different second peptides each comprising a different amino acid sequence of SEQ ID NO. 11, where n=1-4. In some embodiments, n=1. In some embodiments, n=2. In some embodiments, n=3. In some embodiments, n=4. It is to be understood that the present application also provides second peptides which consist essentially of or consist of an amino acid sequence of SEQ ID NO. 11.

In some embodiments, any of the aforementioned second peptides may comprise fewer than 30 amino acids. However, as discussed herein, in some embodiments, a second peptide comprising any one of the defined regions may also be comprised within a larger peptide.

Exemplary Third Peptides (Type B Influenza HA)

In some embodiments, a third peptide may comprise a region having at least 85%, 90%, 95% or 99% homology with at least 20 contiguous amino acids from positions 2-49 or 68-121 of SEQ ID NO. 18. In some embodiments, a third peptide may comprise a region having at least 80% homology with at least 25, 30, 35, 40 or 45 contiguous amino acids from positions 2-49 or 68-121 of SEQ ID NO. 18.

In some embodiments, a third peptide may comprise a region having at least 80% homology with the entire sequence of SEQ ID NO. 12 (see Table 12). In some embodiments, the level of homology may be at least 85%, 90%, 95% or 99%. In some embodiments, a third peptide may comprise the entire sequence of SEQ ID NO. 12. In some embodiments, a third peptide may consist essentially of SEQ ID NO. 12. In some embodiments, a third peptide may consist of SEQ ID NO. 12.

In some embodiments, a third peptide may comprise a region having at least 80% homology with the entire sequence of SEQ ID NO. 13 (see Table 12). In some embodiments, the level of homology may be at least 85%, 90%, 95% or 99%. In some embodiments, a third peptide may comprise the entire sequence of SEQ ID NO. 13. In some embodiments, a third peptide may consist essentially of SEQ ID NO. 13. In some embodiments, a third peptide may consist of SEQ ID NO. 13.

In some embodiments, a third peptide may comprise a first region having at least 80% homology with at least 20 contiguous amino acids from positions 2-49 and a second region having at least 80% homology with at least 20 contiguous amino acids from positions 68-121 of SEQ ID NO. 18. In some embodiments, the homology may be higher, e.g., at least 85%, 90%, 95% or 99%. In some embodiments, the homology in the first and/or second region may span at least 25, 20, 35, 40 or 45 contiguous amino acids from positions 2-49 or 68-121 of SEQ ID NO. 18.

In some embodiments, a third peptide may comprise a region having at least 80% homology with the entire sequence of SEQ ID NO. 8. In some embodiments, the level of homology may be at least 85%, 90%, 95% or 99%. In some embodiments, a third peptide may comprise the entire sequence of SEQ ID NO. 8. In other embodiments, a third peptide may consist essentially of or consist of the sequence of SEQ ID NO. 8.

In some embodiments, an immunogenic composition may include two different third peptides one of which comprises a region having at least 80% homology with at least 20 contiguous amino acids from positions 2-49 of SEQ ID NO. 18 while the other comprises a region having at least 80% homology with at least 20 contiguous amino acids from positions 68-121 of SEQ ID NO. 18. In some embodiments, the level of homology may be at least 85%, 90%, 95% or 99% in one or both of the peptides.

In some embodiments, any of the aforementioned third peptides may comprise fewer than 100 amino acids, e.g., fewer than 90, 80, 70, 60, 50 or 40 amino acids. However, as discussed herein, in some embodiments, a third peptide comprising any one of the defined regions may also be comprised within a larger peptide.

Exemplary Fourth Peptides (Type A Influenza NP)

In some embodiments, an optional fourth peptide may comprise a sequence of SEQ ID NO. 14 (see Table 13). It will be appreciated that any one of the variant sequences described by the consensus sequence of SEQ ID NO. 14 is encompassed. The present application also provides immunogenic compositions which comprise two or more of these fourth peptides. Thus, in some embodiments, an immunogenic composition may comprise 2, 3, 4, 5, 6, 7, 8, 9, 10, 11, 12, 13, 14, 15 or 16 different fourth peptides that comprise a sequence of SEQ ID NO. 14. In some embodiments, an immunogenic composition may comprise $2^n$ different fourth peptides each comprising a different amino acid sequence of SEQ ID NO. 14, where n=1-4. In some embodiments, n=1. In some embodiments, n=2. In some embodiments, n=3. In some embodiments, n=4. It is to be understood that the immunogenic composition may also include fourth peptides which consist essentially of or consist of an amino acid sequence of SEQ ID NO. 14.

In some embodiments, an optional fourth peptide may comprise a sequence of SEQ ID NO. 15 (see Table 14). It will be appreciated that any one of the variant sequences described by the consensus sequence of SEQ ID NO. 15 is encompassed. The present application also provides immunogenic compositions which comprise two or more of these fourth peptides. Thus, in some embodiments, an immunogenic composition may comprise 2, 3, 4, 5, 6, 7, 8, 9, 10, 11, 12, 13, 14, 15 or 16 different fourth peptides that comprise a sequence of SEQ ID NO. 15. In some embodiments, an immunogenic composition may comprise $2^n$ different fourth peptides each comprising a different amino acid sequence of SEQ ID NO. 15, where n=1-4. In some embodiments, n=1. In some embodiments, n=2. In some embodiments, n=3. In some embodiments, n=4. It is to be understood that the immunogenic composition may also include fourth peptides which consist essentially of or consist of an amino acid sequence of SEQ ID NO. 15.

In some embodiments, any of the aforementioned fourth peptides may comprise fewer than 30 amino acids. However, as discussed herein, in some embodiments, a fourth peptide comprising any one of the defined regions may also be comprised within a larger peptide.

Exemplary Combinations of Peptides

In some embodiments, an immunogenic composition may include a first peptide which comprises a region having at least 80% homology with SEQ ID NO. 6, a third peptide which comprises a region having at least 80% homology with SEQ ID NO. 8 and $2^n$ different second peptides each comprising a different amino acid sequence of SEQ ID NO. 9, 10 or 11, where n=1-4. In one embodiment the second peptides each comprise a different amino acid sequence of SEQ ID NO. 11. In one embodiment n=4. In one embodiment, the composition further comprises $2^m$ different fourth peptides each comprising a different amino acid sequence of SEQ ID NO. 14, where m=1-4. In one embodiment, the composition further comprises $2^m$ different fourth peptides each comprising a different amino acid sequence of SEQ ID NO. 15, where m=1-4. In one embodiment m=4.

In some embodiments, an immunogenic composition may include a first peptide which comprises a region having at least 90% homology with SEQ ID NO. 6, a third peptide which comprises a region having at least 90% homology with SEQ ID NO. 8 and $2^n$ different second peptides each comprising a different amino acid sequence of SEQ ID NO. 9, 10 or 11, where n=1-4. In one embodiment the second peptides each comprise a different amino acid sequence of SEQ ID NO. 11. In one embodiment n=4. In one embodiment, the composition further comprises $2^m$ different fourth peptides each comprising a different amino acid sequence of SEQ ID NO. 14, where m=1-4. In one embodiment, the composition further comprises $2^m$ different fourth peptides each comprising a different amino acid sequence of SEQ ID NO. 15, where m=1-4. In one embodiment m=4.

In some embodiments, an immunogenic composition may include a first peptide which comprises a region having at least 95% homology with SEQ ID NO. 6, a third peptide which comprises a region having at least 95% homology with SEQ ID NO. 8 and $2^n$ different second peptides each comprising a different amino acid sequence of SEQ ID NO. 9, 10 or 11, where n=1-4. In one embodiment the second peptides each comprise a different amino acid sequence of SEQ ID NO. 11. In one embodiment n=4. In one embodiment, the composition further comprises $2^m$ different fourth peptides each comprising a different amino acid sequence of SEQ ID NO. 14, where m=1-4. In one embodiment, the composition further comprises $2^m$ different fourth peptides each comprising a different amino acid sequence of SEQ ID NO. 15, where m=1-4. In one embodiment m=4.

In some embodiments, an immunogenic composition may include a first peptide which comprises SEQ ID NO. 6, a third peptide which comprises SEQ ID NO. 8 and $2^n$ different second peptides each comprising a different amino acid sequence of SEQ ID NO. 9, 10 or 11, where n=1-4. In one embodiment the second peptides each comprise a different amino acid sequence of SEQ ID NO. 11. In one embodiment n=4. In one embodiment, the composition further comprises $2^m$ different fourth peptides each comprising a different amino acid sequence of SEQ ID NO. 14, where m=1-4. In one embodiment, the composition further comprises $2^m$ different fourth peptides each comprising a different amino acid sequence of SEQ ID NO. 15, where m=1-4. In one embodiment m=4.

In some embodiments, an immunogenic composition may include a first peptide which consists essentially of SEQ ID NO. 6, a third peptide which consists essentially of SEQ ID NO. 8 and $2^n$ different second peptides each consisting essentially of a different amino acid sequence of SEQ ID NO. 9, 10 or 11, where n=1-4. In one embodiment the second peptides each consist essentially of a different amino acid sequence of SEQ ID NO. 11. In one embodiment n=4. In one embodiment, the composition further comprises $2^m$ different fourth peptides each consisting essentially of a different amino acid sequence of SEQ ID NO. 14, where m=1-4. In one embodiment, the composition further comprises $2^m$ different fourth peptides each consisting essentially of a different amino acid sequence of SEQ ID NO. 15, where m=1-4. In one embodiment m=4.

In some embodiments, an immunogenic composition may include a first peptide which consists of SEQ ID NO. 6, a third peptide which consists of SEQ ID NO. 8 and $2^n$ different second peptides each consisting of a different amino acid sequence of SEQ ID NO. 9, 10 or 11, where n=1-4. In one embodiment the second peptides each consist of a different amino acid sequence of SEQ ID NO. 11. In one embodiment n=4. In one embodiment, the composition further comprises $2^m$ different fourth peptides each consisting of a different amino acid sequence of SEQ ID NO. 14, where m=1-4. In one embodiment, the composition further comprises $2^m$ different fourth peptides each consisting of a different amino acid sequence of SEQ ID NO. 15, where m=1-4. In one embodiment m=4.

III. Peptide Synthesis

Peptides that are described herein may be synthesized using any known method in the art (including recombinant methods). In various embodiments, peptides may be synthesized by solid phase peptide synthesis (SPPS). In SPPS, the C-terminal amino acid is attached to a solid phase (typically a cross-linked resin such as a polystyrene or polyethylene glycol-containing resin) via an acid labile bond with a linker molecule. The solid phase used is generally insoluble in the solvents used for synthesis, making it relatively simple and fast to wash away excess reagents and by-products. The N-terminus is protected with a protecting group (e.g., an Fmoc group) which is stable in acid, but removable by base. Side chain functional groups are protected with base stable, acid labile groups. The SPSS technique then involves incorporating N-α-protected amino acids into the growing peptide chain while the C-terminus remains attached to the solid phase. Example 1 describes an exemplary SPSS process In general, this process can be automated and commercially available equipment can be used to routinely synthesize peptides of twenty or more amino acids in length. When preparing long peptides (e.g., longer than forty amino acids) it may prove advantageous to generate the peptide in a series of fragment that can be ligated by using appropriate protective groups.

As described herein, certain peptide compositions can include multiple variants of a single peptide sequence (e.g., with 2 or more different amino acids at 2 or more positions in the same sequence). While each variant in a given set could be synthesized individually, it will typically be advantageous to synthesize a subset or the entire set of variants in a single synthesis. In various embodiments, this can be achieved using a split-combine method. Thus, if the set of variants has been designed to include one of two different amino acids at a given position, the resin can be split into two equal parts and each part can be coupled with one of the two amino acids to form two distinctive peptide chains. Once the coupling has been completed the two parts can be recombined so that the subsequent amino acid can be added to both chains. Alternatively, a one-pot method may be used wherein the two alternative amino acids are added to the same reaction. Typically the two amino acids will be added in equimolar amounts; however in certain circumstances (e.g., if their respective reaction kinetics differ significantly) non-equimolar amounts may be preferred. The peptide reaction can then be monitored for completeness using a Kaiser ninhydrin test.

The following references describe some exemplary methods for preparing peptide mixtures: Houghten, *Proc. Natl. Acad. Sci. USA* 82:5131 (1985); Geysen et al, *Proc. Natl. Acad. Sci. USA* 81:3998 (1984) and U.S. Pat. No. 5,010,175.

IV. Adjuvants

In some embodiments, immunogenic compositions may include one or more adjuvants. As is well known in the art, adjuvants are agents that enhance immune responses. Adjuvants are well known in the art (e.g., see "Vaccine Design: The Subunit and Adjuvant Approach", *Pharmaceutical Biotechnology*, Volume 6, Eds. Powell and Newman, Plenum Press, New York and London, 1995).

Exemplary adjuvants include complete Freund's adjuvant (CFA), incomplete Freund's adjuvant (IFA), squalene, squalane and alum (aluminum hydroxide), which are materials well known in the art, and are available commercially from several sources. In some embodiments, aluminum or calcium salts (e.g., hydroxide or phosphate salts) may be used as adjuvants. Alum (aluminum hydroxide) has been used in many existing vaccines. Typically, about 40 to about 700 μg of aluminum can be included per dose.

In various embodiments, oil-in-water emulsions or water-in-oil emulsions can also be used as adjuvants. For example, the oil phase may include squalene or squalane and a surfactant. In various embodiments, non-ionic surfactants such as the mono- and di-$C_{12}$-$C_{24}$-fatty acid esters of sorbitan and mannide may be used. The oil phase preferably comprises about 0.2 to about 15% by weight of the immunogenic peptide(s) (e.g., about 0.2 to 1%). PCT Publication No. WO 95/17210 describes exemplary emulsions.

The adjuvant designated QS21 is an immunologically active saponin fractions having adjuvant activity derived from the bark of the South American tree *Quillaja Saponaria* Molina, and the method of its production is disclosed in U.S. Pat. No. 5,057,540. Semi-synthetic and synthetic derivatives of *Quillaja Saponaria* Molina saponins are also useful, such as those described in U.S. Pat. Nos. 5,977,081 and 6,080,725.

TLRs are a family of proteins homologous to the Drosophila Toll receptor, which recognize molecular patterns associated with pathogens and thus aid the body in distinguishing between self and non-self molecules. Substances common in viral pathogens are recognized by TLRs as pathogen-associated molecular patterns. For example, TLR-3 recognizes patterns in double-stranded RNA, TLR-4 recognizes patterns in lipopolysaccharides while TLR-7/8 recognize patterns containing adenosine in viral and bacterial RNA and DNA. When a TLR is triggered by such pattern recognition, a series of signaling events occurs that leads to inflammation and activation of innate and adaptive immune responses. A number of synthetic ligands containing the molecular patterns recognized by various TLRs are being developed as adjuvants and may be included in an immunogenic composition as described herein.

For example, polyriboinosinic:polyribocytidylic acid or poly(I:C) (available from InvivoGen of San Diego, Calif.) is a synthetic analog of double-stranded RNA (a molecular pattern associated with viral infection) and an exemplary adjuvant that is an agonist for TLR-3 (e.g., see Field et al., *Proc. Natl. Acad. Sci. USA* 58:1004 (1967) and Levy et al., *Proc. Natl. Acad. Sci. USA* 62:357 (1969)). Example 11 below demonstrates the benefits of using this adjuvant with an exemplary oral peptide composition. In some embodiments, poly(I:C) may be combined with other agents to improve stability (e.g., by reducing degradation via the activity of RNAses). For example, U.S. Pat. Nos. 3,952,097, 4,024,241 and 4,349,538 describe poly(I:C) complexes with poly-L-lysine. The addition of poly-arginine to poly(I:C) has also been shown to reduce degradation via the activity of RNAses. U.S. Patent Publication No. 20090041809 describes double-stranded nucleic acids with one or more than one locked nucleic acid (LNA) nucleosides that can act as TLR-3 agonists. Those skilled in the art will be able to identify other suitable TLR-3 agonist adjuvants.

Attenuated lipid A derivatives (ALD) such as monophosphoryl lipid A (MPL) and 3-deacyl monophosphoryl lipid A (3D-MPL) are exemplary adjuvants that are agonists for TLR-4. ALDs are lipid A-like molecules that have been altered or constructed so that the molecule displays lesser or different of the adverse effects of lipid A. These adverse effects include pyrogenicity, local Shwarzman reactivity and toxicity as evaluated in the chick embryo 50% lethal dose assay ($CELD_{50}$). MPL and 3D-MPL are described in U.S. Pat. Nos. 4,436,727 and 4,912,094, respectively. MPL was originally derived from lipid A, a component of enterobacterial lipopolysaccharides (LPS), a potent but highly toxic immune system modulator. 3D-MPL differs from MPL in that the acyl residue that is ester linked to the reducing-end glucosamine at position 3 has been selectively removed. It will be appreciated that MPL and 3D-MPL may include a mixture of a number of fatty acid substitution patterns, i.e., heptaacyl, hexaacyl, pentaacyl, etc., with varying fatty acid chain lengths. Thus, various forms of MPL and 3D-MPL, including mixtures thereof, are encompassed by the present disclosure.

Figure 13:
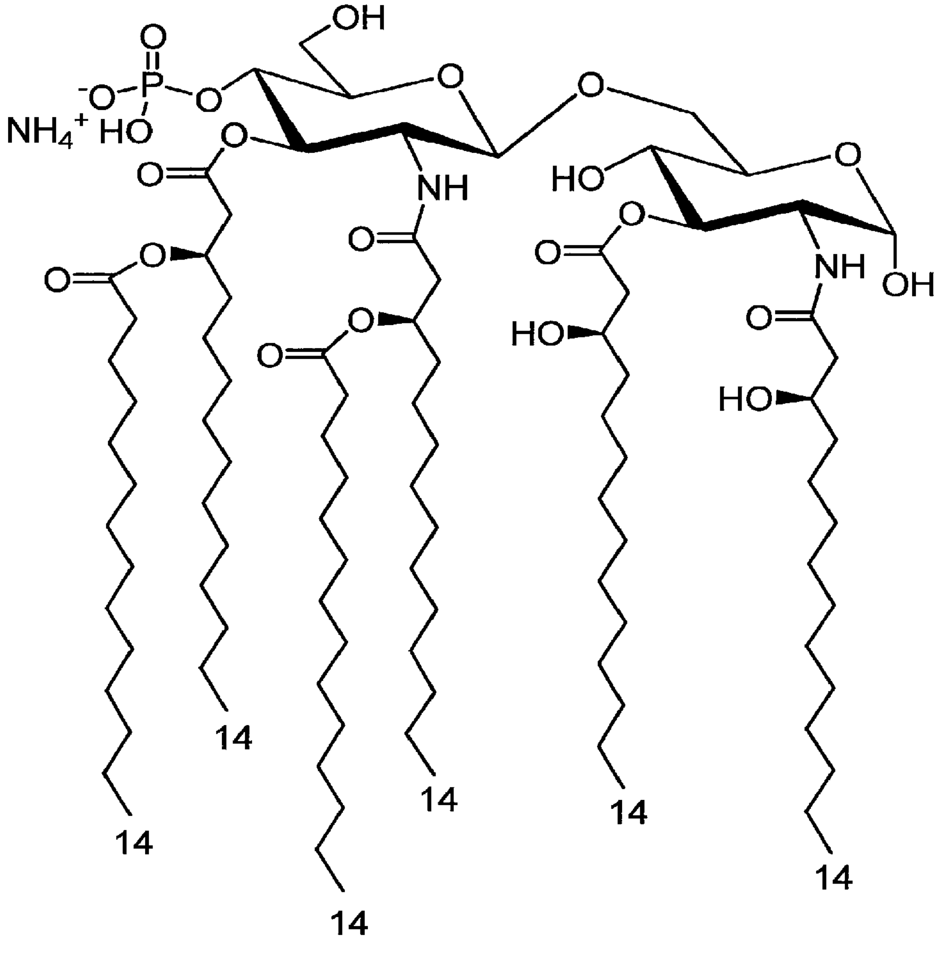
FIG. 13 shows the chemical structure of the examplary TLR-4 agonist adjuvant PHAD (phosphorylated hexaacyl disaccharide from Avanti Polar Lipids, Inc. of Alabaster, Ala.).
Figure 14:
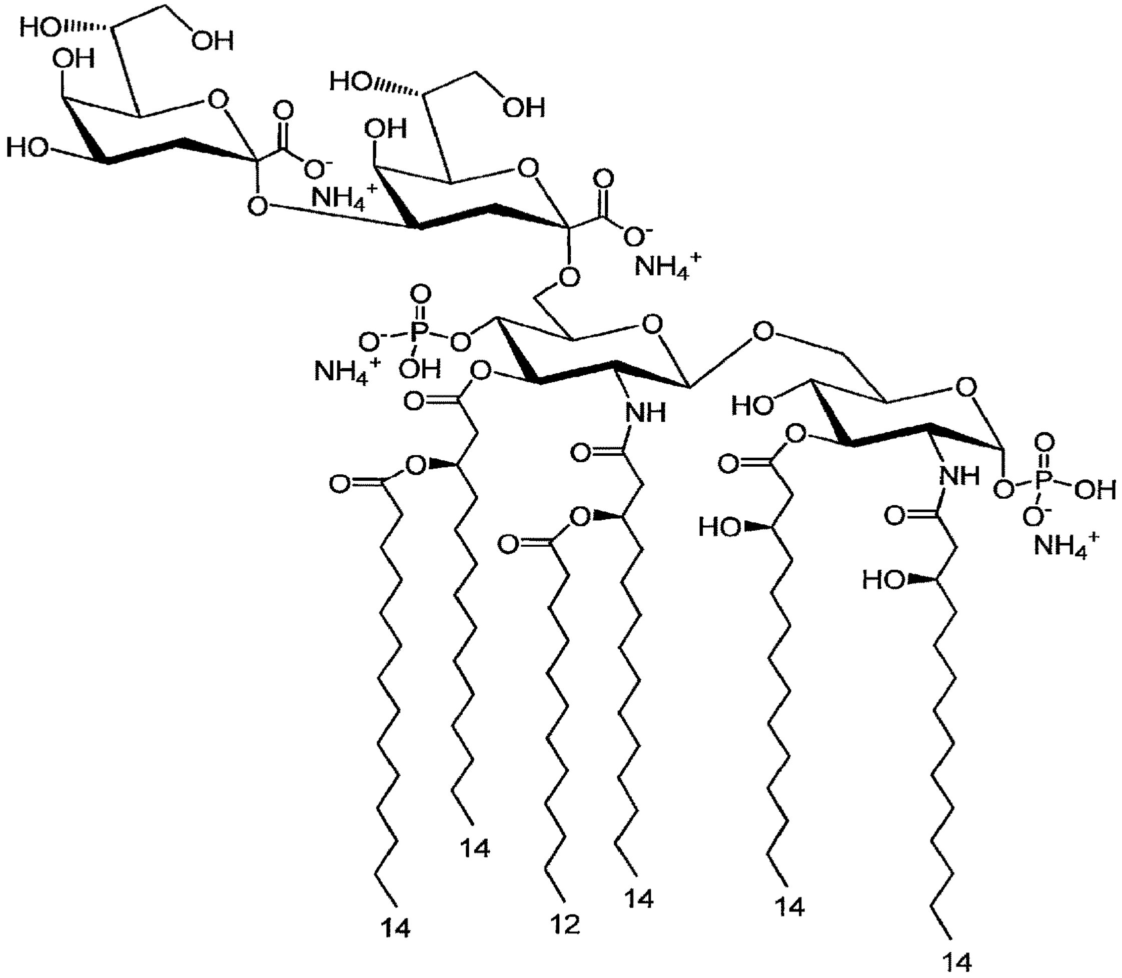
FIG. 14 shows the chemical structure of di[3-deoxy-D-manno-octulosonyl]-lipid A (ammonium salt) another exemplary TLR-4 agonist adjuvant (from Avanti Polar Lipids, Inc. of Alabaster, Ala.).

In some embodiments these ALDs may be combined with trehalosedimycolate (TDM) and cell wall skeleton (CWS), e.g., in a 2% squalene/Tween™ 80 emulsion (e.g., see GB Patent No. 2122204). MPL is available from Avanti Polar Lipids, Inc. of Alabaster, Ala. as PHAD (phosphorylated hexaacyl disaccharide). FIG. 13 shows a chemical structure of PHAD. Example 13 below demonstrates the benefits of using this adjuvant with an exemplary parenteral peptide composition. The structure of di[3-deoxy-D-manno-octulosonyl]-lipid A (ammonium salt) another exemplary TLR-4 agonist adjuvant is shown in FIG. 14 (also from Avanti Polar Lipids, Inc. of Alabaster, Ala.). Those skilled in the art will be able to identify other suitable TLR-4 agonist adjuvants. For example, other lipopolysaccharides have been described in WO 98/01139; U.S. Pat. No. 6,005,099 and EP Patent No. 729473.

Imiquimod (1-isobutyl-1H-imidazo[4,5-c]quinolin-4-amine) is a small molecule agonist of TLR-7/8 which may also be advantageously included in an immunogenic composition as described herein.

V. Vesicles

In some embodiments, one or more peptides in a composition may be combined with a vesicle. As is well known in the art, vesicles generally have an aqueous compartment enclosed by one or more bilayers which include amphipathic molecules (e.g., fatty acids, lipids, steroids, etc.). The one or more peptides may be present in the aqueous core of the vesicle. Depending on its hydrophobicity, a peptide may also be associated with a bilayer (e.g., through hydrophobic interactions and/or hydrogen or ionic bonds). It is to be understood that any vesicle may be used with an immunogenic composition as described herein and that the amphipathic molecules of the bilayer may be ionic and/or non-ionic.

In some embodiments, the vesicle may comprise a non-ionic amphiphile (e.g., a non-ionic surfactant). Any non-ionic surfactant with appropriate amphipathic properties may be used to form such a vesicle. Without limitation, examples of suitable surfactants include ester-linked surfactants based on glycerol. Such glycerol esters may comprise one of two higher aliphatic acyl groups, e.g., containing at least ten carbon atoms in each acyl moiety. Surfactants based on such glycerol esters may comprise more than one glycerol unit, e.g., up to 5 glycerol units. Glycerol monoesters may be used, e.g., those containing a $C_{12}$-$C_{20}$alkanoyl or alkenoyl moiety, for example caproyl, lauroyl, myristoyl, palmitoyl, oleyl or stearoyl. An exemplary surfactant is 1-monopalmitoyl glycerol.

Ether-linked surfactants may also be used as the non-ionic surfactant. For example, ether-linked surfactants based on glycerol or a glycol having a lower aliphatic glycol of up to 4 carbon atoms, such as ethylene glycol, are suitable. Surfactants based on such glycols may comprise more than one glycol unit, e.g., up to 5 glycol units (e.g., diglycolcetyl ether and/or polyoxyethylene-3-lauryl ether). Glycol or glycerol monoethers may be used, including those containing a $C_{12}$-$C_{20}$alkanyl or alkenyl moiety, for example capryl, lauryl, myristyl, cetyl, oleyl or stearyl. Ethylene oxide condensation products that can be used include those disclosed in PCT Publication No. WO88/06882 (e.g., polyoxyethylene higher aliphatic ether and amine surfactants). Exemplary ether-linked surfactants include 1-monocetyl glycerol ether and diglycolcetyl ether.

In some embodiments, a vesicle comprising a non-ionic surfactant may further comprise an ionic amphiphile, e.g., to cause the vesicles to take on a negative charge. For example, this may help to stabilize the vesicle and provide effective dispersion. Without limitation, acidic materials such as higher alkanoic and alkenoic acids (e.g., palmitic acid, oleic acid) or other compounds containing acidic groups including phosphates such as dialkyl phosphates (e.g., dicetylphosphate, or phosphatidic acid or phosphatidyl serine) and sulphate monoesters such as higher alkyl sulphates (e.g., cetylsulphate), may all be used for this purpose. The ionic amphiphile, if present, will typically comprise, between 1 and 30% by weight of the non-ionic surfactant. For example, between 2 and 20% by weight or between 5 and 15% by weight.

In some embodiments, the vesicle components may be admixed with an appropriate hydrophobic material of higher molecular mass capable of forming a bi-layer (such as a steroid, e.g., a sterol such as cholesterol). In some embodiments, the presence of the steroid may assist in forming the bi-layer on which the physical properties of the vesicle depend. The steroid, if present, will typically comprise between 20 and 120% by weight of the non-ionic surfactant. For example, between 25 and 90% by weight or between 35 and 75% by weight.

In some embodiments, the vesicle may be a bilosome (see, e.g., U.S. Pat. No. 5,876,721). As used herein, "bilosomes" are vesicles that comprise non-ionic surfactants and transport enhancing molecules which facilitate the transport of lipid-like molecules across mucosal membranes. As described in U.S. Pat. No. 5,876,721, a variety of molecules may be used as transport enhancers. For example, cholesterol derivatives in which the $C_{23}$ carbon atom of the side chain carries a carboxylic acid, and/or derivatives thereof, may be used as transport enhancers. Such derivatives include, but are not limited to, the "bile acids" cholic acid and chenodeoxycholic acid, their conjugation products with glycine or taurine such as glycocholic and taurocholic acid, derivatives including deoxycholic and ursodeoxycholic acid, and salts of each of these acids.

Other transport enhancers include acyloxylated amino acids, such as acylcarnitines and salts thereof. For example, acylcarnitine containing $C_{6-20}$alkanoyl or alkenoyl moieties, such as palmitoylcarnitine, may be used as transport enhancers. As used herein, the term acyloxylated amino acid is intended to cover primary, secondary and tertiary amino acids as well as α, β, and γ amino acids. Acylcarnitines are examples of acyloxylated γ amino acids.

It is to be understood that bilosomes which are included in an immunogenic composition may comprise more than one type of transport enhancer, e.g., one or more different bile salts and one or more acylcarnitines.

It is also to be understood that bilosomes may also incorporate an ionic amphiphile, e.g., to cause the bilosomes to take on a negative charge. For example, this may help to stabilize the bilosomes and provide effective dispersion. Without limitation, acidic materials such as higher alkanoic and alkenoic acids (e.g., palmitic acid, oleic acid) or other compounds containing acidic groups including phosphates such as dialkyl phosphates (e.g., dicetylphosphate, or phosphatidic acid or phosphatidyl serine) and sulphate monoesters such as higher alkyl sulphates (e.g., cetylsulphate), may all be used for this purpose.

In some embodiments, the bilosome components may be admixed with an appropriate hydrophobic material of higher molecular mass capable of forming a bi-layer (such as a steroid, e.g., a sterol such as cholesterol). In some embodiments, the presence of the steroid may assist in forming the bi-layer on which the physical properties of the bilosome depend.

The transport enhancer(s) present within the bilosomes will generally be present in amount of between 40 and 400% percent by weight of the non-ionic surfactant (e.g., between 60 and 100% by weight or between 70 and 90% by weight). The steroid, if present, will typically comprise between 20 and 120% by weight of the non-ionic surfactant (e.g., between 25 and 90% by weight or between 35 and 75% by weight). The ionic amphiphile, if present, will typically comprise, between 1 and 30% by weight of the non-ionic surfactant (e.g., between 2 and 20% by weight or between 5 and 15% by weight).

There are many known techniques for preparing vesicles comprising non-ionic surfactants, e.g., those referred to in PCT Publication No. WO1993/019781. It will be appreciated that any of these known methods may be used to prepare suitable vesicles and that bilosomes may be prepared by modifying any of these techniques. An exemplary technique is the rotary film evaporation method, in which a film of non-ionic surfactant is prepared by rotary evaporation from an organic solvent, e.g., a hydrocarbon or chlorinated hydrocarbon solvent such as chloroform, e.g., see Russell and Alexander, *J. Immunol.* 140:1274 (1988). The resulting thin film is then rehydrated in bicarbonate buffer in the presence of the transport enhancer.

Another method for the production of vesicles that can be adapted for preparation of bilosomes is that disclosed by Collins et al., *J. Pharm. Pharmacol.* 42:53 (1990). This method involves melting a mixture of the non-ionic surfactant, steroid (if used) and ionic amphiphile (if used) and hydrating with vigorous mixing in the presence of aqueous buffer. The transport enhancer can be incorporated into the vesicles, either by being included with the other constituents in the melted mixture (i.e., by co-melting) or concomitantly during the process used to entrap the peptides.

Another method involves hydration in the presence of shearing forces. An apparatus that can be used to apply such shearing forces is a well known, suitable equipment (see, e.g., PCT Publication No. WO88/06882). Sonication and ultra-sonication are also effective means to form the vesicles or to alter their particle size.

The one or more peptides may be combined with vesicles in any manner. For example, in the rotary film evaporation technique, this can be achieved by hydration of the film in the presence of peptides together with the transport enhancer. In other methods, the one or more peptides may be combined with preformed vesicles by a dehydration-rehydration method in which peptides present in the aqueous phase are entrapped by flash freezing followed by lyophilisation, e.g., see Kirby and Gregoriadis, *Biotechnology* 2:979 (1984). Alternatively a freeze thaw technique may be used in which vesicles are mixed with the peptides and repeatedly flash frozen in liquid nitrogen, and warmed to a temperature of the order of, e.g., 60° C. (i.e., above the transition temperature of the relevant surfactant), e.g., see Pick, *Arch. Biochem. Biophys.* 212:195 (1981). In addition to entrapping peptides, the dehydration-rehydration method and freeze-thaw technique are also capable of concomitantly incorporating additional transport enhancers into the vesicles.

In each of these methods, the suspension of vesicle components may be extruded several times through microporous polycarbonate membranes at an elevated temperature sufficient to maintain the vesicle-forming mixture in a molten condition. This has the advantage that vesicles having a uniform size may be produced. Vesicles (including bilosomes) that may be used in accordance with the invention may be of any diameter. In some embodiments, the composition may include vesicles with diameters in the range of about 10 nm to about 10 μm. In some embodiments, vesicles are of diameters between about 100 nm to about 5 μm. In some embodiments, vesicles are of diameters between about 500 nm to about 2 μm. In some embodiments, vesicles are of diameters between about 800 nm to about 1.5 μm.

VI. Dosage and Administration

The methods of this invention are useful for treating influenza in humans including adults and children. In general however they may be used with any animal. In some embodiments, the methods herein may be used for veterinary applications, e.g., canine and feline applications. If desired, the methods herein may also be used with farm animals, such as ovine, avian, bovine, porcine and equine breeds.

Compositions described herein will generally be administered in such amounts and for such a time as is necessary or sufficient to induce an immune response. Dosing regimens may consist of a single dose or a plurality of doses over a period of time. The exact amount of a peptide composition to be administered may vary from subject to subject and may depend on several factors. Thus, it will be appreciated that, in general, the precise dose used will be as determined by the prescribing physician and will depend not only on the weight of the subject and the route of administration, but also on the age of the subject and the severity of the symptoms and/or the risk of infection. In some embodiments, the dose of peptide in an immunogenic composition may range from about 0.01 to 50 mg. For example, in some embodiments the range may be between 0.1 and 5 mg, e.g., between 0.1 and 2 mg. Example 14 describes exemplary administration schemes that involve two consecutive intramuscular injections of 0.2 or 1 mg peptide doses (on Day 0 and Day 28).

In general, the compositions may be administered to a subject by any route. The results in the Examples demonstrate that the immunogenic peptide compositions described herein can induce a protective response when administered via the traditional parenteral route but also orally. Thus, in some embodiments, the compositions may be administered orally (including buccally, sublingually and by gastric lavage or other artificial feeding means). Such oral delivery may be accomplished using solid or liquid compositions, for example in the form of tablets, capsules, multi-particulates, gels, films, ovules, elixirs, solutions, suspensions, etc. In some embodiments, when using a liquid composition, the composition may be administered in conjunction with a basic composition (e.g., a bicarbonate solution) in order to neutralize the stomach pH. In some embodiments, the basic composition may be administered before and/or after the peptide composition. In some embodiments, the basic composition may be combined with the peptide composition prior to administration or taken at the same time as the peptide composition.

It will be appreciated that the oral route is particularly desirable in light of the advantages of oral delivery over any form of injection. It will also be appreciated that the results are surprising in light of the fact that all known influenza vaccines have so far been administered parenterally. The ability to induce a protective response by oral delivery is particularly unexpected in light of the fact that the immunogenic compositions described herein include peptides that are much shorter than the standard protein antigens that are used in current influenza vaccines. Indeed, there has long been a prejudice in the art against both the use of short peptides as immunogens and oral delivery of protein vaccines.

In some embodiments, oral compositions comprise one or more peptides, bilosomes and an adjuvant. In some embodiments, the adjuvant is a TLR-3 agonist. In some embodiments, the adjuvant may be mixed with the bilosomes. In some embodiments, the adjuvant may be associated with the bilosomes (e.g., by incorporating the adjuvant with the one or more peptides and/or bilosome components during the process used to make the bilosomes).

In some embodiments, the compositions may be formulated for delivery parenterally, e.g., by injection. In such embodiments, administration may be, for example, intravenous, intramuscular, intradermal, or subcutaneous, or via by infusion or needleless injection techniques. For such parenteral administration, the compositions may be prepared and maintained in conventional lyophylized compositions and reconstituted prior to administration with a pharmaceutically acceptable saline solution, such as a 0.9% saline solution. The pH of the injectable composition can be adjusted, as is known in the art, with a pharmaceutically acceptable acid, such as methanesulfonic acid. Other acceptable vehicles and solvents that may be employed include Ringer's solution and U.S.P. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable compositions can be sterilized, for example, by filtration through a bacterial-retaining filter, or by incorporating sterilizing agents in the form of sterile solid compositions which can be dissolved or dispersed in sterile water or other sterile injectable medium prior to use.

In some embodiments, parenteral compositions comprise one or more peptides, vesicles that comprise non-ionic surfactants and an adjuvant. In some embodiments, the adjuvant is a TLR-4 agonist. In some embodiments, the adjuvant may be mixed with the vesicles. In some embodiments, the adjuvant may be associated with the vesicles (e.g., by incorporating the adjuvant with the one or more peptides and/or vesicle components during the process used to make the vesicles).

The compositions can also be administered intranasally or by inhalation and are conveniently delivered in the form of a dry powder inhaler or an aerosol spray presentation from a pressurized container, pump, spray, atomiser or nebuliser, with or without the use of a suitable propellant, e.g., dichlorodifluoromethane, trichlorofluoromethane, dichlorotetrafluoroethane, a hydrofluoroalkane, carbon dioxide or other suitable gas. In the case of a pressurized aerosol, the dosage unit may be determined by providing a valve to deliver a metered amount. The pressurized container, pump, spray, atomiser or nebuliser may contain a solution or suspension of the antibody, e.g., using a mixture of ethanol and the propellant as the solvent, which may additionally contain a lubricant, e.g., sorbitantrioleate. Capsules and cartridges (made, for example, from gelatin) for use in an inhaler or insufflator may be formulated to contain a powder mix of the peptide composition and a suitable powder base such as lactose or starch.

Compositions for rectal administration are preferably suppositories which can be prepared by mixing the peptide(s) with suitable non-irritating excipients or carriers such as cocoa butter, polyethylene glycol or a suppository wax which are solid at ambient temperature but liquid at body temperature and therefore melt in the rectal vault and release the antibodies. Retention enemas and rectal catheters can also be used as is known in the art. Viscosity-enhancing carriers such as hydroxypropyl cellulose are also certain carriers of the invention for rectal administration since they facilitate retention of the composition within the rectum. Generally, the volume of carrier that is added to the composition is selected in order to maximize retention of the composition. In particular, the volume should not be so large as to jeopardize retention of the administered composition in the rectal vault.

VII. Exemplary Compositions

In some embodiments, the present disclosure provides immunogenic compositions that include a TLR-3 agonist adjuvant and a vesicle which comprises a non-ionic surfactant and a transport enhancer which facilitates the transport of lipid-like molecules across mucosal membranes. In some embodiments, these compositions may be administered orally. In some embodiments the TLR-3 agonist adjuvant comprises poly(I:C). In some embodiments, the transport enhancer is a bile acid, a derivative thereof or a salt of any of these (e.g., sodium deoxycholate). In some embodiments, the non-ionic surfactant is a glycerol ester (e.g., 1-monopalmitoyl glycerol). In some embodiments, the vesicle further comprises an ionic amphiphile (e.g., dicetylphosphate). In some embodiments, the vesicle further comprises a steroid (e.g., cholesterol). In some embodiments, the vesicles comprise 1-monopalmitoyl glycerol, dicetylphosphate, cholesterol and sodium deoxycholate. In some embodiments, the composition further comprises alum.

In some embodiments, the present disclosure provides immunogenic compositions that include a TLR-4 agonist adjuvant and a vesicle which comprises a non-ionic surfactant. In some embodiments, these compositions may be administered parenterally (e.g., by intramuscular injection). In some embodiments the TLR-4 agonist adjuvant comprises monophosphoryl lipid A or 3-deacyl monophosphoryl lipid A. In some embodiments, the non-ionic surfactant is a glycerol ester (e.g., 1-monopalmitoyl glycerol). In some embodiments, the vesicle further comprises an ionic amphiphile (e.g., dicetylphosphate). In some embodiments, the vesicle further comprises a steroid (e.g., cholesterol). In some embodiments, the vesicles comprise 1-monopalmitoyl glycerol, dicetylphosphate and cholesterol. In some embodiments, the composition further comprises alum.

In some embodiments, the aforementioned immunogenic compositions include a first peptide comprising a region having at least 80% homology with 20-100 contiguous amino acids of SEQ ID NO. 16, wherein the first peptide includes fewer than 100 contiguous amino acids from a type A influenza hemagglutinin protein; a second peptide comprising an amino acid sequence of SEQ ID NO. 17; a third peptide comprising a region having at least 80% homology with at least 20 contiguous amino acids from positions 2-49 or 68-121 of SEQ ID NO. 18, wherein the third peptide includes fewer than 100 contiguous amino acids from a type B influenza hemagglutinin protein; and a fourth peptide comprising an amino acid sequence of SEQ ID NO. 14, wherein the fourth peptide includes fewer than 20 contiguous amino acids from a type A influenza nucleoprotein.

In some embodiments, the first peptide comprises at least 40 contiguous amino acids of SEQ ID NO. 6. In some embodiments, the first peptide comprises amino acids 1-88 of SEQ ID NO. 6.

In some embodiments, the second peptide comprises an amino acid sequence of SEQ ID NO. 11. In some embodiments the composition comprises $2^n$ different second peptides each comprising a different amino acid sequence of SEQ ID NO. 11, where n=1-4. In some embodiments n=4.

In some embodiments, the third peptide comprises a region having at least 90% homology with at least 20 contiguous amino acids from positions 2-49 or 68-121 of SEQ ID NO. 18. In some embodiments, the third peptide comprises a first region having at least 80% homology with at least 20 contiguous amino acids from positions 2-49 and a second region having at least 80% homology with at least 20 contiguous amino acids from positions 68-121 of SEQ ID NO. 18. In some embodiments the composition comprises two different third peptides, one of which comprises a region having at least 80% homology with at least 20 contiguous amino acids from positions 2-49 of SEQ ID NO. 18 while the other comprises a region having at least 80% homology with at least 20 contiguous amino acids from positions 68-121 of SEQ ID NO. 18. In some embodiments, the composition comprises two different third peptides, one of which comprises an amino acid sequence of SEQ ID NO. 12 while the other comprises an amino acid sequence of SEQ ID NO. 13.

In some embodiments, the composition comprises $2^n$ different fourth peptides each comprising a different amino acid sequence of SEQ ID NO. 14, where n=1-4. In some embodiments n=4.

In some embodiments, the first peptide comprises amino acids 1-88 of SEQ ID NO. 6; the composition comprises $2^n$ different second peptides each comprising a different amino acid sequence of SEQ ID NO. 11, where n=4; the composition comprises two different third peptides, one of which comprises an amino acid sequence of SEQ ID NO. 12 while the other comprises an amino acid sequence of SEQ ID NO. 13.; and the composition comprises $2^m$ different fourth peptides each comprising a different amino acid sequence of SEQ ID NO. 14, where m=4.

In some embodiments, the aforementioned compositions are used to treat an individual suffering from, or at risk for, seasonal influenza.

In some embodiments, the aforementioned compositions are used to treat an individual suffering from, or at risk for, influenza caused by an influenza A (H1N1) virus of swine origin.

EXAMPLES

The following examples describe some exemplary modes of making and practicing certain compositions and methods that are described herein. It should be understood that these examples are for illustrative purposes only and are not meant to limit the scope of the compositions and methods described herein.

Example 1

Peptide Synthesis

All peptides described herein were synthesized by solid phase peptide synthesis (SPPS). Generally, the C-terminal amino acid was attached to a cross-linked polystyrene (or PEG-based) resin via an acid labile bond with a linker molecule. This resin is insoluble in the solvents used for synthesis, making it relatively simple and fast to wash away excess reagents and by-products. The N-terminus was protected with an Fmoc group, which is stable in acid, but removable by base. Any side chain functional groups were protected with base stable, acid labile groups. The synthesis was then based on the incorporation of N-α-Fmoc protected amino acids into the growing peptide chain with one end of the chain remaining attached to the solid phase.

The following is an exemplary SPPS method that was used to make the peptides described herein. To begin each coupling, the Fmoc group on the NovaPEG resin bound amino acid/peptide was removed with 20% piperidine in N,N-dimethylformamide (DMF). It was then rinsed and a protected amino acid that had been activated at its α-carboxyl group by 2-(1H-Benzotriazole-1-yl)-1,1,3,3-tetramethyluronium tetrafluoroborate was added. The activated amino acid and the resin-bound amino acid were allowed to react in the presence of base to form a new peptide bond. While peptides were synthesized by stepwise method, all soluble reagents, such as the coupling reagent, 2-(1H-Benzotriazole-1-yl)-1,1,3,3-tetramethyluronium tetrafluoroborate (TBTU), base, diisopropylethyl amine (DIPEA) and de-blocking reagent, piperidine, were removed from the peptide-solid support matrix by filtration and rinsed at the end of each coupling step. This process was repeated until the desired peptide was assembled on the resin. After cleavage from the resin and deprotection of protective groups from the peptides by a cleavage solution containing at least 85% of Trifluoro acetic acid (TFA) a crude peptide was collected by precipitation from ether, followed by centrifugation. The peptides were then purified and characterized by HPLC and mass spectroscopy.

As described herein, certain peptide compositions can include multiple variants of a single peptide sequence (e.g., with 2 or more different amino acids at 2 or more positions in the same sequence). While each variant in a given set could be synthesized individually, it will typically be advantageous to synthesize a subset or the entire set of variants in a single synthesis. For example, this can be achieved using a split-combine method. Thus, if the set of variants has been designed to include one of two different amino acids at a given position, the resin can be split into two equal parts and each part can be coupled with one of the two amino acid to form two distinctive peptide chains. Once the coupling has been completed the two parts can be recombined so that the subsequent amino acid can be added to both chains. Alternatively, a one-pot method may be used wherein the two alternative amino acids are added to the same reaction. Typically the two amino acids will be added in equimolar amounts; however in certain circumstances (e.g., if their respective reaction kinetics differ significantly) non-equimolar amounts may be preferred. The peptide reaction can then be monitored for completeness using a Kaiser ninhydrin test.

Example 2

Competition Micro-Neutralization Assay

In the present Example, the ability of various peptide compositions to bind influenza neutralizing antibodies was assessed. Different peptide compositions (see FIG. 1 and Tables 1-9 below) were diluted at 80 μg/ml in Iscove's Modified Dulbecco's Medium (IMDM) and 50 μl was added to different wells in 96-well flat bottom microtitre plates (Nunc). Each peptide composition included a full complement of variants where applicable (e.g., the eight INF-HA-3-V3 peptide variants shown in Table 1, the four INF-H1-4-V4 peptide variants in Table 4, etc.). Commercial anti-influenza sera and human sera were diluted at 1/40 in IMDM and 50 μl was added to each well before the plates were incubated for 1 hr at 37° C. 50 μl of influenza virus strains Wisconsin (A/Wis/67/05) or New Calcdonia (A/NC/20/99) containing $1\times10^5$ pfu, in IMDM was added to each well and the plates were incubated for an additional 1 hr at 37° C. Subsequently, $5\times10^4$ Madin Darby Canine Kidney (MDCK) cells supplemented with 2% fetal calf serum (FCS) were added to each well. Every plate contained four cell and four virus control wells. The plates were incubated at 37° C. for 18-22 hrs. Cells were fixed for 10 minutes with 50 μl of ethanol 70% per well and air-dried at room temperature. The plates were washed 5 times with PBS containing 0.05% Tween-20 and the wells were blocked with 10% FCS. After 90 minutes at 4° C., 50 μl of monoclonal antibody directed against the influenza type A nucleocapsid antigen (Chemicon) diluted 1/500 in blocking buffer was added to each well. After further incubation for 1 hr at 4° C., the plates were washed 5 times and 100 μl of goat anti mouse IgG peroxidase-conjugated affinity purified antibody (1/10,000) was added to each well for 30 minutes at 4° C. The plates were washed 5 times and developed by 100 μl orthophenylenediamine (OPD: Sigma, St. Louise, Mo.) and the enzyme reaction was stopped after 20 min with 1N HCl. The reaction was quantified by measuring the OD at wavelength 490 nm by ELISA plate reader (Bio-Rad). The results for compositions comprising the peptide(s) of Tables 1, 2, 3, 4, 5, 6, 7, 8 and 9 are shown in FIG. 1.

Figure 1B:
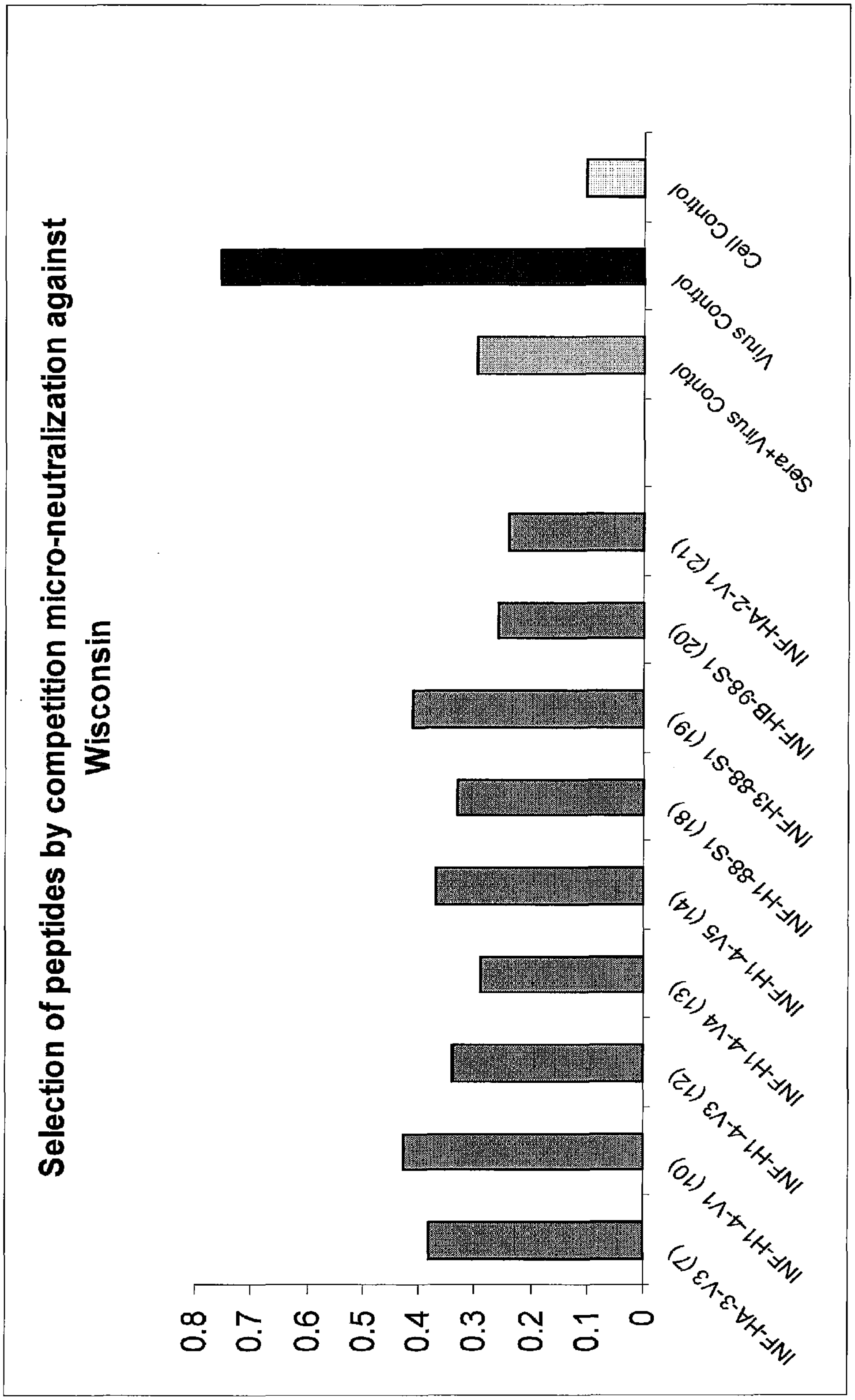

As shown in FIG. 1. addition of commercial or immune sera can inhibit influenza virus infection of cells in vitro, which is quantified by ELISA by optical density (OD) measurements. Thus, an OD value of approximately 0.6 (see Virus control) is reduced to approximately 0.2 in the presence of immune sera (see Virus+Sera control). Incubation of various peptide compositions with the sera allows the peptides to bind to some of the neutralizing antibodies present in the sera and thereby reverse their neutralizing activity (e.g., OD values of approximately 0.3 or higher).

TABLE 1

SEQ ID NOs. 1 and 19-26

| Peptide Name | Sequence | SEQ ID NO. |
|---|---|---|
| Consensus | GSRPXVREDGGLPQSXRISIXWTIVKPG | 1 |
| Substitution # 1 | ----D----------G----D------- | |
| Substitution # 2 | ----W----------S----Y------- | |
| INF-HA-3-V3/1 | GSRPDVREDGGLPQSGRISIDWTIVKPG | 19 |
| INF-HA-3-V3/2 | GSRPDVREDGGLPQSGRISIYWTIVKPG | 20 |
| INF-HA-3-V3/3 | GSRPDVREDGGLPQSSRISIDWTIVKPG | 21 |
| INF-HA-3-V3/4 | GSRPDVREDGGLPQSSRISIYWTIVKPG | 22 |
| INF-HA-3-V3/5 | GSRPWVREDGGLPQSGRISIDWTIVKPG | 23 |
| INF-HA-3-V3/6 | GSRPWVREDGGLPQSGRISIYWTIVKPG | 24 |
| INF-HA-3-V3/7 | GSRPWVREDGGLPQSSRISIDWTIVKPG | 25 |
| INF-HA-3-V3/8 | GSRPWVREDGGLPQSSRISIYWTIVKPG | 26 |

TABLE 2

SEQ ID NOs. 2 and 27-34

| Peptide Name | Sequence | SEQ ID NO. |
|---|---|---|
| Consensus | XTGVSASCSHNGXSSFYXNLLWLTGK | 2 |
| Substitution # 1 | V-----------K----R-------- | |
| Substitution # 2 | T-----------E----K-------- | |
| INF-H1-4-V1/1 | VTGVSASCSHNGKSSFYRNLLWLTGK | 27 |
| INF-H1-4-V1/2 | VTGVSASCSHNGKSSFYKNLLWLTGK | 28 |
| INF-H1-4-V1/3 | VTGVSASCSHNGESSFYRNLLWLTGK | 29 |
| INF-H1-4-V1/4 | VTGVSASCSHNGESSFYKNLLWLTGK | 30 |
| INF-H1-4-V1/5 | TTGVSASCSHNGKSSFYRNLLWLTGK | 31 |
| INF-H1-4-V1/6 | TTGVSASCSHNGKSSFYKNLLWLTGK | 32 |
| INF-H1-4-V1/7 | TTGVSASCSHNGESSFYRNLLWLTGK | 33 |
| INF-H1-4-V1/8 | TTGVSASCSHNGESSFYKNLLWLTGK | 34 |

TABLE 3

SEQ ID NOs. 3 and 35-42

| Peptide Name | Sequence | SEQ ID NO. |
|---|---|---|
| Consensus | HYSRXFTPEIXKRPKVRXQEGRINYYWTLLEPG | 3 |
| Substitution # 1 | ----R-----A------D--------------- | |
| Substitution # 2 | ----K-----T------N--------------- | |
| INF-H1-4-V3/1 | HYSRRFTPEIAKRPKVRDQEGRINYYWTLLEPG | 35 |
| INF-H1-4-V3/2 | HYSRRFTPEIAKRPKVRNQEGRINYYWTLLEPG | 36 |
| INF-H1-4-V3/3 | HYSRRFTPEITKRPKVRDQEGRINYYWTLLEPG | 37 |
| INF-H1-4-V3/4 | HYSRRFTPEITKRPKVRNQEGRINYYWTLLEPG | 38 |
| INF-H1-4-V3/5 | HYSRKFTPEIAKRPKVRDQEGRINYYWTLLEPG | 39 |
| INF-H1-4-V3/6 | HYSRKFTPEIAKRPKVRNQEGRINYYWTLLEPG | 40 |
| INF-H1-4-V3/7 | HYSRKFTPEITKRPKVRDQEGRINYYWTLLEPG | 41 |
| INF-H1-4-V3/8 | HYSRKFTPEITKRPKVRNQEGRINYYWTLLEPG | 42 |

TABLE 4

SEQ ID NOs. 4 and 43-46

| Peptide Name | Sequence | SEQ ID NO. |
|---|---|---|
| Consensus | PVTIGECPKYVRSXKLRMXTGLRNIPSIQS | 4 |
| Substitution # 1 | -------------A----V----------- | |
| Substitution # 2 | -------------T----A----------- | |
| INF-H1-4-V4/1 | PVTIGECPKYVRSAKLRMVTGLRNIPSIQS | 43 |
| INF-H1-4-V4/2 | PVTIGECPKYVRSAKLRMATGLRNIPSIQS | 44 |
| INF-H1-4-V4/3 | PVTIGECPKYVRSTKLRMVTGLRNIPSIQS | 45 |
| INF-H1-4-V4/4 | PVTIGECPKYVRSTKLRMATGLRNIPSIQS | 46 |

TABLE 5

SEQ ID NOs. 5 and 47-54

| Peptide Name | Sequence | SEQ ID NO. |
|---|---|---|
| Consensus | CELLISXESWSYIVEXPNPENGTCYPGXF | 5 |
| Substitution # 1 | ------K--------T-----------Y- | |
| Substitution # 2 | ------R--------K-----------H- | |
| INF-H1-4-V5/1 | CELLISKESWSYIVETPNPENGTCYPGYF | 47 |
| INF-H1-4-V5/2 | CELLISKESWSYIVETPNPENGTCYPGHF | 48 |
| INF-H1-4-V5/3 | CELLISKESWSYIVEKPNPENGTCYPGYF | 49 |
| INF-H1-4-V5/4 | CELLISKESWSYIVEKPNPENGTCYPGHF | 50 |
| INF-H1-4-V5/5 | CELLISRESWSYIVETPNPENGTCYPGYF | 51 |
| INF-H1-4-V5/6 | CELLISRESWSYIVETPNPENGTCYPGHF | 52 |
| INF-H1-4-V5/7 | CELLISRESWSYIVEKPNPENGTCYPGYF | 53 |
| INF-H1-4-V5/8 | CELLISRESWSYIVEKPNPENGTCYPGHF | 54 |

TABLE 6

SEQ ID NO. 6

| Peptide Name | Sequence | SEQ ID NO. |
|---|---|---|
| INF-H1-88-S1 | SWPNHTTTGVSASSSHNGESSFYKNLLWLTGKNGL YPNLSKSYANNKEKEVLVLWGVHHPPNIGDQRALY HKENAYVSVVSIIFEANG | 6 |

TABLE 7

SEQ ID NO. 7

| Peptide Name | Sequence | SEQ ID NO. |
|---|---|---|
| INF-H3-88-S1 | NWTGVTQNGTSSSSKRRSNNSFFSRLNWLTHLKFK YPALNTMPNNEKFDKLYIWGVHHPVTDNDQIFLYA QASGRITVSTLLINSTG | 7 |

TABLE 8

| SEQ ID NO. 8 | | |
|---|---|---|
| Peptide Name | Sequence | SEQ ID NO. |
| INF-HB-98-S1 | NAEKAPGGPYKIGTSGSSPNVTNGNGFFATMAWAV | 8 |
| | PKNDNNKTATNSLTIEVPYISTEGEDQITIWGFHS | |
| | DNETQMAKLYGDSKPQKFTSSAGTITYQ | |

TABLE 9

| SEQ ID NOs. 9 and 55-70 | | |
|---|---|---|
| Peptide Name | Sequence | SEQ ID NO. |
| Consensus | YACKXGGKSSGSSYPVLXXXY | 9 |
| Substitution # 1 | ----R------------KVS- | |
| Substitution # 2 | ----Y------------SRT- | |
| INF-HA-2-V1/1 | YACKRGGKSSGSSYPVLKVSY | 55 |
| INF-HA-2-V1/2 | YACKRGGKSSGSSYPVLKVTY | 56 |
| INF-HA-2-V1/3 | YACKRGGKSSGSSYPVLKRSY | 57 |
| INF-HA-2-V1/4 | YACKRGGKSSGSSYPVLKRTY | 58 |
| INF-HA-2-V1/5 | YACKRGGKSSGSSYPVLSVSY | 59 |
| INF-HA-2-V1/6 | YACKRGGKSSGSSYPVLSVTY | 60 |
| INF-HA-2-V1/7 | YACKRGGKSSGSSYPVLSRSY | 61 |
| INF-HA-2-V1/8 | YACKRGGKSSGSSYPVLSRTY | 62 |
| INF-HA-2-V1/9 | YACKYGGKSSGSSYPVLKVSY | 63 |
| INF-HA-2-V1/10 | YACKYGGKSSGSSYPVLKVTY | 64 |
| INF-HA-2-V1/11 | YACKYGGKSSGSSYPVLKRSY | 65 |
| INF-HA-2-V1/12 | YACKYGGKSSGSSYPVLKRTY | 66 |
| INF-HA-2-V1/13 | YACKYGGKSSGSSYPVLSVSY | 67 |
| INF-HA-2-V1/14 | YACKYGGKSSGSSYPVLSVTY | 68 |
| INF-HA-2-V1/15 | YACKYGGKSSGSSYPVLSRSY | 69 |
| INF-HA-2-V1/16 | YACKYGGKSSGSSYPVLSRTY | 70 |

Example 3

ELISPOT Assay

In this Example, the immunogenicity of the peptide compositions of Example 1 was tested by measuring activation (as measured by IFNγ output) of human PBMCs in an ELISPOT assay. Multiscreen-HTS plates (Millipore, Bedford, Mass.) were coated with 10 μg/ml of anti-mouse IFNγ antibody (mAb AN18, Mabtech, Mariemont, Ohio) in PBS overnight at 4° C. The plates were then washed with PBS and blocked with IMDM containing 10% FCS and 100 U/ml penicillin/streptomycin for 1 hr at room temperature. The medium was removed and $2\times10^5$ peripheral blood mononuclear cell (PBMCs) from influenza-vaccinated human subjects (200 μl/well) mixed with peptide compositions (40 μg/ml, see FIG. 2 and Tables 1-9) were added to each well for 2 days. After incubation, cells were removed, washed with PBS+0.05% Tween 20 and incubated with 1 μg/ml of biotinylated anti-mouse IFNγ antibody (mAb R4-6A2-Biotin, Mabtech) for 2 hrs at room temperature. After washing, 100 μl/well of 1/1000 Streptavidin-ALP-PQ (Mabtech) in PBS+0.5% FCS was added and incubated for 1 hr at room temperature. The plates were washed as above and developed with 100 μl per well BCIP/NBT alkaline phosphatase (Moss Inc) for 20 minutes at room temperature. The reaction was stopped by rinsing the plates with tap water. The numbers of spots in each well were magnified and counted. The results for compositions comprising the peptide(s) of Tables 1, 2, 3, 4, 5, 6, 7, 8 and 9 are shown in FIG. 2.

Figure 2:
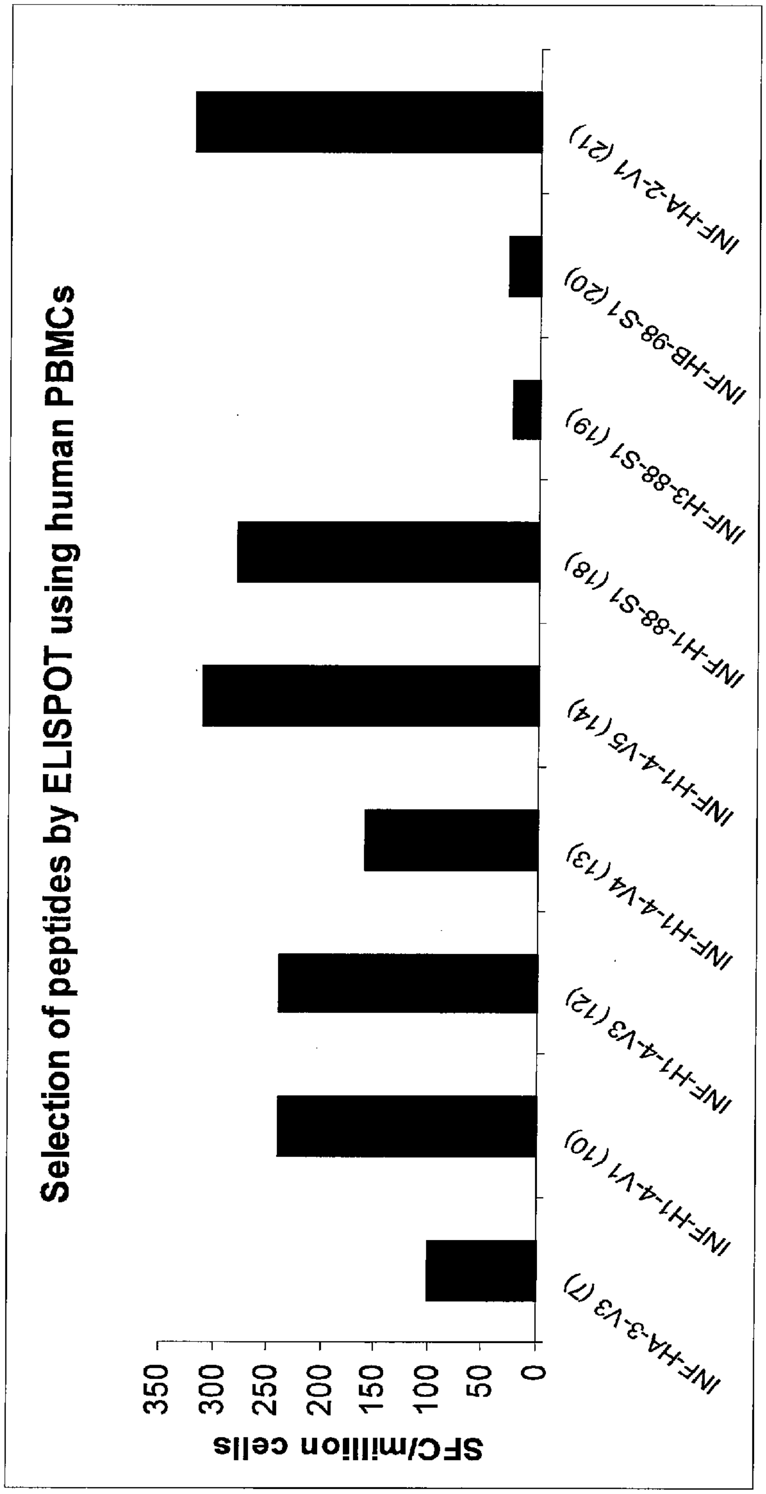
FIG. 2 shows the cell-mediated immune responses triggered by exemplary peptide compositions as detected by IFNγ-ELISPOT assay expressed as spot forming cells (SFC) per million cells. Peripheral blood mononuclear cells (PBMCs) from an influenza-vaccinated individual were cultured in the presence of selected peptides. The plates were developed after 2 days and numbers of spots in each well were magnified and counted.

As shown in FIG. 2, certain peptide compositions elicited a strong response in this assay, confirming that these compositions were immunogenic.

Example 4

Other Peptides

Tables 10-14 in this Example describe other exemplary peptides that may be used in the compositions and methods described herein.

TABLE 10

| SEQ ID NOs. 10 and 71-86 | | |
|---|---|---|
| Peptide Name | Sequence | SEQ ID NO. |
| Consensus | YACKXGGKSSGSSYPVLXVXX | 10 |
| Substitution # 1 | ----R------------N-SY | |
| Substitution # 2 | ----H------------S-TM | |
| INF-HA-1-V1/1 | YACKRGGKSSGSSYPVLNVSY | 71 |
| INF-HA-1-V1/2 | YACKRGGKSSGSSYPVLNVSM | 72 |
| INF-HA-1-V1/3 | YACKRGGKSSGSSYPVLNVTY | 73 |
| INF-HA-1-V1/4 | YACKRGGKSSGSSYPVLNVTM | 74 |
| INF-HA-1-V1/5 | YACKRGGKSSGSSYPVLSVSY | 75 |
| INF-HA-1-V1/6 | YACKRGGKSSGSSYPVLSVSM | 76 |
| INF-HA-1-V1/7 | YACKRGGKSSGSSYPVLSVTY | 77 |
| INF-HA-1-V1/8 | YACKRGGKSSGSSYPVLSVTM | 78 |
| INF-HA-1-V1/9 | YACKHGGKSSGSSYPVLNVSY | 79 |
| INF-HA-1-V1/10 | YACKHGGKSSGSSYPVLNVSM | 80 |
| INF-HA-1-V1/11 | YACKHGGKSSGSSYPVLNVTY | 81 |
| INF-HA-1-V1/12 | YACKHGGKSSGSSYPVLNVTM | 82 |
| INF-HA-1-V1/13 | YACKHGGKSSGSSYPVLSVSY | 83 |
| INF-HA-1-V1/14 | YACKHGGKSSGSSYPVLSVSM | 84 |
| INF-HA-1-V1/15 | YACKHGGKSSGSSYPVLSVTY | 85 |
| INF-HA-1-V1/16 | YACKHGGKSSGSSYPVLSVTM | 86 |

TABLE 11

SEQ ID NOs. 11 and 87-102

| Peptide Name | Sequence | SEQ ID NO. |
|---|---|---|
| Consensus | YASKXGGKSSGSSYPVLXVXX | 11 |
| Substitution # 1 | ----R------------N-SY | |
| Substitution # 2 | ----H------------S-TM | |
| INF-HA-1-V1 (C3S)/1 | YASKRGGKSSGSSYPVLNVSY | 87 |
| INF-HA-1-V1 (C3S)/2 | YASKRGGKSSGSSYPVLNVSM | 88 |
| INF-HA-1-V1 (C3S)/3 | YASKRGGKSSGSSYPVLNVTY | 89 |
| INF-HA-1-V1 (C3S)/4 | YASKRGGKSSGSSYPVLNVTM | 90 |
| INF-HA-1-V1 (C3S)/5 | YASKRGGKSSGSSYPVLSVSY | 91 |
| INF-HA-1-V1 (C3S)/6 | YASKRGGKSSGSSYPVLSVSM | 92 |
| INF-HA-1-V1 (C3S)/7 | YASKRGGKSSGSSYPVLSVTY | 93 |
| INF-HA-1-V1 (C3S)/8 | YASKRGGKSSGSSYPVLSVTM | 94 |
| INF-HA-1-V1 (C3S)/9 | YASKHGGKSSGSSYPVLNVSY | 95 |
| INF-HA-1-V1 (C3S)/10 | YASKHGGKSSGSSYPVLNVSM | 96 |
| INF-HA-1-V1 (C3S)/11 | YASKHGGKSSGSSYPVLNVTY | 97 |
| INF-HA-1-V1 (C3S)/12 | YASKHGGKSSGSSYPVLNVTM | 98 |
| INF-HA-1-V1 (C3S)/13 | YASKHGGKSSGSSYPVLSVSY | 99 |
| INF-HA-1-V1 (C3S)/14 | YASKHGGKSSGSSYPVLSVSM | 100 |
| INF-HA-1-V1 (C3S)/15 | YASKHGGKSSGSSYPVLSVTY | 101 |
| INF-HA-1-V1 (C3S)/16 | YASKHGGKSSGSSYPVLSVTM | 102 |

TABLE 12

| Peptide Name | Sequence | SEQ ID NO. |
|---|---|---|
| 02-HB-01-S1-01 | AEKAPGGPYKIGTSGSSPNVTNGNGFFATMAWAVPKNDNNKTATNSLT | 12 |
| 02-HB-01-S2-01 | FHSDNETQMAKLYGDSKPQKFTSSANGVTTHYVSQIGGFPNQTEDGGLPQSGRI | 13 |

TABLE 13

SEQ ID NOs. 14 and 103-118

| Peptide Name | Sequence | SEQ ID NO. |
|---|---|---|
| Consensus | SVQRNLPFXXXTXMA | 14 |
| Substitution # 1 | --------EKS-V-- | |
| Substitution # 2 | --------DRT-I-- | |
| INF-NP-1-V1/1 | SVQRNLPFEKSTVMA | 103 |
| INF-NP-1-V1/2 | SVQRNLPFEKSTIMA | 104 |
| INF-NP-1-V1/3 | SVQRNLPFEKTTVMA | 105 |
| INF-NP-1-V1/4 | SVQRNLPFEKTTIMA | 106 |
| INF-NP-1-V1/5 | SVQRNLPFERSTVMA | 107 |
| INF-NP-1-V1/6 | SVQRNLPFERSTIMA | 108 |
| INF-NP-1-V1/7 | SVQRNLPFERTTVMA | 109 |
| INF-NP-1-V1/8 | SVQRNLPFERTTIMA | 110 |
| INF-NP-1-V1/9 | SVQRNLPFDKSTVMA | 111 |
| INF-NP-1-V1/10 | SVQRNLPFDKSTIMA | 112 |
| INF-NP-1-V1/11 | SVQRNLPFDKTTVMA | 113 |
| INF-NP-1-V1/12 | SVQRNLPFDKTTIMA | 114 |
| INF-NP-1-V1/13 | SVQRNLPFDRSTVMA | 115 |
| INF-NP-1-V1/14 | SVQRNLPFDRSTIMA | 116 |
| INF-NP-1-V1/15 | SVQRNLPFDRTTVMA | 117 |
| INF-NP-1-V1/16 | SVQRNLPFDRTTIMA | 118 |

TABLE 14

SEQ ID NOs. 15 and 119-134

| Peptide Name | Sequence | SEQ ID NO. |
|---|---|---|
| Consensus | XXXSSTLELRSXYWAI | 15 |
| Substitution # 1 | NMG--------G---- | |
| Substitution # 2 | AIE--------R---- | |
| INF-NP-2-V2/1 | NMGSSTLELRSGYWAI | 119 |
| INF-NP-2-V2/2 | NMGSSTLELRSRYWAI | 120 |
| INF-NP-2-V2/3 | NMESSTLELRSGYWAI | 121 |
| INF-NP-2-V2/4 | NMESSTLELRSRYWAI | 122 |
| INF-NP-2-V2/5 | NIGSSTLELRSGYWAI | 123 |
| INF-NP-2-V2/6 | NIGSSTLELRSRYWAI | 124 |
| INF-NP-2-V2/7 | NIESSTLELRSGYWAI | 125 |
| INF-NP-2-V2/8 | NIESSTLELRSRYWAI | 126 |
| INF-NP-2-V2/9 | AMGSSTLELRSGYWAI | 127 |
| INF-NP-2-V2/10 | AMGSSTLELRSRYWAI | 128 |
| INF-NP-2-V2/11 | AMESSTLELRSGYWAI | 129 |
| INF-NP-2-V2/12 | AMESSTLELRSRYWAI | 130 |
| INF-NP-2-V2/13 | AIGSSTLELRSGYWAI | 131 |
| INF-NP-2-V2/14 | AIGSSTLELRSRYWAI | 132 |
| INF-NP-2-V2/15 | AIESSTLELRSGYWAI | 133 |
| INF-NP-2-V2/16 | AIESSTLELRSRYWAI | 134 |

Example 5

Peptide Composition INF-61P

Peptide composition INF-61P includes a mixture of peptides as set forth in Table 15.

TABLE 15

| Peptide(s) | SEQ ID NO. |
|---|---|
| All sixteen (16) variants from Table 11 | 11[1] |
| Peptide from Table 6 | 6 |
| Peptide from Table 8 | 8 |

[1]SEQ ID NO. 11 is a consensus sequence and covers 16 different variants.

Example 6

Peptide Composition INF-63P

Peptide composition INF-63P includes a mixture of peptides as set forth in Table 16.

TABLE 16

| Peptide(s) | SEQ ID NO. |
|---|---|
| All sixteen (16) variants from Table 11 | 11[1] |
| Peptide from Table 6 | 6 |
| Both peptides from Table 12 | 12, 13 |

[1]SEQ ID NO. 11 is a consensus sequence and covers 16 different variants.

Example 7

Peptide Composition SFV2

Peptide composition SFV2 includes a mixture of peptides as set forth in Table 17.

TABLE 17

| Peptide(s) | SEQ ID NO. |
|---|---|
| All sixteen (16) variants from Table 11 | 11[1] |
| Peptide from Table 6 | 6 |
| Both peptides from Table 12 | 12, 13 |
| All sixteen (16) variants from Table 13 | 14[2] |

[1]SEQ ID NO. 11 is a consensus sequence and covers 16 different variants.
[2]SEQ ID NO. 14 is a consensus sequence and covers 16 different variants. In certain embodiments, the peptides in SFV2 may differ from these sequences by the addition of a KSS linker at the N-terminus of each peptide which could be optionally used for lipidation at the N-terminal lysine moiety.

Example 8

Bilosome INF-61P Composition

This Example describes the preparation of the bilosome INF-61P composition that was used in Examples 9 and 11 for oral delivery of peptide compositions. Lipids (monopalmitoyl-glycerol, cholesterol and dicetylphosphate) were dissolved in chloroform and dried to a film, then rehydrated with the INF-61P peptides of Example 5 and sodium deoxycholate (a "bile salt"). The resulting bilosomes were evaluated for size using dynamic light scattering and for entrapment efficiency using a Ninhydrin assay. Loaded bilosomes were then adjusted in volume to produce a composition with the desired quantity of peptides. As described below, these loaded bilosomes were capable of delivering immunogenic peptide compositions to ferrets and mice even when administered orally.

Example 9

Oral Influenza Immunization of Ferrets with Bilosome INF-61P Composition

This Example describes in vivo testing of certain immunogenic peptide compositions in ferrets. The ferret model of influenza virus infection is the gold standard mammalian model for evaluating candidate influenza vaccines. Indeed, ferrets can be infected with clinical isolates of all major subtypes of influenza A and B and exhibit a clinical course of disease comparable to that seen in humans (including an increase in body temperature and in some cases weight loss).

A number of researchers have demonstrated that currently licensed influenza vaccines given by intramuscular (IM) injection induce neutralizing IgG antibodies that also possess hemagglutination inhibition activity. Induction of cellular immunity with these existing vaccines, and its role in protection, is unclear. As discussed below, we have shown that orally administered immunogenic peptide compositions induce IgA antibodies systemically (serum) and mucosally (rectal and nasal wash samples). Since influenza infection occurs via mucosal surfaces, an IgA response (the hallmark of a mucosal immune response) may be more efficacious than a systemic IgG response. As shown in Example 13, systemic IgG responses were obtained when the immunogenic peptide compositions were administered by standard parenteral routes (e.g., by IM injection).

For the vaccination and challenge experiments, male ferrets were selected that had been pre-screened as serum negative by the hemagglutination inhibition assay. Compositions for oral delivery were formulated so that the peptides were contained in a volume of 0.5 ml. All ferrets were bled 3 days before immunization and serum, plasma and PBMCs were collected. Ferrets receiving INF-61P compositions were immunized perorally on Days 0, 3, 14, and 17 by gastric lavage after fasting. For commercial vaccine controls, FLUVIRAL vaccine was injected IM into the quadriceps muscle on Days 0 and 17.

On Day 27, ferrets were bled for serum and saliva and rectal washes were collected. All ferrets were then challenged intranasally with influenza virus diluted to $2\times10^6$ pfu/ml with PBS (0.5 ml/nostril). For 10 days following virus challenge, nasal washes were collected and all animals were weighed and monitored daily for clinical signs of infection (body temperature measured electronically by implants within each animal). At sacrifice, animals were bled for serum, plasma, PBMCs and (in some instances) complete blood count (CBC), and spleens were collected and processed for mononuclear cells.

Figure 3:
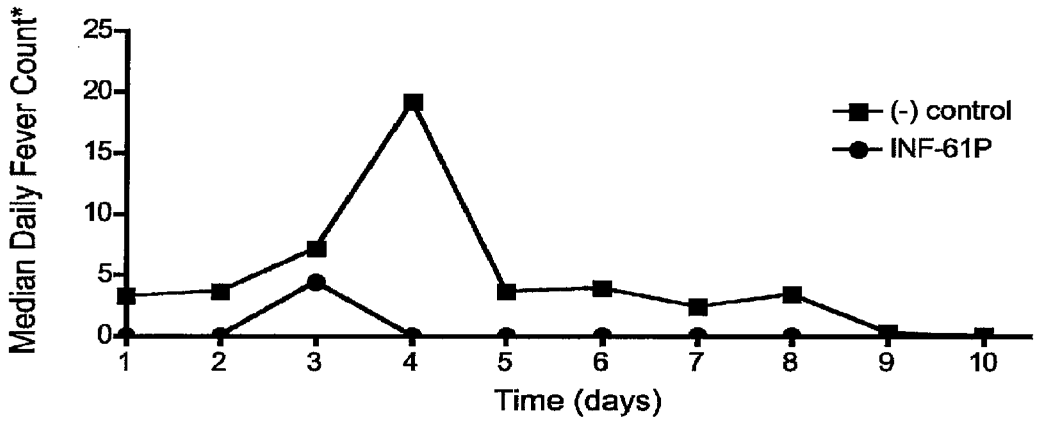
FIG. 3 shows median daily fever counts during a 10 day period after challenge with $1\times10^6$ plaque-forming units (pfu) of H3N2 (A/Wisconsin/2005) virus in animals vaccinated with peptide composition INF-61P compared to non-vaccinated control animals. Fever count was defined as every minute an animal had a body temperature of 40° C. or higher; median fever counts among 4 animals per group were calculated every 3 hours. The control and vaccinated animals had comparable starting body temperatures (see Day 0).
Figure 4:
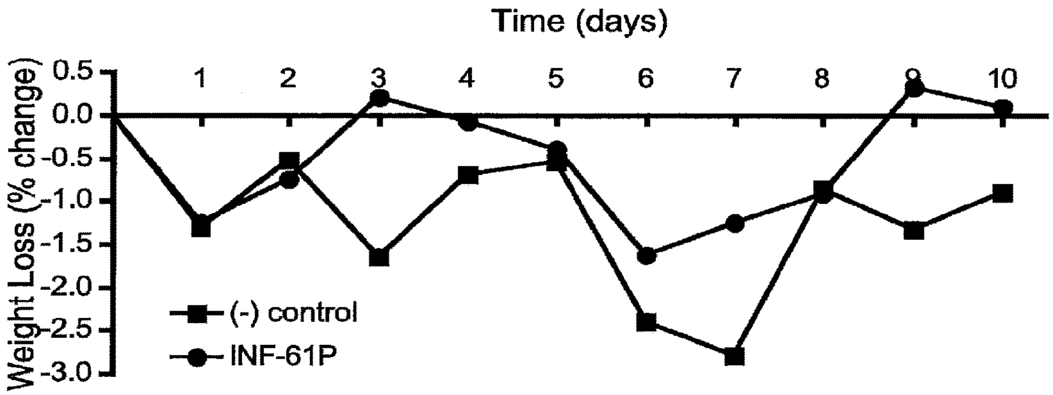
FIG. 4 shows weight loss during a 10 day period after challenge with $1\times10^6$ pfu of H3N2 (A/Wisconsin/2005) virus in animals vaccinated with peptide composition INF-61P compared to non-vaccinated control animals.

As shown in FIG. 3, when animals were inoculated with immunogenic peptide composition INF-61P (see Example 5) and challenged with H3N2 (A/Wisconsin/2005) virus, they exhibited reduced fever counts, showing a protective effect of composition INF-61P. Furthermore, INF-61P-vaccinated animals (see FIG. 4) exhibited less drastic weight loss in the days after challenge with virus as compared to control mice.

Figure 5:
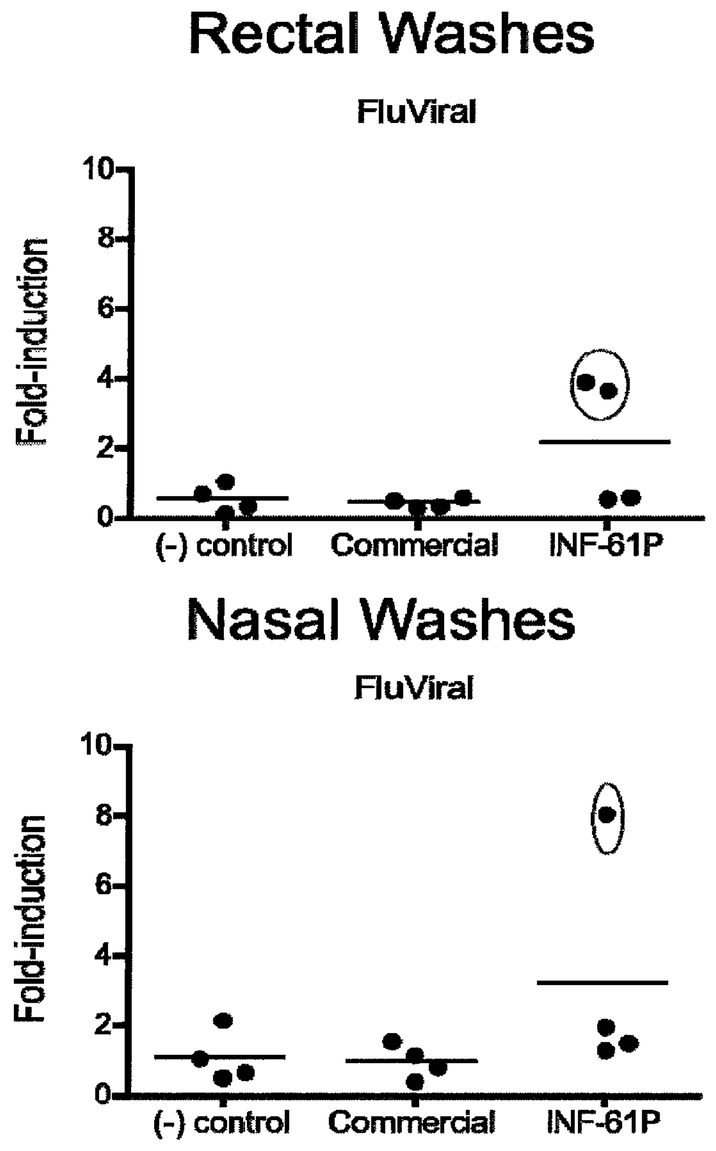
FIG. 5 shows mucosal IgA responses directed against influenza virus (FLUVIRAL) that were seen in rectal wash (top panel) and nasal wash samples (bottom panel) from ferrets immunized with peptide composition INF-61P. The data is represented as fold increase relative to pre-vaccination responses in each animal, and has been normalized for the total amount of IgA present in the different samples. Comparative data that was obtained with a commercial influenza vaccine (FLUVIRAL) are also provided.

As depicted in FIG. 5, composition INF-61P induced mucosal IgA responses as seen in rectal wash (top panel) and nasal wash (bottom panel) samples. The majority (¾) of animals vaccinated with INF-61P exhibited at least a two-fold increase in IgA titer relative to pre-vaccination responses in either rectal or nasal wash samples. As expected, the commercial vaccine which was given by standard IM injection induced systemic (serum) IgG responses (data not shown). However, as shown in FIG. 5 it induced no IgA responses.

Figure 6:
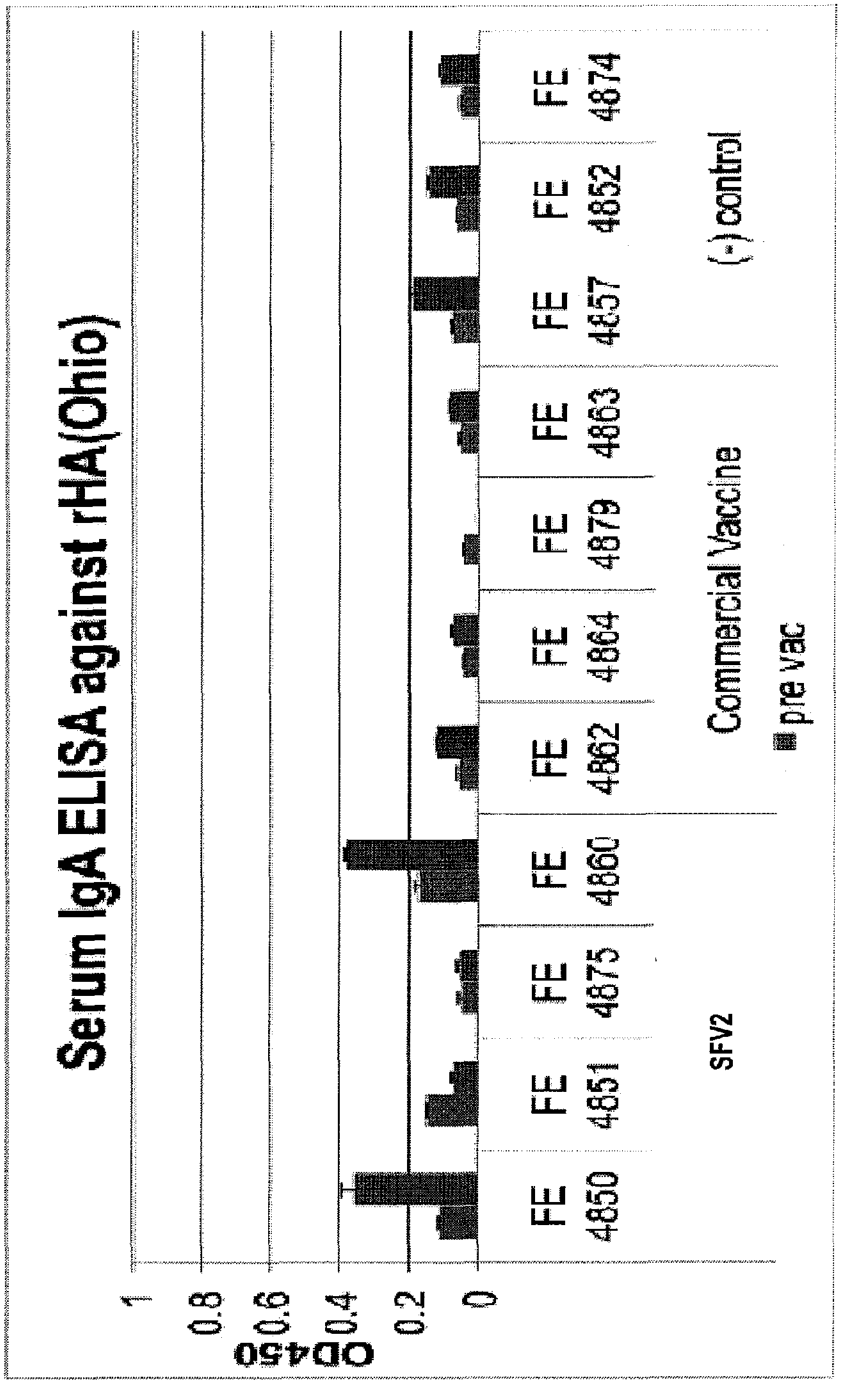
FIG. 6 shows serum IgA responses directed against recombinant HA protein from influenza type B (Ohio) that were seen in serum from ferrets immunized with peptide composition SFV2. Responses measured by ELISA (reported as optical density) from pre-vaccination and post-vaccination serum samples for each animal are shown in paired left and right columns, respectively. Strong positive responses can be seen in animals #4850 and #4860.

Similar results (data not shown) were observed when this experiment was reproduced with an immunogenic peptide composition that included the SFV2 peptides (see Example 7). Of note, serum IgA directed against recombinant HA protein from influenza type B was detected in animals vaccinated with composition SFV2 (see FIG. 6).

Example 10

Immune Response Study of a Subcutaneously Administered INF-09L-A Composition This Example describes the immune response induced by subcutaneously administering a modified version (INF-09L-A) of the peptide composition of Table 13 (INF-NP1-V1) in mice. The INF-09L-A peptide composition differed from the INF-NP1-V1 composition shown in Table 13 by the inclusion of a KSS linker on the N-terminus of each peptide. The N-terminal lysine moiety was used to double lipidate each peptide.

Figure 7:
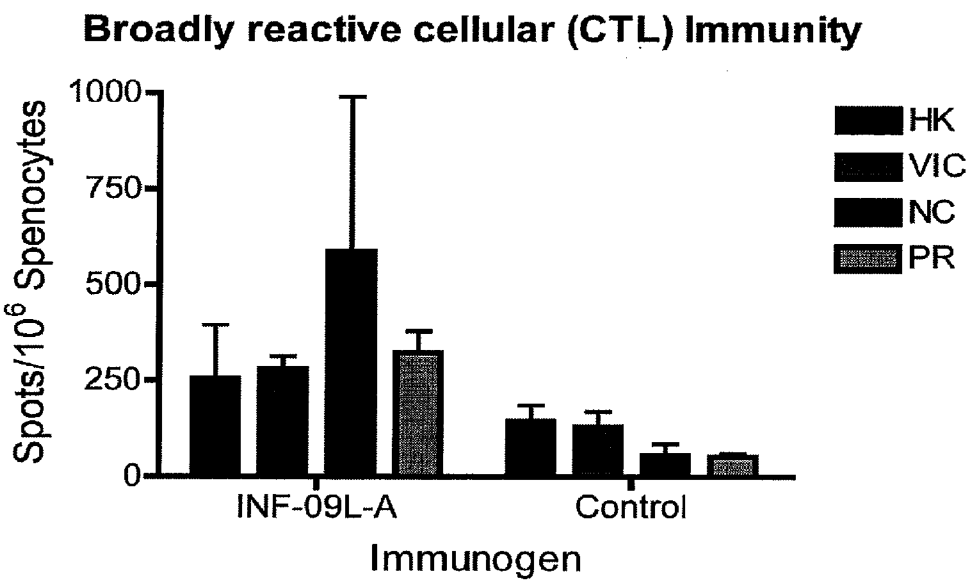
FIG. 7 shows broadly reactive cellular (CTL) immunity induced with lipidated peptide composition INF-09L-A. Aged (>12 months) HLA (A*0201) transgenic mice were vaccinated three times with the composition which targets a variable region in the nucleoprotein of type A influenza. The composition also included an alum adjuvant. A control group only received the adjuvant. Splenocytes were infected with divergent strains of influenza from multiple subtypes: H3N2 (A/HK/1/18, A/VICtoria/3/75) and H1N1 (A/NC/20/99, A/PR/8/34). Spots represent the frequency of IFNγ-secreting T cells specific for each of the strains of virus, and error bars represent the standard deviation among mice in each group (n=3). The results are presented from left to right as follows: H3N2 (A/HK/1/18), H3N2 (A/VICtoria/3/75), H1N1 (A/NC/20/99) and H1N1 (A/PR/8/34).

Aged (>12 months) HLA (A*0201) transgenic mice were vaccinated three times with the INF-09L-A peptide composition. All sixteen variants were included in the administered composition. The composition also included an alum adjuvant. A control group only received the adjuvant. Splenocytes were infected with divergent strains of influenza from multiple subtypes: H3N2 (A/HK/1/18, A/VICtoria/3/75) and H1N1 (A/NC/20/99, A/PR/8/34). T cell responses were measured by quantitating the frequency of IFNγ-secreting T cells in an ELISPOT assay (see Example 3 for methodology). Spots represent the frequency of IFNγ-secreting T cells specific for each of the strains of virus, and error bars represent the standard deviation among mice in each group (n=3). The results are presented from left to right as follows: H3N2 (A/HK/1/18), H3N2 (A/VICtoria/3/75), H1N1 (A/NC/20/99) and H1N1 (A/PR/8/34). As shown in FIG. 7, the peptide composition induced a broad cellular (CTL) immune reaction.

Example 11

Effect of Adjuvant on Immune Response Induced by an Orally Administered Peptide Composition This Example compares the immune response induced by orally administering a peptide composition to mice with and without an adjuvant.

Figure 8:
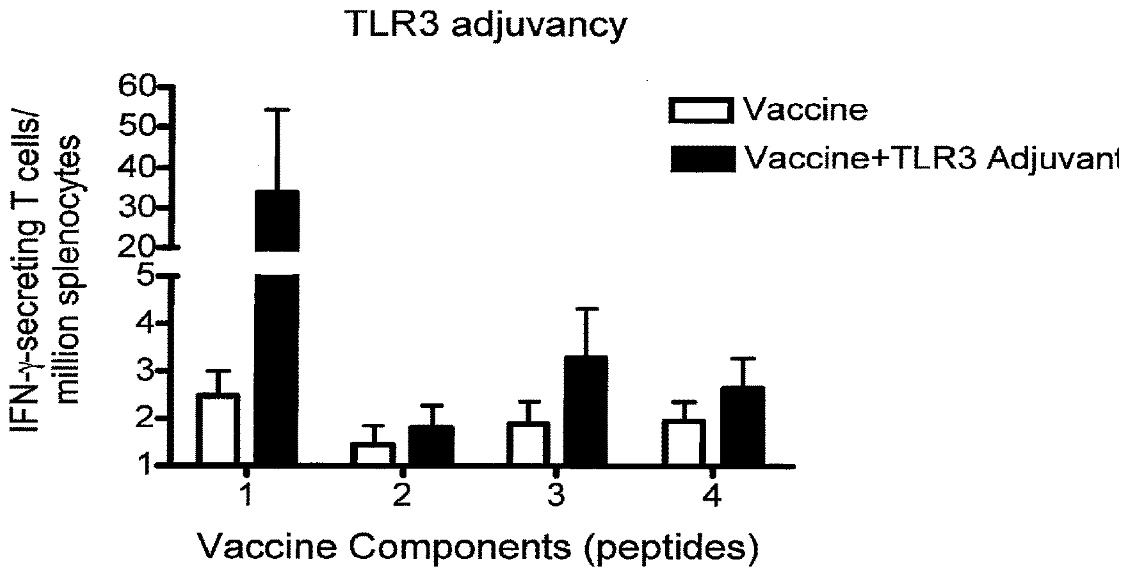
FIG. 8 shows immune responses to a peptide composition administered orally, with or without a TLR-3 agonist adjuvant (poly I:C). Mice (n=4 per group) were immunized orally 4 times (Days 0, 3, 14, and 17). Splenocytes were harvested after vaccinations and stimulated in vitro with the same peptide composition. Responses were measured using an IFNγ ELISPOT assay.

Mice (n=4) received a peptide composition entrapped in bilosomes, either with or without a TLR-3 based adjuvant (poly I:C). Mice were immunized orally 4 times (Days 0, 3, 14, and 17). Splenocytes were harvested after vaccinations and separately stimulated in vitro with the four individual peptides that were present in the peptide composition. Responses were measured using an IFNγ ELISPOT (see Example 3 for methodology). The results for each peptide challenge are compared in FIG. 8. As shown in FIG. 8, animals that received the peptide composition in combination with the adjuvant showed a greater response than did animals that received the peptide composition alone.

Example 12

Vesicle SFV2 Composition

This Example describes the preparation of the composition that was used in Example 13 for intramuscular (IM) injections of peptide compositions. The vesicles were composed of the following lipids: 1-monopalmitoyl glycerol (a non-ionic surfactant), cholesterol (a steroid) and dicetylphosphate (an ionic amphiphile). Specifically, a 5:4:1 molar ratio of lipids (270 mg of 1-monopalmitoyl glycerol (MPG), 255 mg of cholesterol (CHO), and 90 mg of dicetylphosphate (DCP)) was placed in a flat bottom 25 ml glass beaker, ensuring none of the powder was adhering to the side of the glass beaker. The beaker was clamped and covered with aluminum foil and the lipids were melted in a heated oil bath at 135° C. for 10 minutes, with occasional swirling in the beaker. In some compositions a synthetic TLR-4 agonist, PHAD (phosphorylated hexaacyl disaccharide from Avanti Polar Lipids, Inc., shown in FIG. 13) was co-melted with the other lipids, in other compositions PHAD was added with the peptide composition SFV2 (described in Example 7). The resulting mixture of 10 ml of peptide composition SFV2 (400 μg/ml) and PHAD (100 μg/ml) was pre-incubated in sodium bicarbonate solution (pH 8.5) for 5 minutes at 30° C. in a heated water bath. The peptide solution was homogenized at 8,000 rpm and then transferred to the melted lipid solution, at which point homogenization continued for 10 minutes at 30° C. (it will be appreciated that alternatively, the heated lipid solution could have been transferred to the antigen solution and subsequently homogenized). Finally, 10 ml of 400 mM sucrose solution in buffer was added to the vesicle/peptide solution and vortexed for 30 seconds. The vesicles (with or without peptide) were aliquoted into vials (0.5 ml/vial) and lyophilized. Lyophilized vesicles (with or without peptide) were rehydrated prior to administration in 0.5 ml of saline and absorbed to alum (aluminum hydroxide).

Example 13

Parenteral Immunization of Ferrets with Vesicle SFV2 Composition

This Example describes in vivo testing of the vesicle SFV2 composition of Example 12 in ferrets. For the vaccination and challenge experiments, male ferrets were selected that had been pre-screened as serum negative by the hemagglutination inhibition assay. Compositions for intramuscular injection were formulated as described in Example 12 so that the peptides were contained in a volume of 0.5 ml. All ferrets were bled 3 days before immunization and serum, plasma and PBMCs were collected. Ferrets were immunized by intramuscular injection (IM) with vesicles with or without SFV2 peptide composition on Day 0 and Day 28. For commercial vaccine controls, VAXIGRIP commercial vaccine was injected IM into the quadriceps muscle on Day 0 and Day 28. This commercial vaccine is an inactivated influenza vaccine trivalent for types A and B strains for the 2008-2009 season (specifically strains A/Brisbane/59/2007 H1N1; A/Brisbane/10/2007 H3N2 and B/Florida/4/2006). The experimental groups for this study are summarized in Table 18.

TABLE 18

| Group | Composition | Antigen (μg) | PHAD (μg) | Route of Administration | No. of Animals |
|---|---|---|---|---|---|
| 1 | Vesicles with SFV2 peptides, PHAD and alum | 200 | 50 | IM | 4 |
| 3 | VAXIGRIP | 45 | — | IM | 4 |
| 4 | Empty vesicles with PHAD and alum | 0 | 50 | IM | 4 |

On Day 28, ferrets were bled and serum samples were collected. All ferrets were then challenged intranasally with influenza virus at $2\times10^5$ pfu/ml with PBS (0.5 ml per nostril). For 10 days following virus challenge, nasal washes were collected and all animals were weighed and monitored daily for clinical signs of infection (body temperature measured electronically by implants within each animal). At sacrifice, animals were bled for serum, plasma, PBMCs and (in some instances) complete blood count (CBC), and spleens were collected and processed for mononuclear cells.

Figure 10A:
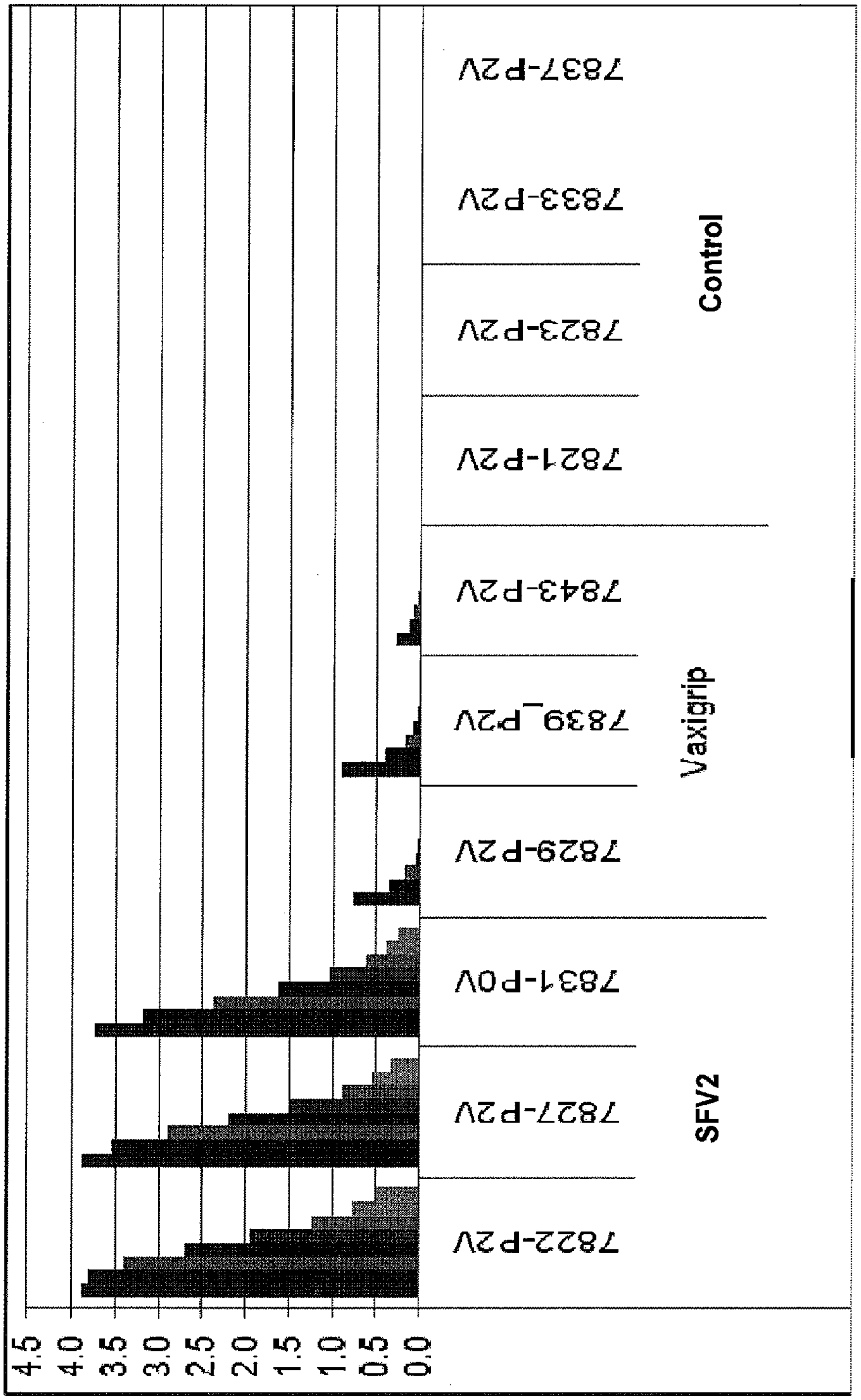
FIGS. 10A-B show serum IgG responses (measured by ELISA) directed against recombinant hemagglutinin (rHA) proteins from the following subtypes of influenza type A: (A/Solomon Island/03/06) H1N1 or (A/Wisconsin/67/05) H3N2 that were measured in ferrets immunized with peptide composition SFV2 administered intramuscularly. Post immunization serum demonstrated a significant immune response in ELISA with both rHA Solomon (A) and Wisconsin (B) for ferrets immunized with peptide composition SFV2 administered intramuscularly. No IgG response was detected against rHA from influenza type B (B/Malaysia/2506/04) (data not shown). Comparative data that was obtained with a commercial influenza vaccine (VAXIGRIP) are also provided.
Figure 10B:
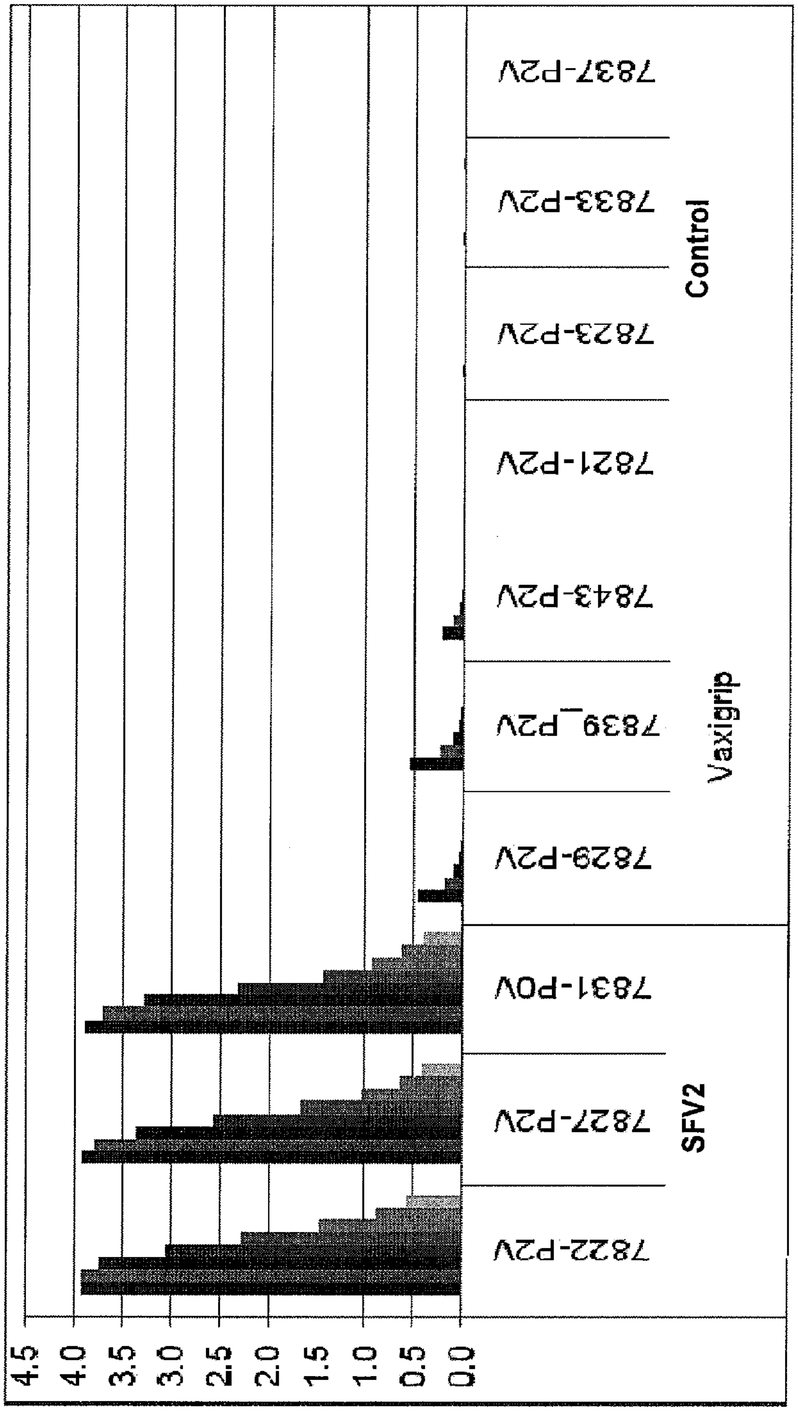

As shown in FIGS. 10A-B, composition SFV2 given IM induces a humoral response. Post immunization serum demonstrated a significant immune response in ELISA with both rHA Solomon (A) and Wisconsin (B) for ferrets immunized with peptide composition SFV2 administered intramuscularly. VAXIGRIP treated animals only showed a small immune response and animals treated with empty vesicles (i.e., without SFV2 peptides) showed no reactivity in ELISA. No IgG response was detected against rHA Malaysia in any of the animal groups (data not shown).

Figure 11:
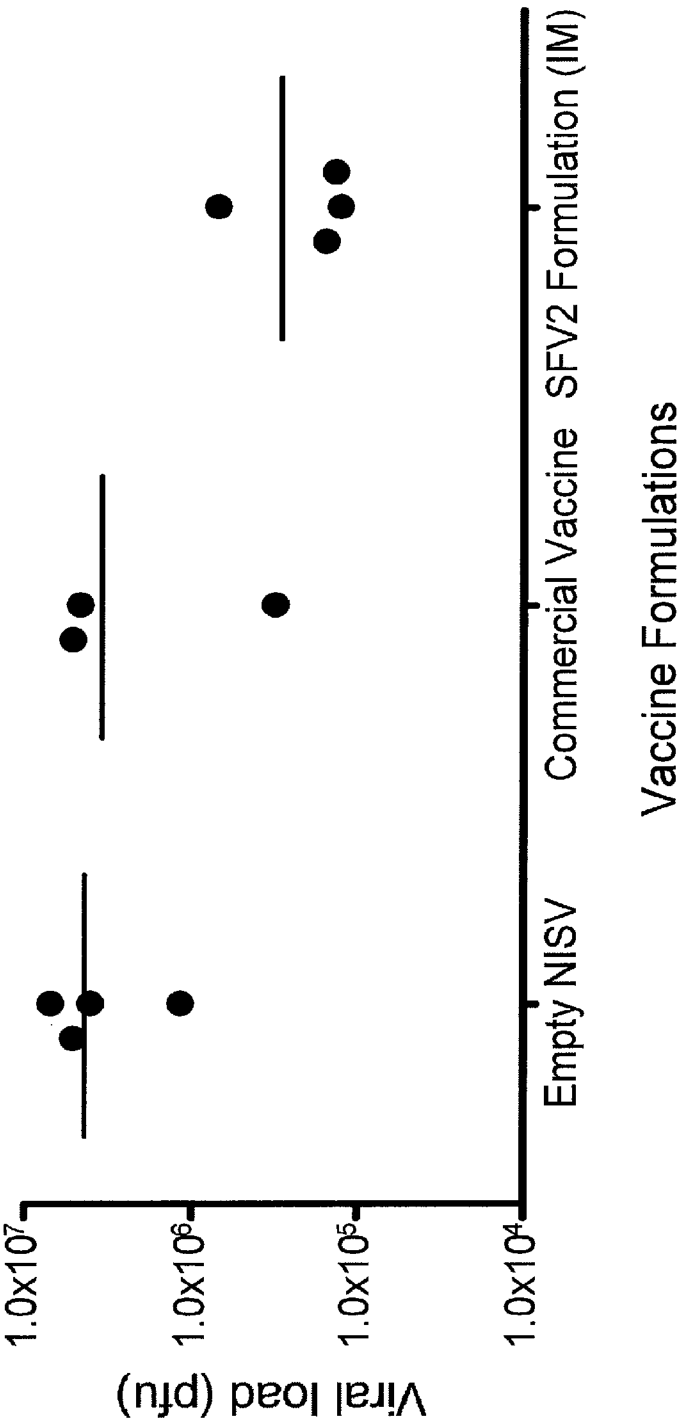
FIG. 11 shows viral load from nasal wash samples of ferrets immunized with peptide composition SFV2 administered intramuscularly and then subjected to viral challenge. Animals were inoculated with immunogenic peptide composition SFV2 and challenged with $2\times10^5$ pfu of H1N1 (A/Solomon Island/03/06) and viral load from nasal wash samples was measured by plaque assay at the peak of viremia (Day 2). Each symbol represents the viral load measured in an individual animal. Comparative data that was obtained with a commercial influenza vaccine (VAXIGRIP) are also provided.

As shown in FIG. 11, composition SFV2 given IM protects against viral challenge. Animals were inoculated with immunogenic peptide composition SFV2 of Example 12 and challenged with $2\times10^5$ pfu of H1N1 (A/Solomon Island/03/06) and viral load from nasal wash samples was measured by plaque assay at the peak of viremia (Day 2). Each symbol represents the viral load measured in an individual animal. The animals vaccinated with SFV2 exhibited a significantly reduced ($p<0.05$) viral load in nasal wash samples compared to control animals treated with empty vesicles. The commercial seasonal influenza vaccine which was also given by standard IM injection did not reduce viral load in nasal wash samples.

Figure 12:
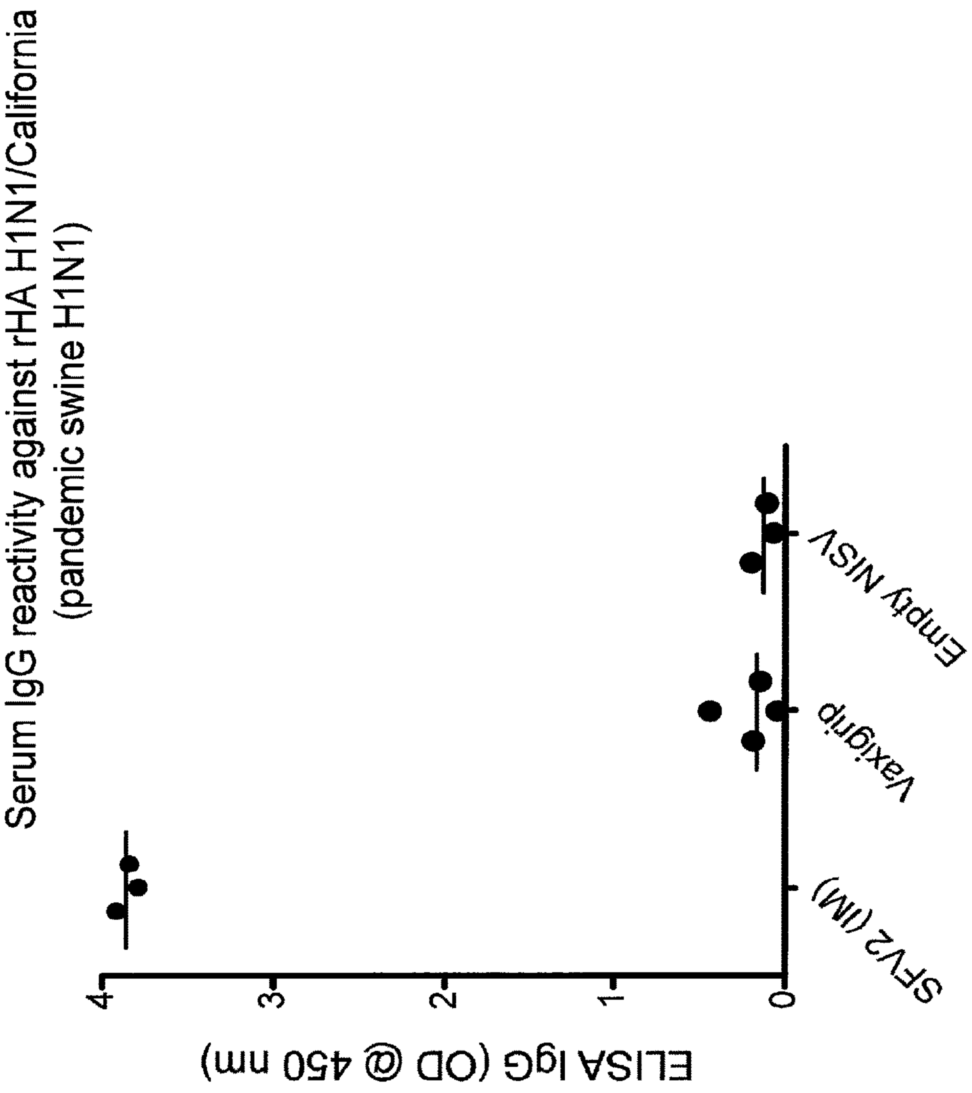
FIG. 12 shows humoral immunity against a potential pandemic strain of influenza in ferrets immunized with peptide composition SFV2 administered intramuscularly. Sera was collected from animals two weeks after the vaccination (prior to viral challenge) and samples were tested for reactivity with recombinant hemagglutinin (rHA) protein from the putative pandemic swine (H1N1/California/2009) isolate by ELISA. Comparative data that was obtained with a commercial influenza vaccine (VAXIGRIP) are also provided.

As shown in FIG. 12, composition SFV2 given IM induces humoral immunity against a potential pandemic strain of influenza. Sera was collected from animals two weeks after the second vaccination (prior to challenge) and samples were tested for reactivity with recombinant hemagglutinin (rHA) protein from the putative pandemic swine (H1N1/California/2009) isolate by ELISA. The animals vaccinated with SFV2 exhibited a higher serum IgG reactivity against rHA H1N1/California (pandemic swine H1N1) as compared to control animals treated with empty vesicles. The data in FIG. 12 shows that sera from animals vaccinated with the commercial seasonal influenza vaccine failed to react against this novel strain of influenza.

Example 14

Administration Scheme

This Example describes exemplary administration schemes using the vesicle SFV2 composition of Example 12 in humans. A partially-blinded, randomized, placebo-controlled study featuring the following treatment groups is performed:

- Treatment Group 1: two intramuscular injections corresponding to the antigen dose 1, vesicle SFV2 composition (1 mg peptide), given on Day 0 and Day 28 (n=50).
- Treatment Group 2: two intramuscular injections corresponding to dose 2, SFV2 (0.2 mg peptide) in combination with NAM1, given on Day 0 and Day 28 (n=50).
- Treatment Group 3: two intramuscular injections of phosphate buffered saline, placebo group, given on Day 0 and Day 28 (n=25).

Subjects are randomized in a 2:2:1 manner.

Short-term tolerability is assessed on day 7 post-administration. Spontaneously reported adverse events are collected for 28 days post-administration. Serious Adverse Events and Medically Significant Events are collected for a total follow up period of 168 days (±14 days). Biological safety is assessed before and after each injection and at the end of the 168 day follow up period.

Immunogenicity is assessed in serum samples collected on Day 0, Day 28 (±3 days), Day 56 (±7 days) and at the end of the 168 Day (±14 days) follow-up period. The immunological read-outs are serum HI antibodies (Hemagglutination Inhibition assay), rHA-specific serum IgG (ELISA), as well neutralizing antibodies determined by microneutralization assay. Regarding cellular (CTL) immunity evaluation, T-cell response is evaluated by ELISPOT and intracellular cytokine staining.

SEQUENCE LISTING

In accordance with 37 CFR 1.52(e)(5), a Sequence Listing filed herewith in the form of a text file (entitled "Sequence Listing.txt," created on Jun. 18, 2009, and 14 kilobytes) is incorporated herein by reference in its entirety.

OTHER EMBODIMENTS

Other embodiments of the invention will be apparent to those skilled in the art from a consideration of the specification or practice of the invention disclosed herein. It is intended that the specification and examples be considered as exemplary only, with the true scope of the invention being indicated by the following claims. The contents of any reference that is referred to herein are hereby incorporated by reference in their entirety.

What is claimed is:

1. An immunogenic composition comprising:
   - a peptide comprising the amino acid sequence of SEQ ID NO: 6;
   - a mixture of peptides comprising peptides that comprise all 16 of the amino acid sequences defined by SEQ ID NOs: 87-102; and
   - a peptide comprising the amino acid sequence of SEQ ID NO: 8.

2. An immunogenic composition comprising:
   - a peptide comprising the amino acid sequence of SEQ ID NO: 6;
   - a mixture of peptides comprising peptides that comprise all 16 of the amino acid sequences defined by SEQ ID NOs. 87-102;
   - a peptide comprising the amino acid sequence of SEQ ID NO. 12;
   - a peptide comprising the amino acid sequence of SEQ ID NO. 13; and
   - a mixture of peptides comprising peptides that comprise all 16 of the amino acid sequences defined by SEQ ID NOs: 103-118.

3. The composition of claim 1, wherein each peptide is immunogenic.

4. The composition of claim 1, wherein the composition further comprises an adjuvant.

5. The composition of claim 1, wherein at least one peptide is associated with a vesicle.

6. The composition of claim 5, wherein the vesicle comprises a non-ionic surfactant.

7. The composition of claim 6, wherein the vesicle comprises a transport enhancer which facilitates the transport of lipid-like molecules across mucosal membranes.

8. A method of inducing an immune response in an individual, the method comprising administering to the individual a therapeutically effective amount of the composition of claim 1.

9. An immunogenic composition according to claim 1, further comprising:
   - a TLR-3 agonist adjuvant; and
   - a vesicle which comprises a non-ionic surfactant and a transport enhancer which facilitates the transport of lipid-like molecules across mucosal membranes.

10. A method of inducing an immune response in an individual, the method comprising orally administering to the individual a therapeutically effective amount of the composition of claim 9.

11. An immunogenic composition according to claim 1, further comprising:
   - a TLR-4 agonist adjuvant; and
   - a vesicle which comprises a non-ionic surfactant.

12. A method of inducing an immune response in an individual, the method comprising parenterally administering to the individual a therapeutically effective amount of the composition of claim 11.

13. The composition of claim 2, wherein each peptide is immunogenic.

14. The composition of claim 2, wherein the composition further comprises an adjuvant.

15. The composition of claim 2, wherein at least one peptide is associated with a vesicle.

16. The composition of claim 15, wherein the vesicle comprises a non-ionic surfactant.

17. The composition of claim 16, wherein the vesicle comprises a transport enhancer which facilitates the transport of lipid-like molecules across mucosal membranes.

18. An immunogenic composition according to claim 2, further comprising:
   - a TLR-3 agonist adjuvant; and
   - a vesicle which comprises a non-ionic surfactant and a transport enhancer which facilitates the transport of lipid-like molecules across mucosal membranes.

19. An immunogenic composition according to claim 2, further comprising:
   - a TLR-4 agonist adjuvant; and
   - a vesicle which comprises a non-ionic surfactant.

20. A method of inducing an immune response in an individual, the method comprising administering to the individual a therapeutically effective amount of the composition of claim 2.

21. A method of inducing an immune response in an individual, the method comprising administering to the individual a therapeutically effective amount of the composition of claim 18.

22. A method of inducing an immune response in an individual, the method comprising administering to the individual a therapeutically effective amount of the composition of claim 19.

* * * * *

SEQUENCE LISTING

<160> NUMBER OF SEQ ID NOS: 134

<210> SEQ ID NO 1
<211> LENGTH: 28
<212> TYPE: PRT
<213> ORGANISM: Artificial Sequence
<220> FEATURE:
<223> OTHER INFORMATION: Immunogenic influenza peptide
<220> FEATURE:
<221> NAME/KEY: MISC_FEATURE
<222> LOCATION: (5)..(5)
<223> OTHER INFORMATION: Asp or Trp
<220> FEATURE:
<221> NAME/KEY: MISC_FEATURE
<222> LOCATION: (16)..(16)
<223> OTHER INFORMATION: Gly or Ser
<220> FEATURE:

```
<221> NAME/KEY: MISC_FEATURE
<222> LOCATION: (21)..(21)
<223> OTHER INFORMATION: Asp or Tyr

<400> SEQUENCE: 1

Gly Ser Arg Pro Xaa Val Arg Glu Asp Gly Gly Leu Pro Gln Ser Xaa
1               5                   10                  15

Arg Ile Ser Ile Xaa Trp Thr Ile Val Lys Pro Gly
            20                  25


<210> SEQ ID NO 2
<211> LENGTH: 26
<212> TYPE: PRT
<213> ORGANISM: Artificial Sequence
<220> FEATURE:
<223> OTHER INFORMATION: Immunogenic influenza peptide
<220> FEATURE:
<221> NAME/KEY: MISC_FEATURE
<222> LOCATION: (1)..(1)
<223> OTHER INFORMATION: Val or Thr
<220> FEATURE:
<221> NAME/KEY: MISC_FEATURE
<222> LOCATION: (13)..(13)
<223> OTHER INFORMATION: Lys or Glu
<220> FEATURE:
<221> NAME/KEY: MISC_FEATURE
<222> LOCATION: (18)..(18)
<223> OTHER INFORMATION: Arg or Lys

<400> SEQUENCE: 2

Xaa Thr Gly Val Ser Ala Ser Cys Ser His Asn Gly Xaa Ser Ser Phe
1               5                   10                  15

Tyr Xaa Asn Leu Leu Trp Leu Thr Gly Lys
            20                  25


<210> SEQ ID NO 3
<211> LENGTH: 33
<212> TYPE: PRT
<213> ORGANISM: Artificial Sequence
<220> FEATURE:
<223> OTHER INFORMATION: Immunogenic influenza peptide
<220> FEATURE:
<221> NAME/KEY: MISC_FEATURE
<222> LOCATION: (5)..(5)
<223> OTHER INFORMATION: Arg or Lys
<220> FEATURE:
<221> NAME/KEY: MISC_FEATURE
<222> LOCATION: (11)..(11)
<223> OTHER INFORMATION: Ala or Thr
<220> FEATURE:
<221> NAME/KEY: MISC_FEATURE
<222> LOCATION: (18)..(18)
<223> OTHER INFORMATION: Asp or Asn

<400> SEQUENCE: 3

His Tyr Ser Arg Xaa Phe Thr Pro Glu Ile Xaa Lys Arg Pro Lys Val
1               5                   10                  15

Arg Xaa Gln Glu Gly Arg Ile Asn Tyr Tyr Trp Thr Leu Leu Glu Pro
            20                  25                  30

Gly


<210> SEQ ID NO 4
<211> LENGTH: 30
<212> TYPE: PRT
<213> ORGANISM: Artificial Sequence
<220> FEATURE:
<223> OTHER INFORMATION: Immunogenic influenza peptide
<220> FEATURE:
<221> NAME/KEY: MISC_FEATURE
```

<222> LOCATION: (14)..(14)
<223> OTHER INFORMATION: Ala or Thr
<220> FEATURE:
<221> NAME/KEY: MISC_FEATURE
<222> LOCATION: (19)..(19)
<223> OTHER INFORMATION: Val or Ala

<400> SEQUENCE: 4

```
Pro Val Thr Ile Gly Glu Cys Pro Lys Tyr Val Arg Ser Xaa Lys Leu
1               5                   10                  15

Arg Met Xaa Thr Gly Leu Arg Asn Ile Pro Ser Ile Gln Ser
            20                  25                  30
```

<210> SEQ ID NO 5
<211> LENGTH: 29
<212> TYPE: PRT
<213> ORGANISM: Artificial Sequence
<220> FEATURE:
<223> OTHER INFORMATION: Immunogenic influenza peptide
<220> FEATURE:
<221> NAME/KEY: MISC_FEATURE
<222> LOCATION: (7)..(7)
<223> OTHER INFORMATION: Lys or Arg
<220> FEATURE:
<221> NAME/KEY: MISC_FEATURE
<222> LOCATION: (16)..(16)
<223> OTHER INFORMATION: Thr or Lys
<220> FEATURE:
<221> NAME/KEY: MISC_FEATURE
<222> LOCATION: (28)..(28)
<223> OTHER INFORMATION: Tyr or His

<400> SEQUENCE: 5

```
Cys Glu Leu Leu Ile Ser Xaa Glu Ser Trp Ser Tyr Ile Val Glu Xaa
1               5                   10                  15

Pro Asn Pro Glu Asn Gly Thr Cys Tyr Pro Gly Xaa Phe
            20                  25
```

<210> SEQ ID NO 6
<211> LENGTH: 88
<212> TYPE: PRT
<213> ORGANISM: Artificial Sequence
<220> FEATURE:
<223> OTHER INFORMATION: Immunogenic influenza peptide

<400> SEQUENCE: 6

```
Ser Trp Pro Asn His Thr Thr Thr Gly Val Ser Ala Ser Ser Ser His
1               5                   10                  15

Asn Gly Glu Ser Ser Phe Tyr Lys Asn Leu Leu Trp Leu Thr Gly Lys
            20                  25                  30

Asn Gly Leu Tyr Pro Asn Leu Ser Lys Ser Tyr Ala Asn Asn Lys Glu
        35                  40                  45

Lys Glu Val Leu Val Leu Trp Gly Val His His Pro Pro Asn Ile Gly
    50                  55                  60

Asp Gln Arg Ala Leu Tyr His Lys Glu Asn Ala Tyr Val Ser Val Val
65                  70                  75                  80

Ser Ile Ile Phe Glu Ala Asn Gly
                85
```

<210> SEQ ID NO 7
<211> LENGTH: 87
<212> TYPE: PRT
<213> ORGANISM: Artificial Sequence
<220> FEATURE:
<223> OTHER INFORMATION: Immunogenic influenza peptide

<400> SEQUENCE: 7

Asn Trp Thr Gly Val Thr Gln Asn Gly Thr Ser Ser Ser Ser Lys Arg
1 5 10 15

Arg Ser Asn Asn Ser Phe Phe Ser Arg Leu Asn Trp Leu Thr His Leu
20 25 30

Lys Phe Lys Tyr Pro Ala Leu Asn Thr Met Pro Asn Asn Glu Lys Phe
35 40 45

Asp Lys Leu Tyr Ile Trp Gly Val His His Pro Val Thr Asp Asn Asp
50 55 60

Gln Ile Phe Leu Tyr Ala Gln Ala Ser Gly Arg Ile Thr Val Ser Thr
65 70 75 80

Leu Leu Ile Asn Ser Thr Gly
85

<210> SEQ ID NO 8
<211> LENGTH: 98
<212> TYPE: PRT
<213> ORGANISM: Artificial Sequence
<220> FEATURE:
<223> OTHER INFORMATION: Immunogenic influenza peptide

<400> SEQUENCE: 8

Asn Ala Glu Lys Ala Pro Gly Gly Pro Tyr Lys Ile Gly Thr Ser Gly
1 5 10 15

Ser Ser Pro Asn Val Thr Asn Gly Asn Gly Phe Phe Ala Thr Met Ala
20 25 30

Trp Ala Val Pro Lys Asn Asp Asn Asn Lys Thr Ala Thr Asn Ser Leu
35 40 45

Thr Ile Glu Val Pro Tyr Ile Ser Thr Glu Gly Glu Asp Gln Ile Thr
50 55 60

Ile Trp Gly Phe His Ser Asp Asn Glu Thr Gln Met Ala Lys Leu Tyr
65 70 75 80

Gly Asp Ser Lys Pro Gln Lys Phe Thr Ser Ser Ala Gly Thr Ile Thr
85 90 95

Tyr Gln

<210> SEQ ID NO 9
<211> LENGTH: 21
<212> TYPE: PRT
<213> ORGANISM: Artificial Sequence
<220> FEATURE:
<223> OTHER INFORMATION: Immunogenic influenza peptide
<220> FEATURE:
<221> NAME/KEY: MISC_FEATURE
<222> LOCATION: (5)..(5)
<223> OTHER INFORMATION: Arg or Tyr
<220> FEATURE:
<221> NAME/KEY: MISC_FEATURE
<222> LOCATION: (18)..(18)
<223> OTHER INFORMATION: Lys or Ser
<220> FEATURE:
<221> NAME/KEY: MISC_FEATURE
<222> LOCATION: (19)..(19)
<223> OTHER INFORMATION: Val or Arg
<220> FEATURE:
<221> NAME/KEY: MISC_FEATURE
<222> LOCATION: (20)..(20)
<223> OTHER INFORMATION: Ser or Thr

<400> SEQUENCE: 9

Tyr Ala Cys Lys Xaa Gly Gly Lys Ser Ser Gly Ser Ser Tyr Pro Val
1 5 10 15

Leu Xaa Xaa Xaa Tyr
20

<210> SEQ ID NO 10
<211> LENGTH: 21
<212> TYPE: PRT
<213> ORGANISM: Artificial Sequence
<220> FEATURE:
<223> OTHER INFORMATION: Immunogenic influenza peptide
<220> FEATURE:
<221> NAME/KEY: MISC_FEATURE
<222> LOCATION: (5)..(5)
<223> OTHER INFORMATION: Arg or His
<220> FEATURE:
<221> NAME/KEY: MISC_FEATURE
<222> LOCATION: (18)..(18)
<223> OTHER INFORMATION: Asn or Ser
<220> FEATURE:
<221> NAME/KEY: MISC_FEATURE
<222> LOCATION: (20)..(20)
<223> OTHER INFORMATION: Ser or Thr
<220> FEATURE:
<221> NAME/KEY: MISC_FEATURE
<222> LOCATION: (21)..(21)
<223> OTHER INFORMATION: Tyr or Met

<400> SEQUENCE: 10

Tyr Ala Cys Lys Xaa Gly Gly Lys Ser Ser Gly Ser Ser Tyr Pro Val
1 5 10 15

Leu Xaa Val Xaa Xaa
20

<210> SEQ ID NO 11
<211> LENGTH: 21
<212> TYPE: PRT
<213> ORGANISM: Artificial Sequence
<220> FEATURE:
<223> OTHER INFORMATION: Immunogenic influenza peptide
<220> FEATURE:
<221> NAME/KEY: MISC_FEATURE
<222> LOCATION: (5)..(5)
<223> OTHER INFORMATION: Arg or His
<220> FEATURE:
<221> NAME/KEY: MISC_FEATURE
<222> LOCATION: (18)..(18)
<223> OTHER INFORMATION: Asn or Ser
<220> FEATURE:
<221> NAME/KEY: MISC_FEATURE
<222> LOCATION: (20)..(20)
<223> OTHER INFORMATION: Ser or Thr
<220> FEATURE:
<221> NAME/KEY: MISC_FEATURE
<222> LOCATION: (21)..(21)
<223> OTHER INFORMATION: Tyr or Met

<400> SEQUENCE: 11

Tyr Ala Ser Lys Xaa Gly Gly Lys Ser Ser Gly Ser Ser Tyr Pro Val
1 5 10 15

Leu Xaa Val Xaa Xaa
20

<210> SEQ ID NO 12
<211> LENGTH: 48
<212> TYPE: PRT
<213> ORGANISM: Artificial Sequence
<220> FEATURE:
<223> OTHER INFORMATION: Immunogenic influenza peptide

<400> SEQUENCE: 12

Ala Glu Lys Ala Pro Gly Gly Pro Tyr Lys Ile Gly Thr Ser Gly Ser
1 5 10 15

Ser Pro Asn Val Thr Asn Gly Asn Gly Phe Phe Ala Thr Met Ala Trp
20 25 30

Ala Val Pro Lys Asn Asp Asn Asn Lys Thr Ala Thr Asn Ser Leu Thr
35 40 45

<210> SEQ ID NO 13
<211> LENGTH: 54
<212> TYPE: PRT
<213> ORGANISM: Artificial Sequence
<220> FEATURE:
<223> OTHER INFORMATION: Immunogenic influenza peptide

<400> SEQUENCE: 13

Phe His Ser Asp Asn Glu Thr Gln Met Ala Lys Leu Tyr Gly Asp Ser
1 5 10 15

Lys Pro Gln Lys Phe Thr Ser Ser Ala Asn Gly Val Thr Thr His Tyr
20 25 30

Val Ser Gln Ile Gly Gly Phe Pro Asn Gln Thr Glu Asp Gly Gly Leu
35 40 45

Pro Gln Ser Gly Arg Ile
50

<210> SEQ ID NO 14
<211> LENGTH: 15
<212> TYPE: PRT
<213> ORGANISM: Artificial Sequence
<220> FEATURE:
<223> OTHER INFORMATION: Immunogenic influenza peptide
<220> FEATURE:
<221> NAME/KEY: MISC_FEATURE
<222> LOCATION: (9)..(9)
<223> OTHER INFORMATION: Glu or Asp
<220> FEATURE:
<221> NAME/KEY: MISC_FEATURE
<222> LOCATION: (10)..(10)
<223> OTHER INFORMATION: Lys or Arg
<220> FEATURE:
<221> NAME/KEY: MISC_FEATURE
<222> LOCATION: (11)..(11)
<223> OTHER INFORMATION: Ser or Thr
<220> FEATURE:
<221> NAME/KEY: MISC_FEATURE
<222> LOCATION: (13)..(13)
<223> OTHER INFORMATION: Val or Ile

<400> SEQUENCE: 14

Ser Val Gln Arg Asn Leu Pro Phe Xaa Xaa Xaa Thr Xaa Met Ala
1 5 10 15

<210> SEQ ID NO 15
<211> LENGTH: 16
<212> TYPE: PRT
<213> ORGANISM: Artificial Sequence
<220> FEATURE:
<223> OTHER INFORMATION: Immunogenic influenza peptide
<220> FEATURE:
<221> NAME/KEY: MISC_FEATURE
<222> LOCATION: (1)..(1)
<223> OTHER INFORMATION: Asn or Ala
<220> FEATURE:
<221> NAME/KEY: MISC_FEATURE
<222> LOCATION: (2)..(2)
<223> OTHER INFORMATION: Met or Ile
<220> FEATURE:
<221> NAME/KEY: MISC_FEATURE
<222> LOCATION: (3)..(3)
<223> OTHER INFORMATION: Gly or Glu
<220> FEATURE:
<221> NAME/KEY: MISC_FEATURE
<222> LOCATION: (12)..(12)
<223> OTHER INFORMATION: Gly or Arg

<400> SEQUENCE: 15

Xaa Xaa Xaa Ser Ser Thr Leu Glu Leu Arg Ser Xaa Tyr Trp Ala Ile
1 5 10 15

<210> SEQ ID NO 16
<211> LENGTH: 180
<212> TYPE: PRT
<213> ORGANISM: Artificial Sequence
<220> FEATURE:
<223> OTHER INFORMATION: Immunogenic influenza peptide

<400> SEQUENCE: 16

Cys Glu Leu Leu Ile Ser Arg Glu Ser Trp Ser Tyr Ile Val Glu Lys
1 5 10 15

Pro Asn Pro Glu Asn Gly Thr Cys Tyr Pro Gly His Phe Ser Trp Pro
20 25 30

Asn His Thr Thr Thr Gly Val Ser Ala Ser Cys Ser His Asn Gly Glu
35 40 45

Ser Ser Phe Tyr Lys Asn Leu Leu Trp Leu Thr Gly Lys Asn Gly Leu
50 55 60

Tyr Pro Asn Leu Ser Lys Ser Tyr Ala Asn Asn Lys Glu Lys Glu Val
65 70 75 80

Leu Val Leu Trp Gly Val His His Pro Pro Asn Ile Gly Asp Gln Arg
85 90 95

Ala Leu Tyr His Lys Glu Asn Ala Tyr Val Ser Val Val Ser His Tyr
100 105 110

Ser Arg Lys Phe Thr Pro Glu Ile Ala Lys Arg Pro Lys Val Arg Asp
115 120 125

Gln Glu Gly Arg Ile Asn Tyr Tyr Trp Thr Leu Leu Glu Pro Gly Ile
130 135 140

Ile Phe Glu Ala Asn Gly Pro Val Thr Ile Gly Glu Cys Pro Lys Tyr
145 150 155 160

Val Arg Ser Ala Lys Leu Arg Met Val Thr Gly Leu Arg Asn Ile Pro
165 170 175

Ser Ile Gln Ser
180

<210> SEQ ID NO 17
<211> LENGTH: 21
<212> TYPE: PRT
<213> ORGANISM: Artificial Sequence
<220> FEATURE:
<223> OTHER INFORMATION: Immunogenic influenza peptide
<220> FEATURE:
<221> NAME/KEY: MISC_FEATURE
<222> LOCATION: (3)..(3)
<223> OTHER INFORMATION: Ser or Cys
<220> FEATURE:
<221> NAME/KEY: MISC_FEATURE
<222> LOCATION: (5)..(5)
<223> OTHER INFORMATION: Arg, His or Tyr
<220> FEATURE:
<221> NAME/KEY: MISC_FEATURE
<222> LOCATION: (18)..(18)
<223> OTHER INFORMATION: Asn, Ser or Lys
<220> FEATURE:
<221> NAME/KEY: MISC_FEATURE
<222> LOCATION: (19)..(19)
<223> OTHER INFORMATION: Val or Ser
<220> FEATURE:
<221> NAME/KEY: MISC_FEATURE
<222> LOCATION: (20)..(20)
<223> OTHER INFORMATION: Ser or Thr
<220> FEATURE:
<221> NAME/KEY: MISC_FEATURE
<222> LOCATION: (21)..(21)
<223> OTHER INFORMATION: Tyr or Met

<400> SEQUENCE: 17

```
Tyr Ala Xaa Lys Xaa Gly Gly Lys Ser Ser Gly Ser Ser Tyr Pro Val
1               5                   10                  15

Leu Xaa Xaa Xaa Xaa
            20
```

<210> SEQ ID NO 18
<211> LENGTH: 127
<212> TYPE: PRT
<213> ORGANISM: Artificial Sequence
<220> FEATURE:
<223> OTHER INFORMATION: Immunogenic influenza peptide

<400> SEQUENCE: 18

```
Asn Ala Glu Lys Ala Pro Gly Gly Pro Tyr Lys Ile Gly Thr Ser Gly
1               5                   10                  15

Ser Ser Pro Asn Val Thr Asn Gly Asn Gly Phe Phe Ala Thr Met Ala
            20                  25                  30

Trp Ala Val Pro Lys Asn Asp Asn Asn Lys Thr Ala Thr Asn Ser Leu
        35                  40                  45

Thr Ile Glu Val Pro Tyr Ile Ser Thr Glu Gly Glu Asp Gln Ile Thr
    50                  55                  60

Ile Trp Gly Phe His Ser Asp Asn Glu Thr Gln Met Ala Lys Leu Tyr
65                  70                  75                  80

Gly Asp Ser Lys Pro Gln Lys Phe Thr Ser Ser Ala Asn Gly Val Thr
                85                  90                  95

Thr His Tyr Val Ser Gln Ile Gly Gly Phe Pro Asn Gln Thr Glu Asp
            100                 105                 110

Gly Gly Leu Pro Gln Ser Gly Arg Ile Gly Thr Ile Thr Tyr Gln
        115                 120                 125
```

<210> SEQ ID NO 19
<211> LENGTH: 28
<212> TYPE: PRT
<213> ORGANISM: Artificial Sequence
<220> FEATURE:
<223> OTHER INFORMATION: Immunogenic influenza peptide

<400> SEQUENCE: 19

```
Gly Ser Arg Pro Asp Val Arg Glu Asp Gly Gly Leu Pro Gln Ser Gly
1               5                   10                  15

Arg Ile Ser Ile Asp Trp Thr Ile Val Lys Pro Gly
            20                  25
```

<210> SEQ ID NO 20
<211> LENGTH: 28
<212> TYPE: PRT
<213> ORGANISM: Artificial Sequence
<220> FEATURE:
<223> OTHER INFORMATION: Immunogenic influenza peptide

<400> SEQUENCE: 20

```
Gly Ser Arg Pro Asp Val Arg Glu Asp Gly Gly Leu Pro Gln Ser Gly
1               5                   10                  15

Arg Ile Ser Ile Tyr Trp Thr Ile Val Lys Pro Gly
```

20 25

<210> SEQ ID NO 21
<211> LENGTH: 28
<212> TYPE: PRT
<213> ORGANISM: Artificial Sequence
<220> FEATURE:
<223> OTHER INFORMATION: Immunogenic influenza peptide

<400> SEQUENCE: 21

Gly Ser Arg Pro Asp Val Arg Glu Asp Gly Gly Leu Pro Gln Ser Ser
1 5 10 15

Arg Ile Ser Ile Asp Trp Thr Ile Val Lys Pro Gly
20 25

<210> SEQ ID NO 22
<211> LENGTH: 28
<212> TYPE: PRT
<213> ORGANISM: Artificial Sequence
<220> FEATURE:
<223> OTHER INFORMATION: Immunogenic influenza peptide

<400> SEQUENCE: 22

Gly Ser Arg Pro Asp Val Arg Glu Asp Gly Gly Leu Pro Gln Ser Ser
1 5 10 15

Arg Ile Ser Ile Tyr Trp Thr Ile Val Lys Pro Gly
20 25

<210> SEQ ID NO 23
<211> LENGTH: 28
<212> TYPE: PRT
<213> ORGANISM: Artificial Sequence
<220> FEATURE:
<223> OTHER INFORMATION: Immunogenic influenza peptide

<400> SEQUENCE: 23

Gly Ser Arg Pro Trp Val Arg Glu Asp Gly Gly Leu Pro Gln Ser Gly
1 5 10 15

Arg Ile Ser Ile Asp Trp Thr Ile Val Lys Pro Gly
20 25

<210> SEQ ID NO 24
<211> LENGTH: 28
<212> TYPE: PRT
<213> ORGANISM: Artificial Sequence
<220> FEATURE:
<223> OTHER INFORMATION: Immunogenic influenza peptide

<400> SEQUENCE: 24

Gly Ser Arg Pro Trp Val Arg Glu Asp Gly Gly Leu Pro Gln Ser Gly
1 5 10 15

Arg Ile Ser Ile Tyr Trp Thr Ile Val Lys Pro Gly
20 25

<210> SEQ ID NO 25
<211> LENGTH: 28
<212> TYPE: PRT
<213> ORGANISM: Artificial Sequence
<220> FEATURE:
<223> OTHER INFORMATION: Immunogenic influenza peptide

<400> SEQUENCE: 25

Gly Ser Arg Pro Trp Val Arg Glu Asp Gly Gly Leu Pro Gln Ser Ser
1 5 10 15

```
Arg Ile Ser Ile Asp Trp Thr Ile Val Lys Pro Gly
            20                  25


<210> SEQ ID NO 26
<211> LENGTH: 28
<212> TYPE: PRT
<213> ORGANISM: Artificial Sequence
<220> FEATURE:
<223> OTHER INFORMATION: Immunogenic influenza peptide

<400> SEQUENCE: 26

Gly Ser Arg Pro Trp Val Arg Glu Asp Gly Gly Leu Pro Gln Ser Ser
1               5                   10                  15

Arg Ile Ser Ile Tyr Trp Thr Ile Val Lys Pro Gly
            20                  25


<210> SEQ ID NO 27
<211> LENGTH: 26
<212> TYPE: PRT
<213> ORGANISM: Artificial Sequence
<220> FEATURE:
<223> OTHER INFORMATION: Immunogenic influenza peptide

<400> SEQUENCE: 27

Val Thr Gly Val Ser Ala Ser Cys Ser His Asn Gly Lys Ser Ser Phe
1               5                   10                  15

Tyr Arg Asn Leu Leu Trp Leu Thr Gly Lys
            20                  25


<210> SEQ ID NO 28
<211> LENGTH: 26
<212> TYPE: PRT
<213> ORGANISM: Artificial Sequence
<220> FEATURE:
<223> OTHER INFORMATION: Immunogenic influenza peptide

<400> SEQUENCE: 28

Val Thr Gly Val Ser Ala Ser Cys Ser His Asn Gly Lys Ser Ser Phe
1               5                   10                  15

Tyr Lys Asn Leu Leu Trp Leu Thr Gly Lys
            20                  25


<210> SEQ ID NO 29
<211> LENGTH: 26
<212> TYPE: PRT
<213> ORGANISM: Artificial Sequence
<220> FEATURE:
<223> OTHER INFORMATION: Immunogenic influenza peptide

<400> SEQUENCE: 29

Val Thr Gly Val Ser Ala Ser Cys Ser His Asn Gly Glu Ser Ser Phe
1               5                   10                  15

Tyr Arg Asn Leu Leu Trp Leu Thr Gly Lys
            20                  25


<210> SEQ ID NO 30
<211> LENGTH: 26
<212> TYPE: PRT
<213> ORGANISM: Artificial Sequence
<220> FEATURE:
<223> OTHER INFORMATION: Immunogenic influenza peptide

<400> SEQUENCE: 30

Val Thr Gly Val Ser Ala Ser Cys Ser His Asn Gly Glu Ser Ser Phe
1               5                   10                  15
```

Tyr Lys Asn Leu Leu Trp Leu Thr Gly Lys
20 25

<210> SEQ ID NO 31
<211> LENGTH: 26
<212> TYPE: PRT
<213> ORGANISM: Artificial Sequence
<220> FEATURE:
<223> OTHER INFORMATION: Immunogenic influenza peptide

<400> SEQUENCE: 31

Thr Thr Gly Val Ser Ala Ser Cys Ser His Asn Gly Lys Ser Ser Phe
1 5 10 15

Tyr Arg Asn Leu Leu Trp Leu Thr Gly Lys
20 25

<210> SEQ ID NO 32
<211> LENGTH: 26
<212> TYPE: PRT
<213> ORGANISM: Artificial Sequence
<220> FEATURE:
<223> OTHER INFORMATION: Immunogenic influenza peptide

<400> SEQUENCE: 32

Thr Thr Gly Val Ser Ala Ser Cys Ser His Asn Gly Lys Ser Ser Phe
1 5 10 15

Tyr Lys Asn Leu Leu Trp Leu Thr Gly Lys
20 25

<210> SEQ ID NO 33
<211> LENGTH: 26
<212> TYPE: PRT
<213> ORGANISM: Artificial Sequence
<220> FEATURE:
<223> OTHER INFORMATION: Immunogenic influenza peptide

<400> SEQUENCE: 33

Thr Thr Gly Val Ser Ala Ser Cys Ser His Asn Gly Glu Ser Ser Phe
1 5 10 15

Tyr Arg Asn Leu Leu Trp Leu Thr Gly Lys
20 25

<210> SEQ ID NO 34
<211> LENGTH: 26
<212> TYPE: PRT
<213> ORGANISM: Artificial Sequence
<220> FEATURE:
<223> OTHER INFORMATION: Immunogenic influenza peptide

<400> SEQUENCE: 34

Thr Thr Gly Val Ser Ala Ser Cys Ser His Asn Gly Glu Ser Ser Phe
1 5 10 15

Tyr Lys Asn Leu Leu Trp Leu Thr Gly Lys
20 25

<210> SEQ ID NO 35
<211> LENGTH: 33
<212> TYPE: PRT
<213> ORGANISM: Artificial Sequence
<220> FEATURE:
<223> OTHER INFORMATION: Immunogenic influenza peptide

<400> SEQUENCE: 35

His Tyr Ser Arg Arg Phe Thr Pro Glu Ile Ala Lys Arg Pro Lys Val

-continued

```
1               5                   10                  15

Arg Asp Gln Glu Gly Arg Ile Asn Tyr Tyr Trp Thr Leu Leu Glu Pro
            20                  25                  30

Gly


<210> SEQ ID NO 36
<211> LENGTH: 33
<212> TYPE: PRT
<213> ORGANISM: Artificial Sequence
<220> FEATURE:
<223> OTHER INFORMATION: Immunogenic influenza peptide

<400> SEQUENCE: 36

His Tyr Ser Arg Arg Phe Thr Pro Glu Ile Ala Lys Arg Pro Lys Val
1               5                   10                  15

Arg Asn Gln Glu Gly Arg Ile Asn Tyr Tyr Trp Thr Leu Leu Glu Pro
            20                  25                  30

Gly


<210> SEQ ID NO 37
<211> LENGTH: 33
<212> TYPE: PRT
<213> ORGANISM: Artificial Sequence
<220> FEATURE:
<223> OTHER INFORMATION: Immunogenic influenza peptide

<400> SEQUENCE: 37

His Tyr Ser Arg Arg Phe Thr Pro Glu Ile Thr Lys Arg Pro Lys Val
1               5                   10                  15

Arg Asp Gln Glu Gly Arg Ile Asn Tyr Tyr Trp Thr Leu Leu Glu Pro
            20                  25                  30

Gly


<210> SEQ ID NO 38
<211> LENGTH: 33
<212> TYPE: PRT
<213> ORGANISM: Artificial Sequence
<220> FEATURE:
<223> OTHER INFORMATION: Immunogenic influenza peptide

<400> SEQUENCE: 38

His Tyr Ser Arg Arg Phe Thr Pro Glu Ile Thr Lys Arg Pro Lys Val
1               5                   10                  15

Arg Asn Gln Glu Gly Arg Ile Asn Tyr Tyr Trp Thr Leu Leu Glu Pro
            20                  25                  30

Gly


<210> SEQ ID NO 39
<211> LENGTH: 33
<212> TYPE: PRT
<213> ORGANISM: Artificial Sequence
<220> FEATURE:
<223> OTHER INFORMATION: Immunogenic influenza peptide

<400> SEQUENCE: 39

His Tyr Ser Arg Lys Phe Thr Pro Glu Ile Ala Lys Arg Pro Lys Val
1               5                   10                  15

Arg Asp Gln Glu Gly Arg Ile Asn Tyr Tyr Trp Thr Leu Leu Glu Pro
            20                  25                  30

Gly
```

<210> SEQ ID NO 40
<211> LENGTH: 33
<212> TYPE: PRT
<213> ORGANISM: Artificial Sequence
<220> FEATURE:
<223> OTHER INFORMATION: Immunogenic influenza peptide

<400> SEQUENCE: 40

```
His Tyr Ser Arg Lys Phe Thr Pro Glu Ile Ala Lys Arg Pro Lys Val
1               5                   10                  15

Arg Asn Gln Glu Gly Arg Ile Asn Tyr Tyr Trp Thr Leu Leu Glu Pro
            20                  25                  30

Gly
```

<210> SEQ ID NO 41
<211> LENGTH: 33
<212> TYPE: PRT
<213> ORGANISM: Artificial Sequence
<220> FEATURE:
<223> OTHER INFORMATION: Immunogenic influenza peptide

<400> SEQUENCE: 41

```
His Tyr Ser Arg Lys Phe Thr Pro Glu Ile Thr Lys Arg Pro Lys Val
1               5                   10                  15

Arg Asp Gln Glu Gly Arg Ile Asn Tyr Tyr Trp Thr Leu Leu Glu Pro
            20                  25                  30

Gly
```

<210> SEQ ID NO 42
<211> LENGTH: 33
<212> TYPE: PRT
<213> ORGANISM: Artificial Sequence
<220> FEATURE:
<223> OTHER INFORMATION: Immunogenic influenza peptide

<400> SEQUENCE: 42

```
His Tyr Ser Arg Lys Phe Thr Pro Glu Ile Thr Lys Arg Pro Lys Val
1               5                   10                  15

Arg Asn Gln Glu Gly Arg Ile Asn Tyr Tyr Trp Thr Leu Leu Glu Pro
            20                  25                  30

Gly
```

<210> SEQ ID NO 43
<211> LENGTH: 30
<212> TYPE: PRT
<213> ORGANISM: Artificial Sequence
<220> FEATURE:
<223> OTHER INFORMATION: Immunogenic influenza peptide

<400> SEQUENCE: 43

```
Pro Val Thr Ile Gly Glu Cys Pro Lys Tyr Val Arg Ser Ala Lys Leu
1               5                   10                  15

Arg Met Val Thr Gly Leu Arg Asn Ile Pro Ser Ile Gln Ser
            20                  25                  30
```

<210> SEQ ID NO 44
<211> LENGTH: 30
<212> TYPE: PRT
<213> ORGANISM: Artificial Sequence
<220> FEATURE:
<223> OTHER INFORMATION: Immunogenic influenza peptide

<400> SEQUENCE: 44

Pro Val Thr Ile Gly Glu Cys Pro Lys Tyr Val Arg Ser Ala Lys Leu
1 5 10 15

Arg Met Ala Thr Gly Leu Arg Asn Ile Pro Ser Ile Gln Ser
20 25 30

<210> SEQ ID NO 45
<211> LENGTH: 30
<212> TYPE: PRT
<213> ORGANISM: Artificial Sequence
<220> FEATURE:
<223> OTHER INFORMATION: Immunogenic influenza peptide

<400> SEQUENCE: 45

Pro Val Thr Ile Gly Glu Cys Pro Lys Tyr Val Arg Ser Thr Lys Leu
1 5 10 15

Arg Met Val Thr Gly Leu Arg Asn Ile Pro Ser Ile Gln Ser
20 25 30

<210> SEQ ID NO 46
<211> LENGTH: 30
<212> TYPE: PRT
<213> ORGANISM: Artificial Sequence
<220> FEATURE:
<223> OTHER INFORMATION: Immunogenic influenza peptide

<400> SEQUENCE: 46

Pro Val Thr Ile Gly Glu Cys Pro Lys Tyr Val Arg Ser Thr Lys Leu
1 5 10 15

Arg Met Ala Thr Gly Leu Arg Asn Ile Pro Ser Ile Gln Ser
20 25 30

<210> SEQ ID NO 47
<211> LENGTH: 29
<212> TYPE: PRT
<213> ORGANISM: Artificial Sequence
<220> FEATURE:
<223> OTHER INFORMATION: Immunogenic influenza peptide

<400> SEQUENCE: 47

Cys Glu Leu Leu Ile Ser Lys Glu Ser Trp Ser Tyr Ile Val Glu Thr
1 5 10 15

Pro Asn Pro Glu Asn Gly Thr Cys Tyr Pro Gly Tyr Phe
20 25

<210> SEQ ID NO 48
<211> LENGTH: 29
<212> TYPE: PRT
<213> ORGANISM: Artificial Sequence
<220> FEATURE:
<223> OTHER INFORMATION: Immunogenic influenza peptide

<400> SEQUENCE: 48

Cys Glu Leu Leu Ile Ser Lys Glu Ser Trp Ser Tyr Ile Val Glu Thr
1 5 10 15

Pro Asn Pro Glu Asn Gly Thr Cys Tyr Pro Gly His Phe
20 25

<210> SEQ ID NO 49
<211> LENGTH: 29
<212> TYPE: PRT
<213> ORGANISM: Artificial Sequence
<220> FEATURE:
<223> OTHER INFORMATION: Immunogenic influenza peptide

<400> SEQUENCE: 49

Cys Glu Leu Leu Ile Ser Lys Glu Ser Trp Ser Tyr Ile Val Glu Lys
1 5 10 15

Pro Asn Pro Glu Asn Gly Thr Cys Tyr Pro Gly Tyr Phe
20 25

<210> SEQ ID NO 50
<211> LENGTH: 29
<212> TYPE: PRT
<213> ORGANISM: Artificial Sequence
<220> FEATURE:
<223> OTHER INFORMATION: Immunogenic influenza peptide

<400> SEQUENCE: 50

Cys Glu Leu Leu Ile Ser Lys Glu Ser Trp Ser Tyr Ile Val Glu Lys
1 5 10 15

Pro Asn Pro Glu Asn Gly Thr Cys Tyr Pro Gly His Phe
20 25

<210> SEQ ID NO 51
<211> LENGTH: 29
<212> TYPE: PRT
<213> ORGANISM: Artificial Sequence
<220> FEATURE:
<223> OTHER INFORMATION: Immunogenic influenza peptide

<400> SEQUENCE: 51

Cys Glu Leu Leu Ile Ser Arg Glu Ser Trp Ser Tyr Ile Val Glu Thr
1 5 10 15

Pro Asn Pro Glu Asn Gly Thr Cys Tyr Pro Gly Tyr Phe
20 25

<210> SEQ ID NO 52
<211> LENGTH: 29
<212> TYPE: PRT
<213> ORGANISM: Artificial Sequence
<220> FEATURE:
<223> OTHER INFORMATION: Immunogenic influenza peptide

<400> SEQUENCE: 52

Cys Glu Leu Leu Ile Ser Arg Glu Ser Trp Ser Tyr Ile Val Glu Thr
1 5 10 15

Pro Asn Pro Glu Asn Gly Thr Cys Tyr Pro Gly His Phe
20 25

<210> SEQ ID NO 53
<211> LENGTH: 29
<212> TYPE: PRT
<213> ORGANISM: Artificial Sequence
<220> FEATURE:
<223> OTHER INFORMATION: Immunogenic influenza peptide

<400> SEQUENCE: 53

Cys Glu Leu Leu Ile Ser Arg Glu Ser Trp Ser Tyr Ile Val Glu Lys
1 5 10 15

Pro Asn Pro Glu Asn Gly Thr Cys Tyr Pro Gly Tyr Phe
20 25

<210> SEQ ID NO 54
<211> LENGTH: 29
<212> TYPE: PRT
<213> ORGANISM: Artificial Sequence
<220> FEATURE:
<223> OTHER INFORMATION: Immunogenic influenza peptide

<400> SEQUENCE: 54

Cys Glu Leu Leu Ile Ser Arg Glu Ser Trp Ser Tyr Ile Val Glu Lys
1 5 10 15

Pro Asn Pro Glu Asn Gly Thr Cys Tyr Pro Gly His Phe
20 25

<210> SEQ ID NO 55
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 55

Tyr Ala Cys Lys Arg Gly Gly Lys Ser Ser Gly Ser Ser Tyr Pro Val
1 5 10 15

Leu Lys Val Ser Tyr
20

<210> SEQ ID NO 56
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 56

Tyr Ala Cys Lys Arg Gly Gly Lys Ser Ser Gly Ser Ser Tyr Pro Val
1 5 10 15

Leu Lys Val Thr Tyr
20

<210> SEQ ID NO 57
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 57

Tyr Ala Cys Lys Arg Gly Gly Lys Ser Ser Gly Ser Ser Tyr Pro Val
1 5 10 15

Leu Lys Arg Ser Tyr
20

<210> SEQ ID NO 58
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 58

Tyr Ala Cys Lys Arg Gly Gly Lys Ser Ser Gly Ser Ser Tyr Pro Val
1 5 10 15

Leu Lys Arg Thr Tyr
20

<210> SEQ ID NO 59
<211> LENGTH: 21
<212> TYPE: PRT
<213> ORGANISM: Artificial Sequence
<220> FEATURE:

<223> OTHER INFORMATION: Immunogenic influenza peptide

<400> SEQUENCE: 59

```
Tyr Ala Cys Lys Arg Gly Gly Lys Ser Ser Gly Ser Ser Tyr Pro Val
1               5                   10                  15

Leu Ser Val Ser Tyr
            20
```

<210> SEQ ID NO 60
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 60

```
Tyr Ala Cys Lys Arg Gly Gly Lys Ser Ser Gly Ser Ser Tyr Pro Val
1               5                   10                  15

Leu Ser Val Thr Tyr
            20
```

<210> SEQ ID NO 61
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 61

```
Tyr Ala Cys Lys Arg Gly Gly Lys Ser Ser Gly Ser Ser Tyr Pro Val
1               5                   10                  15

Leu Ser Arg Ser Tyr
            20
```

<210> SEQ ID NO 62
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 62

```
Tyr Ala Cys Lys Arg Gly Gly Lys Ser Ser Gly Ser Ser Tyr Pro Val
1               5                   10                  15

Leu Ser Arg Thr Tyr
            20
```

<210> SEQ ID NO 63
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 63

```
Tyr Ala Cys Lys Tyr Gly Gly Lys Ser Ser Gly Ser Ser Tyr Pro Val
1               5                   10                  15

Leu Lys Val Ser Tyr
            20
```

<210> SEQ ID NO 64
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 64

Tyr Ala Cys Lys Tyr Gly Gly Lys Ser Ser Gly Ser Ser Tyr Pro Val
1               5                   10                  15

Leu Lys Val Thr Tyr
            20

<210> SEQ ID NO 65
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 65

Tyr Ala Cys Lys Tyr Gly Gly Lys Ser Ser Gly Ser Ser Tyr Pro Val
1               5                   10                  15

Leu Lys Arg Ser Tyr
            20

<210> SEQ ID NO 66
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 66

Tyr Ala Cys Lys Tyr Gly Gly Lys Ser Ser Gly Ser Ser Tyr Pro Val
1               5                   10                  15

Leu Lys Arg Thr Tyr
            20

<210> SEQ ID NO 67
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 67

Tyr Ala Cys Lys Tyr Gly Gly Lys Ser Ser Gly Ser Ser Tyr Pro Val
1               5                   10                  15

Leu Ser Val Ser Tyr
            20

<210> SEQ ID NO 68
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 68

Tyr Ala Cys Lys Tyr Gly Gly Lys Ser Ser Gly Ser Ser Tyr Pro Val
1               5                   10                  15

Leu Ser Val Thr Tyr
            20

<210> SEQ ID NO 69
<211> LENGTH: 21
<212> TYPE: PRT

-continued

<213> ORGANISM: Artificial Sequence
<220> FEATURE:
<223> OTHER INFORMATION: Immunogenic influenza peptide

<400> SEQUENCE: 69

Tyr Ala Cys Lys Tyr Gly Gly Lys Ser Ser Gly Ser Ser Tyr Pro Val
1 5 10 15

Leu Ser Arg Ser Tyr
20

<210> SEQ ID NO 70
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 70

Tyr Ala Cys Lys Tyr Gly Gly Lys Ser Ser Gly Ser Ser Tyr Pro Val
1 5 10 15

Leu Ser Arg Thr Tyr
20

<210> SEQ ID NO 71
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 71

Tyr Ala Cys Lys Arg Gly Gly Lys Ser Ser Gly Ser Ser Tyr Pro Val
1 5 10 15

Leu Asn Val Ser Tyr
20

<210> SEQ ID NO 72
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 72

Tyr Ala Cys Lys Arg Gly Gly Lys Ser Ser Gly Ser Ser Tyr Pro Val
1 5 10 15

Leu Asn Val Ser Met
20

<210> SEQ ID NO 73
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 73

Tyr Ala Cys Lys Arg Gly Gly Lys Ser Ser Gly Ser Ser Tyr Pro Val
1 5 10 15

Leu Asn Val Thr Tyr
20

<210> SEQ ID NO 74
<211> LENGTH: 21

<212> TYPE: PRT
<213> ORGANISM: Artificial Sequence
<220> FEATURE:
<223> OTHER INFORMATION: Immunogenic influenza peptide

<400> SEQUENCE: 74

Tyr Ala Cys Lys Arg Gly Gly Lys Ser Ser Gly Ser Ser Tyr Pro Val
1 5 10 15

Leu Asn Val Thr Met
20

<210> SEQ ID NO 75
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 75

Tyr Ala Cys Lys Arg Gly Gly Lys Ser Ser Gly Ser Ser Tyr Pro Val
1 5 10 15

Leu Ser Val Ser Tyr
20

<210> SEQ ID NO 76
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 76

Tyr Ala Cys Lys Arg Gly Gly Lys Ser Ser Gly Ser Ser Tyr Pro Val
1 5 10 15

Leu Ser Val Ser Met
20

<210> SEQ ID NO 77
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 77

Tyr Ala Cys Lys Arg Gly Gly Lys Ser Ser Gly Ser Ser Tyr Pro Val
1 5 10 15

Leu Ser Val Thr Tyr
20

<210> SEQ ID NO 78
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 78

Tyr Ala Cys Lys Arg Gly Gly Lys Ser Ser Gly Ser Ser Tyr Pro Val
1 5 10 15

Leu Ser Val Thr Met
20

<210> SEQ ID NO 79

<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 79

Tyr Ala Cys Lys His Gly Gly Lys Ser Ser Gly Ser Ser Tyr Pro Val
1 5 10 15

Leu Asn Val Ser Tyr
20

<210> SEQ ID NO 80
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 80

Tyr Ala Cys Lys His Gly Gly Lys Ser Ser Gly Ser Ser Tyr Pro Val
1 5 10 15

Leu Asn Val Ser Met
20

<210> SEQ ID NO 81
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 81

Tyr Ala Cys Lys His Gly Gly Lys Ser Ser Gly Ser Ser Tyr Pro Val
1 5 10 15

Leu Asn Val Thr Tyr
20

<210> SEQ ID NO 82
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 82

Tyr Ala Cys Lys His Gly Gly Lys Ser Ser Gly Ser Ser Tyr Pro Val
1 5 10 15

Leu Asn Val Thr Met
20

<210> SEQ ID NO 83
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 83

Tyr Ala Cys Lys His Gly Gly Lys Ser Ser Gly Ser Ser Tyr Pro Val
1 5 10 15

Leu Ser Val Ser Tyr
20

<210> SEQ ID NO 84
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 84

Tyr Ala Cys Lys His Gly Gly Lys Ser Ser Gly Ser Ser Tyr Pro Val
1 5 10 15

Leu Ser Val Ser Met
20

<210> SEQ ID NO 85
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 85

Tyr Ala Cys Lys His Gly Gly Lys Ser Ser Gly Ser Ser Tyr Pro Val
1 5 10 15

Leu Ser Val Thr Tyr
20

<210> SEQ ID NO 86
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 86

Tyr Ala Cys Lys His Gly Gly Lys Ser Ser Gly Ser Ser Tyr Pro Val
1 5 10 15

Leu Ser Val Thr Met
20

<210> SEQ ID NO 87
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 87

Tyr Ala Ser Lys Arg Gly Gly Lys Ser Ser Gly Ser Ser Tyr Pro Val
1 5 10 15

Leu Asn Val Ser Tyr
20

<210> SEQ ID NO 88
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 88

Tyr Ala Ser Lys Arg Gly Gly Lys Ser Ser Gly Ser Ser Tyr Pro Val
1 5 10 15

Leu Asn Val Ser Met
20

<210> SEQ ID NO 89
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 89

Tyr Ala Ser Lys Arg Gly Gly Lys Ser Ser Gly Ser Ser Tyr Pro Val
1 5 10 15

Leu Asn Val Thr Tyr
20

<210> SEQ ID NO 90
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 90

Tyr Ala Ser Lys Arg Gly Gly Lys Ser Ser Gly Ser Ser Tyr Pro Val
1 5 10 15

Leu Asn Val Thr Met
20

<210> SEQ ID NO 91
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 91

Tyr Ala Ser Lys Arg Gly Gly Lys Ser Ser Gly Ser Ser Tyr Pro Val
1 5 10 15

Leu Ser Val Ser Tyr
20

<210> SEQ ID NO 92
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 92

Tyr Ala Ser Lys Arg Gly Gly Lys Ser Ser Gly Ser Ser Tyr Pro Val
1 5 10 15

Leu Ser Val Ser Met
20

<210> SEQ ID NO 93
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 93

Tyr Ala Ser Lys Arg Gly Gly Lys Ser Ser Gly Ser Ser Tyr Pro Val
1 5 10 15

Leu Ser Val Thr Tyr
20

<210> SEQ ID NO 94
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 94

```
Tyr Ala Ser Lys Arg Gly Gly Lys Ser Ser Gly Ser Ser Tyr Pro Val
1               5                   10                  15

Leu Ser Val Thr Met
            20
```

<210> SEQ ID NO 95
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 95

```
Tyr Ala Ser Lys His Gly Gly Lys Ser Ser Gly Ser Ser Tyr Pro Val
1               5                   10                  15

Leu Asn Val Ser Tyr
            20
```

<210> SEQ ID NO 96
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 96

```
Tyr Ala Ser Lys His Gly Gly Lys Ser Ser Gly Ser Ser Tyr Pro Val
1               5                   10                  15

Leu Asn Val Ser Met
            20
```

<210> SEQ ID NO 97
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 97

```
Tyr Ala Ser Lys His Gly Gly Lys Ser Ser Gly Ser Ser Tyr Pro Val
1               5                   10                  15

Leu Asn Val Thr Tyr
            20
```

<210> SEQ ID NO 98
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 98

```
Tyr Ala Ser Lys His Gly Gly Lys Ser Ser Gly Ser Ser Tyr Pro Val
1               5                   10                  15

Leu Asn Val Thr Met
```

20

<210> SEQ ID NO 99
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 99

Tyr Ala Ser Lys His Gly Gly Lys Ser Ser Gly Ser Ser Tyr Pro Val
1 5 10 15

Leu Ser Val Ser Tyr
20

<210> SEQ ID NO 100
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 100

Tyr Ala Ser Lys His Gly Gly Lys Ser Ser Gly Ser Ser Tyr Pro Val
1 5 10 15

Leu Ser Val Ser Met
20

<210> SEQ ID NO 101
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 101

Tyr Ala Ser Lys His Gly Gly Lys Ser Ser Gly Ser Ser Tyr Pro Val
1 5 10 15

Leu Ser Val Thr Tyr
20

<210> SEQ ID NO 102
<211> LENGTH: 21
<212> TYPE: PRT
<213> ORGANISM: Artificial Sequence
<220> FEATURE:
<223> OTHER INFORMATION: Immunogenic influenza peptide

<400> SEQUENCE: 102

Tyr Ala Ser Lys His Gly Gly Lys Ser Ser Gly Ser Ser Tyr Pro Val
1 5 10 15

Leu Ser Val Thr Met
20

<210> SEQ ID NO 103
<211> LENGTH: 15
<212> TYPE: PRT
<213> ORGANISM: Artificial Sequence
<220> FEATURE:
<223> OTHER INFORMATION: Immunogenic influenza peptide

<400> SEQUENCE: 103

Ser Val Gln Arg Asn Leu Pro Phe Glu Lys Ser Thr Val Met Ala
1 5 10 15

<210> SEQ ID NO 104
<211> LENGTH: 15
<212> TYPE: PRT
<213> ORGANISM: Artificial Sequence
<220> FEATURE:
<223> OTHER INFORMATION: Immunogenic influenza peptide

<400> SEQUENCE: 104

Ser Val Gln Arg Asn Leu Pro Phe Glu Lys Ser Thr Ile Met Ala
1 5 10 15

<210> SEQ ID NO 105
<211> LENGTH: 15
<212> TYPE: PRT
<213> ORGANISM: Artificial Sequence
<220> FEATURE:
<223> OTHER INFORMATION: Immunogenic influenza peptide

<400> SEQUENCE: 105

Ser Val Gln Arg Asn Leu Pro Phe Glu Lys Thr Thr Val Met Ala
1 5 10 15

<210> SEQ ID NO 106
<211> LENGTH: 15
<212> TYPE: PRT
<213> ORGANISM: Artificial Sequence
<220> FEATURE:
<223> OTHER INFORMATION: Immunogenic influenza peptide

<400> SEQUENCE: 106

Ser Val Gln Arg Asn Leu Pro Phe Glu Lys Thr Thr Ile Met Ala
1 5 10 15

<210> SEQ ID NO 107
<211> LENGTH: 15
<212> TYPE: PRT
<213> ORGANISM: Artificial Sequence
<220> FEATURE:
<223> OTHER INFORMATION: Immunogenic influenza peptide

<400> SEQUENCE: 107

Ser Val Gln Arg Asn Leu Pro Phe Glu Arg Ser Thr Val Met Ala
1 5 10 15

<210> SEQ ID NO 108
<211> LENGTH: 15
<212> TYPE: PRT
<213> ORGANISM: Artificial Sequence
<220> FEATURE:
<223> OTHER INFORMATION: Immunogenic influenza peptide

<400> SEQUENCE: 108

Ser Val Gln Arg Asn Leu Pro Phe Glu Arg Ser Thr Ile Met Ala
1 5 10 15

<210> SEQ ID NO 109
<211> LENGTH: 15
<212> TYPE: PRT
<213> ORGANISM: Artificial Sequence
<220> FEATURE:
<223> OTHER INFORMATION: Immunogenic influenza peptide

<400> SEQUENCE: 109

Ser Val Gln Arg Asn Leu Pro Phe Glu Arg Thr Thr Val Met Ala
1 5 10 15

<210> SEQ ID NO 110
<211> LENGTH: 15
<212> TYPE: PRT
<213> ORGANISM: Artificial Sequence
<220> FEATURE:
<223> OTHER INFORMATION: Immunogenic influenza peptide

<400> SEQUENCE: 110

Ser Val Gln Arg Asn Leu Pro Phe Glu Arg Thr Thr Ile Met Ala
1 5 10 15

<210> SEQ ID NO 111
<211> LENGTH: 15
<212> TYPE: PRT
<213> ORGANISM: Artificial Sequence
<220> FEATURE:
<223> OTHER INFORMATION: Immunogenic influenza peptide

<400> SEQUENCE: 111

Ser Val Gln Arg Asn Leu Pro Phe Asp Lys Ser Thr Val Met Ala
1 5 10 15

<210> SEQ ID NO 112
<211> LENGTH: 15
<212> TYPE: PRT
<213> ORGANISM: Artificial Sequence
<220> FEATURE:
<223> OTHER INFORMATION: Immunogenic influenza peptide

<400> SEQUENCE: 112

Ser Val Gln Arg Asn Leu Pro Phe Asp Lys Ser Thr Ile Met Ala
1 5 10 15

<210> SEQ ID NO 113
<211> LENGTH: 15
<212> TYPE: PRT
<213> ORGANISM: Artificial Sequence
<220> FEATURE:
<223> OTHER INFORMATION: Immunogenic influenza peptide

<400> SEQUENCE: 113

Ser Val Gln Arg Asn Leu Pro Phe Asp Lys Thr Thr Val Met Ala
1 5 10 15

<210> SEQ ID NO 114
<211> LENGTH: 15
<212> TYPE: PRT
<213> ORGANISM: Artificial Sequence
<220> FEATURE:
<223> OTHER INFORMATION: Immunogenic influenza peptide

<400> SEQUENCE: 114

Ser Val Gln Arg Asn Leu Pro Phe Asp Lys Thr Thr Ile Met Ala
1 5 10 15

<210> SEQ ID NO 115
<211> LENGTH: 15
<212> TYPE: PRT
<213> ORGANISM: Artificial Sequence
<220> FEATURE:
<223> OTHER INFORMATION: Immunogenic influenza peptide

<400> SEQUENCE: 115

Ser Val Gln Arg Asn Leu Pro Phe Asp Arg Ser Thr Val Met Ala
1 5 10 15

<210> SEQ ID NO 116

<211> LENGTH: 15
<212> TYPE: PRT
<213> ORGANISM: Artificial Sequence
<220> FEATURE:
<223> OTHER INFORMATION: Immunogenic influenza peptide

<400> SEQUENCE: 116

Ser Val Gln Arg Asn Leu Pro Phe Asp Arg Ser Thr Ile Met Ala
1 5 10 15

<210> SEQ ID NO 117
<211> LENGTH: 15
<212> TYPE: PRT
<213> ORGANISM: Artificial Sequence
<220> FEATURE:
<223> OTHER INFORMATION: Immunogenic influenza peptide

<400> SEQUENCE: 117

Ser Val Gln Arg Asn Leu Pro Phe Asp Arg Thr Thr Val Met Ala
1 5 10 15

<210> SEQ ID NO 118
<211> LENGTH: 15
<212> TYPE: PRT
<213> ORGANISM: Artificial Sequence
<220> FEATURE:
<223> OTHER INFORMATION: Immunogenic influenza peptide

<400> SEQUENCE: 118

Ser Val Gln Arg Asn Leu Pro Phe Asp Arg Thr Thr Ile Met Ala
1 5 10 15

<210> SEQ ID NO 119
<211> LENGTH: 16
<212> TYPE: PRT
<213> ORGANISM: Artificial Sequence
<220> FEATURE:
<223> OTHER INFORMATION: Immunogenic influenza peptide

<400> SEQUENCE: 119

Asn Met Gly Ser Ser Thr Leu Glu Leu Arg Ser Gly Tyr Trp Ala Ile
1 5 10 15

<210> SEQ ID NO 120
<211> LENGTH: 16
<212> TYPE: PRT
<213> ORGANISM: Artificial Sequence
<220> FEATURE:
<223> OTHER INFORMATION: Immunogenic influenza peptide

<400> SEQUENCE: 120

Asn Met Gly Ser Ser Thr Leu Glu Leu Arg Ser Arg Tyr Trp Ala Ile
1 5 10 15

<210> SEQ ID NO 121
<211> LENGTH: 16
<212> TYPE: PRT
<213> ORGANISM: Artificial Sequence
<220> FEATURE:
<223> OTHER INFORMATION: Immunogenic influenza peptide

<400> SEQUENCE: 121

Asn Met Glu Ser Ser Thr Leu Glu Leu Arg Ser Gly Tyr Trp Ala Ile
1 5 10 15

<210> SEQ ID NO 122
<211> LENGTH: 16

<212> TYPE: PRT
<213> ORGANISM: Artificial Sequence
<220> FEATURE:
<223> OTHER INFORMATION: Immunogenic influenza peptide

<400> SEQUENCE: 122

Asn Met Glu Ser Ser Thr Leu Glu Leu Arg Ser Arg Tyr Trp Ala Ile
1 5 10 15

<210> SEQ ID NO 123
<211> LENGTH: 16
<212> TYPE: PRT
<213> ORGANISM: Artificial Sequence
<220> FEATURE:
<223> OTHER INFORMATION: Immunogenic influenza peptide

<400> SEQUENCE: 123

Asn Ile Gly Ser Ser Thr Leu Glu Leu Arg Ser Gly Tyr Trp Ala Ile
1 5 10 15

<210> SEQ ID NO 124
<211> LENGTH: 16
<212> TYPE: PRT
<213> ORGANISM: Artificial Sequence
<220> FEATURE:
<223> OTHER INFORMATION: Immunogenic influenza peptide

<400> SEQUENCE: 124

Asn Ile Gly Ser Ser Thr Leu Glu Leu Arg Ser Arg Tyr Trp Ala Ile
1 5 10 15

<210> SEQ ID NO 125
<211> LENGTH: 16
<212> TYPE: PRT
<213> ORGANISM: Artificial Sequence
<220> FEATURE:
<223> OTHER INFORMATION: Immunogenic influenza peptide

<400> SEQUENCE: 125

Asn Ile Glu Ser Ser Thr Leu Glu Leu Arg Ser Gly Tyr Trp Ala Ile
1 5 10 15

<210> SEQ ID NO 126
<211> LENGTH: 16
<212> TYPE: PRT
<213> ORGANISM: Artificial Sequence
<220> FEATURE:
<223> OTHER INFORMATION: Immunogenic influenza peptide

<400> SEQUENCE: 126

Asn Ile Glu Ser Ser Thr Leu Glu Leu Arg Ser Arg Tyr Trp Ala Ile
1 5 10 15

<210> SEQ ID NO 127
<211> LENGTH: 16
<212> TYPE: PRT
<213> ORGANISM: Artificial Sequence
<220> FEATURE:
<223> OTHER INFORMATION: Immunogenic influenza peptide

<400> SEQUENCE: 127

Ala Met Gly Ser Ser Thr Leu Glu Leu Arg Ser Gly Tyr Trp Ala Ile
1 5 10 15

<210> SEQ ID NO 128
<211> LENGTH: 16
<212> TYPE: PRT

<213> ORGANISM: Artificial Sequence
<220> FEATURE:
<223> OTHER INFORMATION: Immunogenic influenza peptide

<400> SEQUENCE: 128

Ala Met Gly Ser Ser Thr Leu Glu Leu Arg Ser Arg Tyr Trp Ala Ile
1 5 10 15

<210> SEQ ID NO 129
<211> LENGTH: 16
<212> TYPE: PRT
<213> ORGANISM: Artificial Sequence
<220> FEATURE:
<223> OTHER INFORMATION: Immunogenic influenza peptide

<400> SEQUENCE: 129

Ala Met Glu Ser Ser Thr Leu Glu Leu Arg Ser Gly Tyr Trp Ala Ile
1 5 10 15

<210> SEQ ID NO 130
<211> LENGTH: 16
<212> TYPE: PRT
<213> ORGANISM: Artificial Sequence
<220> FEATURE:
<223> OTHER INFORMATION: Immunogenic influenza peptide

<400> SEQUENCE: 130

Ala Met Glu Ser Ser Thr Leu Glu Leu Arg Ser Arg Tyr Trp Ala Ile
1 5 10 15

<210> SEQ ID NO 131
<211> LENGTH: 16
<212> TYPE: PRT
<213> ORGANISM: Artificial Sequence
<220> FEATURE:
<223> OTHER INFORMATION: Immunogenic influenza peptide

<400> SEQUENCE: 131

Ala Ile Gly Ser Ser Thr Leu Glu Leu Arg Ser Gly Tyr Trp Ala Ile
1 5 10 15

<210> SEQ ID NO 132
<211> LENGTH: 16
<212> TYPE: PRT
<213> ORGANISM: Artificial Sequence
<220> FEATURE:
<223> OTHER INFORMATION: Immunogenic influenza peptide

<400> SEQUENCE: 132

Ala Ile Gly Ser Ser Thr Leu Glu Leu Arg Ser Arg Tyr Trp Ala Ile
1 5 10 15

<210> SEQ ID NO 133
<211> LENGTH: 16
<212> TYPE: PRT
<213> ORGANISM: Artificial Sequence
<220> FEATURE:
<223> OTHER INFORMATION: Immunogenic influenza peptide

<400> SEQUENCE: 133

Ala Ile Glu Ser Ser Thr Leu Glu Leu Arg Ser Gly Tyr Trp Ala Ile
1 5 10 15

<210> SEQ ID NO 134
<211> LENGTH: 16
<212> TYPE: PRT
<213> ORGANISM: Artificial Sequence -continued

```
<220> FEATURE:
<223> OTHER INFORMATION: Immunogenic influenza peptide

<400> SEQUENCE: 134

Ala Ile Glu Ser Ser Thr Leu Glu Leu Arg Ser Arg Tyr Trp Ala Ile
1               5                   10                  15
```